US012626807B2

(12) United States Patent
Shelton, IV et al.

(10) Patent No.: US 12,626,807 B2
(45) Date of Patent: May 12, 2026

(54) AGGREGATED NETWORK OF SURGICAL HUBS FOR EFFICIENCY ANALYSIS

(71) Applicant: Cilag GmbH International, Zug (CH)

(72) Inventors: Frederick E. Shelton, IV, Hillsboro, OH (US); Kevin M. Fiebig, Cincinnati, OH (US); Taylor W. Aronhalt, Loveland, OH (US); Charles J. Scheib, Loveland, OH (US)

(73) Assignee: Cilag GmbH International, Zug (CH)

( * ) Notice: Subject to any disclaimer, the term of this patent is extended or adjusted under 35 U.S.C. 154(b) by 621 days.

(21) Appl. No.: 17/335,420

(22) Filed: Jun. 1, 2021

(65) Prior Publication Data

US 2022/0384017 A1     Dec. 1, 2022

Related U.S. Application Data

(60) Provisional application No. 63/194,675, filed on May 28, 2021.

(51) Int. Cl.
*G16H 40/20*     (2018.01)
*A61B 5/01*     (2006.01)
(Continued)

(52) U.S. Cl.
CPC .............. *G16H 40/20* (2018.01); *A61B 5/01* (2013.01); *A61B 5/165* (2013.01); *A61B 34/10* (2016.02);
(Continued)

(58) Field of Classification Search
USPC .......................................................... 705/2–3
See application file for complete search history.

(56) References Cited

U.S. PATENT DOCUMENTS 9,345,481 B2     5/2016  Hall et al.
2011/0276340 A1  11/2011  Deboer et al.
(Continued)

FOREIGN PATENT DOCUMENTS

WO     2020-084625 A1     4/2020

OTHER PUBLICATIONS

Karimi, E. (2018). Integrative predictive support systems for Hospital's resource planning and scheduling (Order No. 27537028). Available from ProQuest Dissertations and Theses Professional. (2291450170). Retrieved from https://dialog.proquest.com/professional/docview/2291450170?accountid=131444 (Year: 2018).*
(Continued)

*Primary Examiner* — Bennett Stephen Erickson
(74) *Attorney, Agent, or Firm* — Condo Roccia Koptiw LLP

(57) ABSTRACT

A computing system may obtain and aggregate surgical monitoring data associated with multiple surgical procedures in multiple operating rooms (ORs), and the surgical monitoring data may be obtained via the surgical hubs in the ORs. Surgical resource utilization adjustments may be generated based on the aggregated surgical resource monitoring data, and an output may be generated based on the determined surgical resource utilization adjustment. The aggregated data may be used to generate resource allocation adjustments for the ORs. Resource allocation adjustments may include healthcare professional (HCP) assignment adjustments, surgery scheduling adjustments, surgical instrument allocation adjustments, OR layout adjustments, and/or medical facility layout adjustment(s), etc. The computing system may generate a control signal for adjusting an HCP assignment, adjusting surgery scheduling, adjusting surgical instrument allocation, adjusting surgical plans, notifying HCPs and/or administrators of surgical resource
(Continued)

adjustments, notifying potential issues and/or providing recommendations.

11 Claims, 16 Drawing Sheets

(51) Int. Cl.

| | |
|---|---|
| *A61B 5/16* | (2006.01) |
| *A61B 34/00* | (2016.01) |
| *A61B 34/10* | (2016.01) |
| *A61B 34/20* | (2016.01) |
| *A61B 34/30* | (2016.01) |
| *A61B 90/00* | (2016.01) |
| *A61B 90/30* | (2016.01) |
| *A61M 21/02* | (2006.01) |
| *G01N 33/00* | (2006.01) |
| *G05B 13/04* | (2006.01) |
| *G05B 19/042* | (2006.01) |
| *G07C 9/32* | (2020.01) |
| *G16H 20/40* | (2018.01) |
| *G16H 40/40* | (2018.01) |
| *G16H 40/63* | (2018.01) |
| *G16H 40/67* | (2018.01) |
| *G16H 50/20* | (2018.01) |
| *G16H 50/30* | (2018.01) |
| *A61M 21/00* | (2006.01) |
| *G16H 20/70* | (2018.01) |

(52) U.S. Cl.
CPC ............. *A61B 34/20* (2016.02); *A61B 34/25* (2016.02); *A61B 90/30* (2016.02); *A61M 21/02* (2013.01); *G01N 33/0075* (2013.01); *G05B 13/042* (2013.01); *G05B 19/042* (2013.01); *G07C 9/32* (2020.01); *G16H 20/40* (2018.01); *G16H 40/40* (2018.01); *G16H 40/63* (2018.01); *G16H 40/67* (2018.01); *G16H 50/20* (2018.01); *G16H 50/30* (2018.01); *A61B 2034/252* (2016.02); *A61B 2034/254* (2016.02); *A61B 34/30* (2016.02); *A61B 90/361* (2016.02); *A61B 90/37* (2016.02); *A61B 2090/372* (2016.02); *A61B 2505/05* (2013.01); *A61M 2021/0027* (2013.01); *G05B 2219/25257* (2013.01); *G16H 20/70* (2018.01)

(56) References Cited

U.S. PATENT DOCUMENTS

| | | | |
|---|---|---|---|
| 2014/0263552 A1 | 9/2014 | Hall et al. | |
| 2014/0270375 A1* | 9/2014 | Canavan ................ | A61B 5/681 |
| | | | 382/103 |
| 2014/0357984 A1 | 12/2014 | Wallace et al. | |
| 2016/0179460 A1 | 6/2016 | Macdonald | |
| 2017/0086926 A1 | 3/2017 | Amling et al. | |
| 2017/0090865 A1 | 3/2017 | Armstrong-muntner et al. | |
| 2017/0296213 A1 | 10/2017 | Swendsgard et al. | |
| 2017/0372022 A1* | 12/2017 | Cuellar ............... | G06F 21/6245 |
| 2018/0092706 A1 | 4/2018 | Anderson et al. | |
| 2018/0247024 A1* | 8/2018 | Divine ................... | G16H 40/20 |
| 2018/0344308 A1* | 12/2018 | Nawana ............... | A61B 5/0022 |
| 2018/0360452 A1 | 12/2018 | Shelton et al. | |
| 2019/0117217 A1 | 4/2019 | Overmyer et al. | |
| 2019/0200844 A1 | 7/2019 | Shelton et al. | |
| 2019/0201087 A1 | 7/2019 | Shelton, IV et al. | |
| 2019/0201136 A1 | 7/2019 | Shelton et al. | |
| 2019/0201137 A1 | 7/2019 | Shelton et al. | |
| 2019/0206551 A1 | 7/2019 | Yates et al. | |
| 2019/0206569 A1 | 7/2019 | Shelton et al. | |
| 2019/0259479 A1* | 8/2019 | Ginsburg ............... | G16H 10/60 |
| 2020/0397528 A1* | 12/2020 | Zapata ................... | A61B 90/30 |
| 2021/0015554 A1 | 1/2021 | Chow et al. | |
| 2021/0059857 A1 | 3/2021 | Voigt et al. | |
| 2022/0233119 A1 | 7/2022 | Shelton et al. | |
| 2022/0233241 A1 | 7/2022 | Shelton et al. | |
| 2022/0233244 A1 | 7/2022 | Shelton et al. | |
| 2022/0233253 A1 | 7/2022 | Shelton et al. | |
| 2022/0233267 A1 | 7/2022 | Shelton et al. | |
| 2022/0238209 A1 | 7/2022 | Shelton et al. | |
| 2022/0378520 A1 | 12/2022 | Shelton, IV et al. | |
| 2022/0384011 A1 | 12/2022 | Shelton, IV et al. | |
| 2022/0384016 A1 | 12/2022 | Shelton, IV et al. | |
| 2022/0384017 A1 | 12/2022 | Shelton, IV et al. | |
| 2022/0384018 A1 | 12/2022 | Shelton, IV et al. | |
| 2022/0384019 A1 | 12/2022 | Shelton, IV et al. | |
| 2022/0384025 A1 | 12/2022 | Shelton, IV et al. | |

OTHER PUBLICATIONS

U.S. Appl. No. 62/611,341, filed Dec. 28, 2017, Shelton, et al.
U.S. Appl. No. 17/335,738, filed Jun. 1, 2021, Shelton, et al.
U.S. Appl. No. 17/335,358, filed Jun. 1, 2021, Shelton, et al.
U.S. Appl. No. 17/335,362, filed Jun. 1, 2021, Shelton, et al.
U.S. Appl. No. 17/335,566, filed Jun. 1, 2021, Shelton, et al.
U.S. Appl. No. 17/335,669, filed Jun. 1, 2021, Shelton, et al.
U.S. Appl. No. 17/335,688, filed Jun. 1, 2021, Shelton, et al.

* cited by examiner

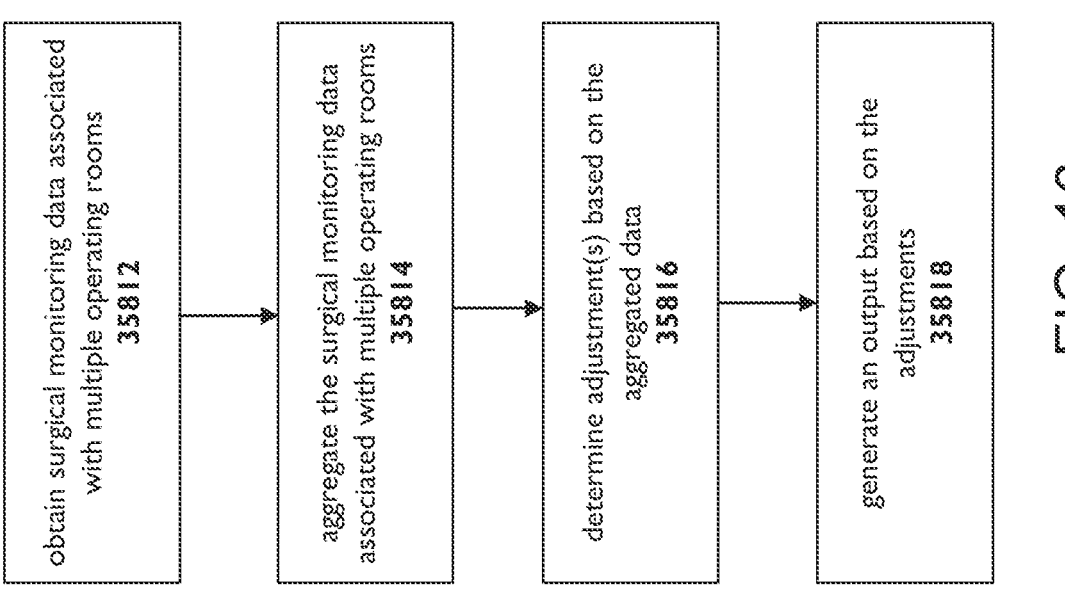

obtain surgical monitoring data associated with multiple operating rooms
35812 aggregate the surgical monitoring data associated with multiple operating rooms
35814 determine adjustment(s) based on the aggregated data
35816 generate an output based on the adjustments
35818

FIG. 16

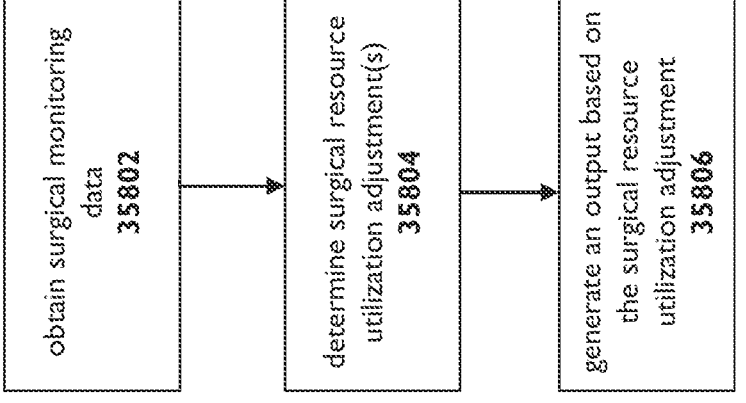

obtain surgical monitoring data
35802 determine surgical resource utilization adjustment(s)
35804 generate an output based on the surgical resource utilization adjustment
35806

FIG. 15

AGGREGATED NETWORK OF SURGICAL HUBS FOR EFFICIENCY ANALYSIS

CROSS-REFERENCE TO RELATED APPLICATIONS

This application claims the benefit of Provisional U.S. Patent Application No. 63/194,675, filed on May 28, 2021, the disclosure of which is incorporated herein by reference in its entirety.

This application is related to the following, filed contemporaneously, the contents of which are incorporated by reference herein:

U.S. patent application Ser. No. 17/335,738, filed Jun. 1, 2021, entitled METHOD OF MONITORING AND ANALYZING SURGICAL PROCEDURES.

BACKGROUND

Successful surgeries depend on the expertise of several types of operating room (OR) team members. The roles of different OR personnel may be different. Surgeons make the critical decisions involved in directing the course of a procedure. Surgeons may perform the incisions involved in an operation. Anesthesiologists or nurse anesthetists may be in charge of safely administering anesthesia to patients prior to surgery, monitoring them during surgery and making sure that they safely come out of anesthesia after the operation. A circulating technician may bring the patient to the operating room, tie the surgical gowns of surgeons and other personnel, deliver needed additional supplies such as instruments and medicine, and document the surgery. Scrub technicians may sterilize instruments before and after the surgery, keep the surgical field organized during surgery, and provide the surgeon with needed instruments. Registered nurses may perform the duties typically associated with surgical technicians, including acting as circulating nurses and scrub nurses. In addition, a nurse may act as the first assistant to the surgeon. OR human traffic has been implicated as a cause of surgical site infection.

SUMMARY

A computing system may be configured to obtain and aggregate surgical monitoring data associated with multiple surgical procedures. The multiple surgical procedures may be associated with one or more operating rooms (ORs), and the surgical monitoring data may be obtained via one or more surgical hubs in the OR(s). Surgical resource utilization adjustment(s) may be generated based on the aggregated surgical resource monitoring data, and an output may be generated based on the determined surgical resource utilization adjustment. For example, resource allocation and utilization data and surgical outcome data across multiple ORs may be obtained and aggregated. The aggregated data may be used to generate resource allocation adjustment(s) for the ORs. Resource allocation adjustment(s) may include, but not limited to, healthcare personnel (HCP) assignment adjustment(s), surgery scheduling adjustment(s), surgical instrument allocation adjustment(s), OR layout adjustment(s), and/or medical facility layout adjustment(s), etc.

For example, the surgical monitoring data may include surgical resource monitoring data, HCP monitoring data, surgical instrument utilization data, and/or surgical procedure progression data associated with multiple surgical procedures that may take place in multiple ORs. The surgical monitoring data may include instrument stock and utilization data, OR turnover data and/or cost data associated with the surgical procedures. HCP efficiency may be analyzed based on the aggregated OR utilization data, the aggregated OR turnover data, the aggregated HCP reposition data, and/or the aggregated instrument exchange data associated with the plurality of surgical procedures.

Procedure summary information associated with multiple ORs may be generated based on the aggregated surgical monitoring data. Procedure summary information may include planned, actual and projected HCP assignment information, planned, actual and projected surgical step information, and/or planned, actual and projected surgical resource information.

The computing system may generate an output based on the determined adjustment(s). The output may include, but not limited to, a control signal for adjusting an HCP assignment, adjusting surgery scheduling, adjusting surgical instrument allocation, adjusting surgical plan(s), notifying HCPs and/or administrators of surgical resource adjustments, notifying potential issues and/or providing recommendations.

For example, a set of repetitive trips may be identified based on the aggregated HCP monitoring data, and surgical tasks associated with the set of repetitive trips may be identified based on the aggregated surgical procedure progression data associated with the surgical procedures. HCP task assignment adjustment(s) may be determined for reducing the distance traveled associated with the identified surgical tasks. For example, a set of combinable tasks may be identified, from the surgical tasks associated with the repetitive trips, based on the aggregated surgical procedure progression data. The computing system may generate an output to indicate the combinable tasks. For example, aspect(s) of OR layout associated with the identified repetitive trips may be identified, and OR layout adjustment(s) may be generated such that a path length associated with the set of repetitive trips may be reduced.

Surgical procedure planning data associated with multiple surgical procedures may be from multiple surgical hubs and may be used to generate updated surgical procedure plans based on the surgical procedure progression data with the surgical procedures. Planned HCP task assignment associated with the surgical procedures may be obtained and updated based on the updated surgical procedure plans and the HCP monitoring data associated with surgical procedures. Surgical instrument allocation data associated with the surgical procedures may be obtained and, predicted or projected surgical instrument utilization data associated with the surgical procedures may be determined based on the aggregated surgical instrument utilization monitoring data and the updated surgical procedure plans.

For example, the computing system may assign a task to HCP(s) based on the aggregated surgical monitoring data. The computing system may predict that the task is to be performed during a time period. An HCP's energy level and/or fatigue level during the time period may be projected based on the biomarker measurement data associated with the HCP, and the availability of the HCP during time period may be determined based on the surgical procedure planning data and the surgical procedure progress data. Whether to assign the task to the HCP may be determined based on the projected fatigue level and the availability of the HCP during the time period.

BRIEF DESCRIPTION OF THE DRAWINGS

FIG. 15 shows an example efficiency analysis based on surgical monitoring data.

FIG. 16 shows an example efficiency analysis based on aggregated surgical monitoring data across multiple ORs.

DETAILED DESCRIPTION

Figure 1:
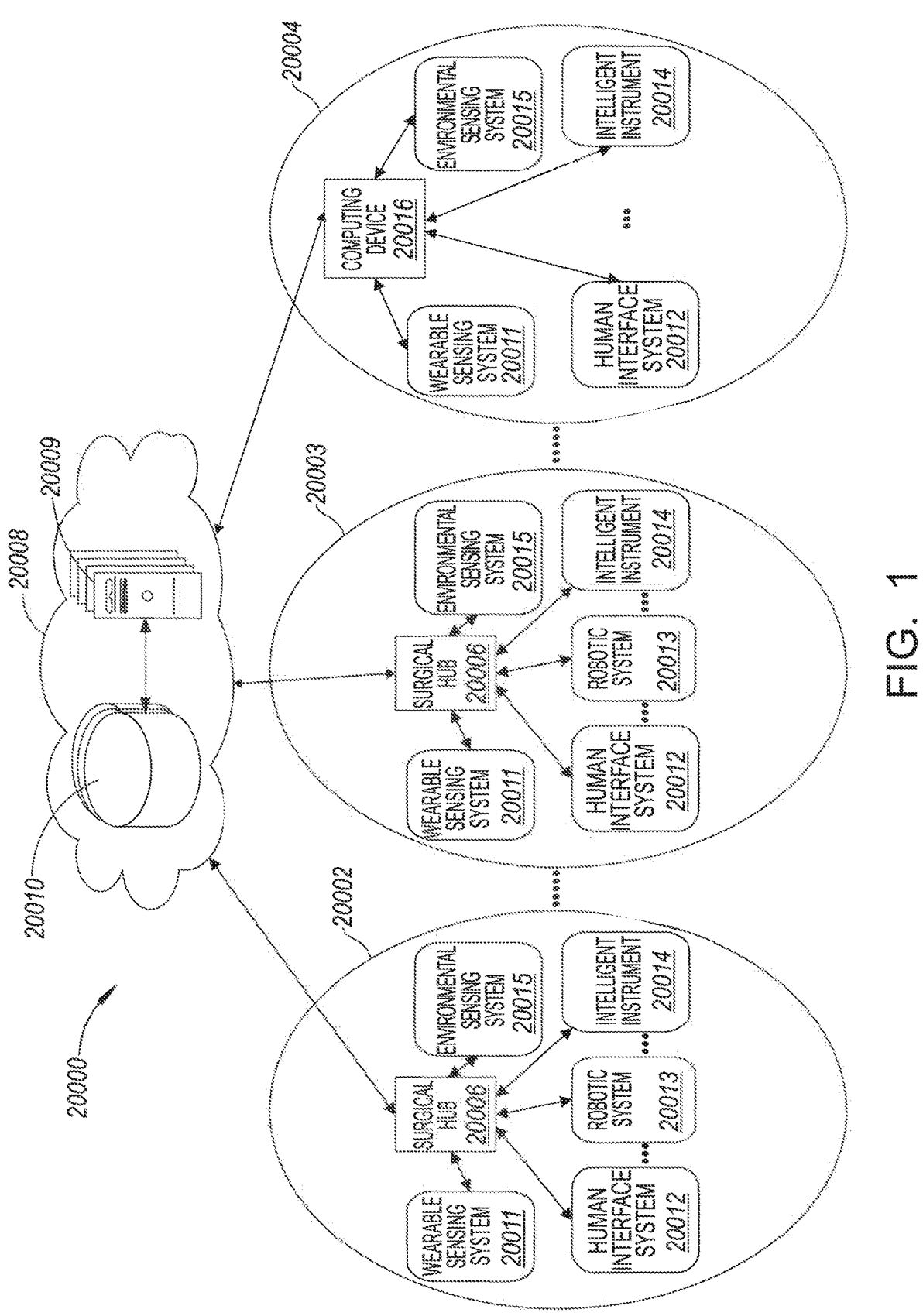
FIG. 1 is a block diagram of a computer-implemented healthcare personnel (HCP) monitoring system.

FIG. 1 is a block diagram of a computer-implemented HCP monitoring system 20000. An example HCP monitoring system such as the HCP monitoring system 20000 may include one or more HCP monitoring systems (e.g., HCP monitoring sub-systems) 20002, 20003 and 20004. For example, HCP monitoring system 20002 may include a computer-implemented interactive surgical system. For example, HCP monitoring system 20002 may include at least one of the following: a surgical hub 20006 in communication with a cloud computing system 20008, for example, as described in FIG. 2. An HCP monitoring system may include at least one of the following: a surgical hub 20006 or a computing device 20016 in communication with a could computing system 20008. The cloud computing system 20008 may include at least one remote cloud server 20009 and at least one remote cloud storage unit 20010. Example HCP monitoring systems 20002, 20003, or 20004 may include a wearable sensing system 20011, an environmental sensing system 20015, a robotic system 20013, one or more intelligent instruments 20014, human interface system 20012, etc. The human interface system is also referred herein as the human interface device. The wearable sensing system 20011 may include one or more HCP sensing systems, and/or one or more patient sensing systems. The environmental sensing system 20015 may include one or more devices, for example, used for measuring one or more environmental attributes, for example, as further described in FIG. 2. The robotic system 20013 may include a plurality of devices used for performing a surgical procedure, for example, as further described in FIG. 2.

The HCP monitoring system 20002 may be in communication with a remote server 20009 that may be part of a cloud computing system 20008. In an example, HCP monitoring system 20002 may be in communication with a remote server 20009 via an internet service provider's cable/FIOS networking node. In an example, a patient sensing system may be in direct communication with a remote server 20009. The HCP monitoring system 20002 and/or a component therein may communicate with the remote servers 20009 via a cellular transmission/reception point (TRP) or a base station using one or more of the following cellular protocols: GSM/GPRS/EDGE (2G), UMTS/HSPA (3G), long term evolution (LTE) or 4G, LTE-Advanced (LTE-A), new radio (NR) or 5G.

A surgical hub 20006 may have cooperative interactions with one of more means of displaying the image from the laparoscopic scope and information from one or more other smart devices and one or more sensing systems 20011. The surgical hub 20006 may interact with one or more sensing systems 20011, one or more smart devices, and multiple displays. The surgical hub 20006 may be configured to gather measurement data from the one or more sensing systems 20011 and send notifications or control messages to the one or more sensing systems 20011. The surgical hub 20006 may send and/or receive information including notification information to and/or from the human interface system 20012. The human interface system 20012 may include one or more human interface devices (HIDs). The surgical hub 20006 may send and/or receive notification information or control information to audio, display and/or control information to various devices that are in communication with the surgical hub.

For example, the sensing systems 20001 may include the wearable sensing system 20011 (which may include one or more HCP sensing systems and one or more patient sensing systems) and the environmental sensing system 20015 as discussed in FIG. 1. The one or more sensing systems 20001 may measure data relating to various biomarkers. The one or more sensing systems 20001 may measure the biomarkers using one or more sensors, for example, photosensors (e.g., photodiodes, photoresistors), mechanical sensors (e.g., motion sensors), acoustic sensors, electrical sensors, electrochemical sensors, thermoelectric sensors, infrared sensors, etc. The one or more sensors may measure the biomarkers as described herein using one of more of the following sensing technologies: photoplethysmography, electrocardiography, electroencephalography, colorimetry, impedimentary, potentiometry, amperometry, etc.

The biomarkers measured by the one or more sensing systems 20001 may include, but are not limited to, sleep, core body temperature, maximal oxygen consumption, physical activity, alcohol consumption, respiration rate, oxygen saturation, blood pressure, blood sugar, heart rate variability, blood potential of hydrogen, hydration state, heart rate, skin conductance, peripheral temperature, tissue perfusion pressure, coughing and sneezing, gastrointestinal motility, gastrointestinal tract imaging, respiratory tract bacteria, edema, mental aspects, sweat, circulating tumor cells, autonomic tone, circadian rhythm, and/or menstrual cycle.

The biomarkers may relate to physiologic systems, which may include, but are not limited to, behavior and psychology, cardiovascular system, renal system, skin system, nervous system, gastrointestinal system, respiratory system, endocrine system, immune system, tumor, musculoskeletal system, and/or reproductive system. Information from the biomarkers may be determined and/or used by the computer-implemented patient and HCP monitoring system 20000, for example. The information from the biomarkers may be determined and/or used by the computer-implemented patient and HCP monitoring system 20000 to improve said systems and/or to improve patient outcomes, for example. The one or more sensing systems 20001, biomarkers 20005, and physiological systems are described in more detail in U.S. application Ser. No. 17/156,287, titled METHOD OF ADJUSTING A SURGICAL PARAMETER BASED ON BIOMARKER MEASUREMENTS, filed Jan. 22, 2021, the disclosure of which is herein incorporated by reference in its entirety.

Figure 2:
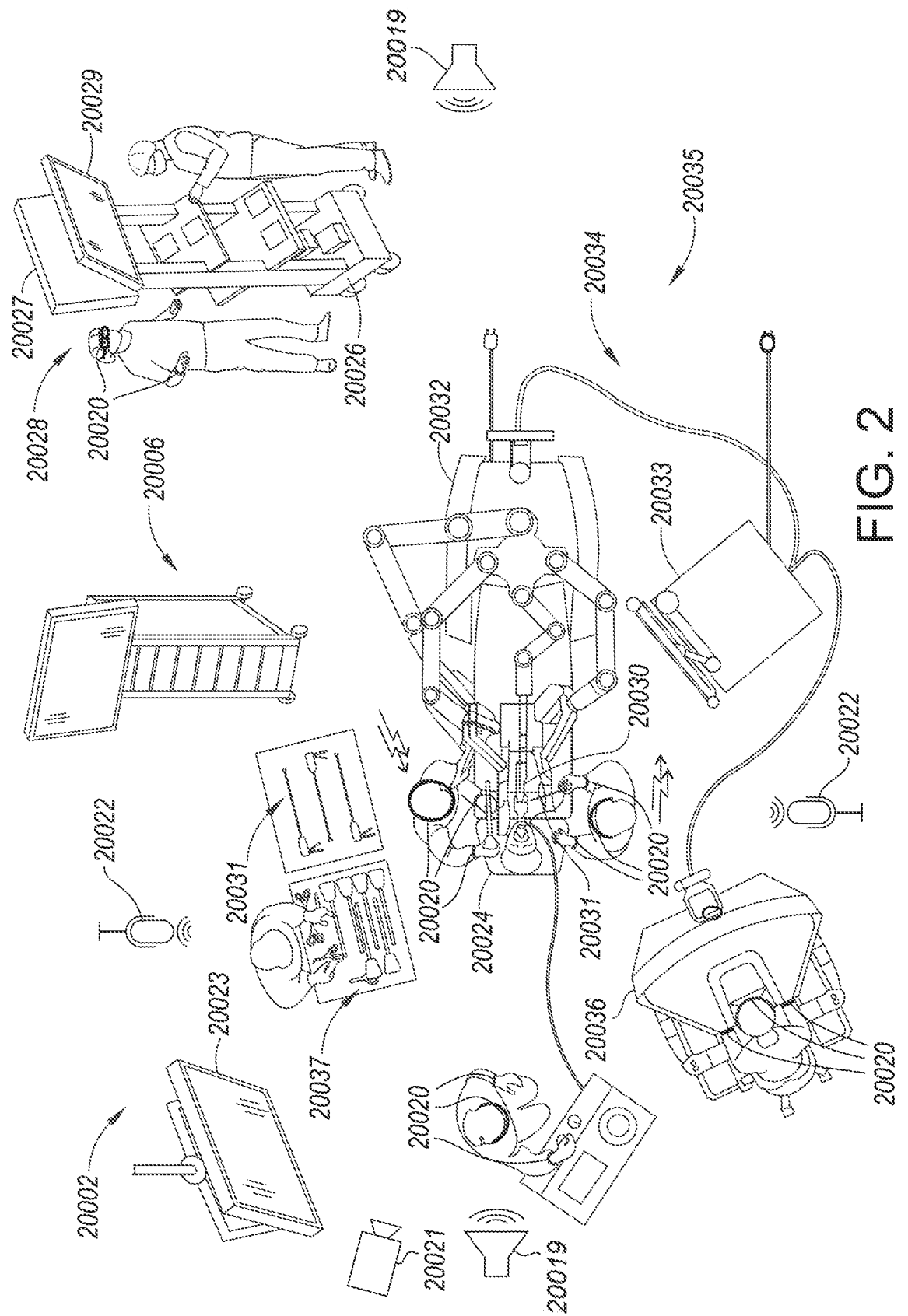
FIG. 2 shows an example of an HCP monitoring system in a surgical operating room.

FIG. 2 shows an example of an HCP monitoring system 20002 in a surgical operating room. As illustrated in FIG. 2, a patient is being operated on by one or more health care professionals (HCPs). The HCPs are being monitored by one or more HCP sensing systems 20020 worn by the HCPs. The HCPs and the environment surrounding the HCPs may also be monitored by one or more environmental sensing systems including, for example, a set of cameras 20021, a set of microphones 20022, and other sensors, etc. that may be deployed in the operating room. The HCP sensing systems 20020 and the environmental sensing systems may be in communication with a surgical hub 20006, which in turn may be in communication with one or more cloud servers 20009 of the cloud computing system 20008, as shown in FIG. 1. The environmental sensing systems may be used for measuring one or more environmental attributes, for example, HCP position in the surgical theater, HCP movements, ambient noise in the surgical theater, temperature/humidity in the surgical theater, etc.

As illustrated in FIG. 2, a primary display 20023 and one or more audio output devices (e.g., speakers 20019) are positioned in the sterile field to be visible to an operator at the operating table 20024. In addition, a visualization/notification tower 20026 is positioned outside the sterile field. The visualization/notification tower 20026 may include a first non-sterile human interactive device (HID) 20027 and a second non-sterile HID 20029, which may face away from each other. The HID may be a display or a display with a touchscreen allowing a human to interface directly with the HID. A human interface system, guided by the surgical hub 20006, may be configured to utilize the HIDs 20027, 20029, and 20023 to coordinate information flow to operators inside and outside the sterile field. In an example, the surgical hub 20006 may cause an HID (e.g., the primary HID 20023) to display a notification and/or information about the patient and/or a surgical procedure step. In an example, the surgical hub 20006 may prompt for and/or receive input from personnel in the sterile field or in the non-sterile area. In an example, the surgical hub 20006 may cause an HID to display a snapshot of a surgical site, as recorded by an imaging device 20030, on a non-sterile HID 20027 or 20029, while maintaining a live feed of the surgical site on the primary HID 20023. The snapshot on the non-sterile display 20027 or 20029 can permit a non-sterile operator to perform a diagnostic step relevant to the surgical procedure, for example.

In one aspect, the surgical hub 20006 may be configured to route a diagnostic input or feedback entered by a non-sterile operator at the visualization tower 20026 to the primary display 20023 within the sterile field, where it can be viewed by a sterile operator at the operating table. In one example, the input can be in the form of a modification to the snapshot displayed on the non-sterile display 20027 or 20029, which can be routed to the primary display 20023 by the surgical hub 20006.

Referring to FIG. 2, a surgical instrument 20031 is being used in the surgical procedure as part of the HCP monitoring system 20002. The hub 20006 may be configured to coordinate information flow to a display of the surgical instrument 20031. For example, in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety. A diagnostic input or feedback entered by a non-sterile operator at the visualization tower 20026 can be routed by the hub 20006 to the surgical instrument display within the sterile field, where it can be viewed by the operator of the surgical instrument 20031. Example surgical instruments that are suitable for use with the HCP monitoring system 20002 are described under the heading "Surgical Instrument Hardware" and in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety, for example.

FIG. 2 illustrates an example of an HCP monitoring system 20002 being used to perform a surgical procedure on a patient who is lying down on an operating table 20024 in a surgical operating room 20035. A robotic system 20034 may be used in the surgical procedure as a part of the HCP monitoring system 20002. The robotic system 20034 may include a surgeon's console 20036, a patient side cart 20032 (surgical robot), and a surgical robotic hub 20033. The patient side cart 20032 can manipulate at least one removably coupled surgical tool 20037 through a minimally invasive incision in the body of the patient while the surgeon views the surgical site through the surgeon's console 20036. An image of the surgical site can be obtained by a medical imaging device 20030, which can be manipulated by the patient side cart 20032 to orient the imaging device 20030. The robotic hub 20033 can be used to process the images of the surgical site for subsequent display to the surgeon through the surgeon's console 20036.

Other types of robotic systems can be readily adapted for use with the HCP monitoring system 20002. Various examples of robotic systems and surgical tools that are suitable for use with the present disclosure are described in U.S. Patent Application Publication No. US 2019-0201137 A1 (U.S. patent application Ser. No. 16/209,407), titled METHOD OF ROBOTIC HUB COMMUNICATION, DETECTION, AND CONTROL, filed Dec. 4, 2018, the disclosure of which is herein incorporated by reference in its entirety.

Various examples of cloud-based analytics that are performed by the cloud computing system 20008, and are suitable for use with the present disclosure, are described in U.S. Patent Application Publication No. US 2019-0206569 A1 (U.S. patent application Ser. No. 16/209,403), titled METHOD OF CLOUD BASED DATA ANALYTICS FOR USE WITH THE HUB, filed Dec. 4, 2018, the disclosure of which is herein incorporated by reference in its entirety.

In various aspects, the imaging device 20030 may include at least one image sensor and one or more optical components. Suitable image sensors may include, but are not limited to, Charge-Coupled Device (CCD) sensors and Complementary Metal-Oxide Semiconductor (CMOS) sensors.

The optical components of the imaging device 20030 may include one or more illumination sources and/or one or more lenses. The one or more illumination sources may be directed to illuminate portions of the surgical field. The one or more image sensors may receive light reflected or refracted from the surgical field, including light reflected or refracted from tissue and/or surgical instruments.

The one or more illumination sources may be configured to radiate electromagnetic energy in the visible spectrum as well as the invisible spectrum. The visible spectrum, sometimes referred to as the optical spectrum or luminous spectrum, is that portion of the electromagnetic spectrum that is visible to (i.e., can be detected by) the human eye and may be referred to as visible light or simply light. A typical human eye will respond to wavelengths in air that range from about 380 nm to about 750 nm.

The invisible spectrum (e.g., the non-luminous spectrum) is that portion of the electromagnetic spectrum that lies below and above the visible spectrum (i.e., wavelengths below about 380 nm and above about 750 nm). The invisible spectrum is not detectable by the human eye. Wavelengths greater than about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

In various aspects, the imaging device 20030 is configured for use in a minimally invasive procedure. Examples of imaging devices suitable for use with the present disclosure include, but are not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngoneproscope, sigmoidoscope, thoracoscope, and ureteroscope.

The imaging device may employ multi-spectrum monitoring to discriminate topography and underlying structures. A multi-spectral image is one that captures image data within specific wavelength ranges across the electromagnetic spectrum. The wavelengths may be separated by filters or by the use of instruments that are sensitive to particular wavelengths, including light from frequencies beyond the visible light range, e.g., IR and ultraviolet. Spectral imaging can allow extraction of additional information that the human eye fails to capture with its receptors for red, green, and blue. The use of multi-spectral imaging is described in greater detail under the heading "Advanced Imaging Acquisition Module" in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety. Multi-spectrum monitoring can be a useful tool in relocating a surgical field after a surgical task is completed to perform one or more of the previously described tests on the treated tissue. It is axiomatic that strict sterilization of the operating room and surgical equipment is required during any surgery. The strict hygiene and sterilization conditions required in a "surgical theater," i.e., an operating or treatment room, necessitate the highest possible sterility of all medical devices and equipment. Part of that sterilization process is the need to sterilize anything that comes in contact with the patient or penetrates the sterile field, including the imaging device 20030 and its attachments and components. It will be appreciated that the sterile field may be considered a specified area, such as within a tray or on a sterile towel, that is considered free of microorganisms, or the sterile field may be considered an area, immediately around a patient, who has been prepared for a surgical procedure. The sterile field may include the scrubbed team members, who are properly attired, and all furniture and fixtures in the area.

Wearable sensing system 20011 illustrated in FIG. 1 may include one or more sensing systems, for example, HCP sensing systems 20020 as shown in FIG. 2. The HCP sensing systems 20020 may include sensing systems to monitor and detect a set of physical states and/or a set of physiological states of a healthcare personnel (HCP). An HCP may be a surgeon or one or more healthcare personnel assisting the surgeon or other healthcare service providers in general. In an example, a sensing system 20020 may measure a set of biomarkers to monitor the heart rate of an HCP. In an example, a sensing system 20020 worn on a surgeon's wrist (e.g., a watch or a wristband) may use an accelerometer to detect hand motion and/or shakes and determine the magnitude and frequency of tremors. The sensing system 20020 may send the measurement data associated with the set of biomarkers and the data associated with a physical state of the surgeon to the surgical hub 20006 for further processing. One or more environmental sensing devices may send environmental information to the surgical hub 20006. For example, the environmental sensing devices may include a camera 20021 for detecting hand/body position of an HCP. The environmental sensing devices may include microphones 20022 for measuring the ambient noise in the surgical theater. Other environmental sensing devices may include devices, for example, a thermometer to measure temperature and a hygrometer to measure humidity of the surroundings in the surgical theater, etc. The surgical hub 20006, alone or in communication with the cloud computing system, may use the surgeon biomarker measurement data and/or environmental sensing information to modify the control algorithms of hand-held instruments or the averaging delay of a robotic interface, for example, to minimize tremors. In an example, the HCP sensing systems 20020 may measure one or more surgeon biomarkers associated with an HCP and send the measurement data associated with the surgeon biomarkers to the surgical hub 20006. The HCP sensing systems 20020 may use one or more of the following RF protocols for communicating with the surgical hub 20006: Bluetooth, Bluetooth Low-Energy (BLE), Bluetooth Smart, Zigbee, Z-wave, IPv6 Low-power wireless Personal Area Network (6LoWPAN), Wi-Fi. The surgeon biomarkers may include one or more of the following: stress, heart rate, etc. The environmental measurements from the surgical theater may include ambient noise level associated with the surgeon or the patient, surgeon and/or staff movements, surgeon and/or staff attention level, etc.

The surgical hub 20006 may use the surgeon biomarker measurement data associated with an HCP to adaptively control one or more surgical instruments 20031. For example, the surgical hub 20006 may send a control program to a surgical instrument 20031 to control its actuators to limit or compensate for fatigue and use of fine motor skills. The surgical hub 20006 may send the control program based on situational awareness and/or the context on impor-tance or criticality of a task. The control program may instruct the instrument to alter operation to provide more control when control is needed.

Figure 3:
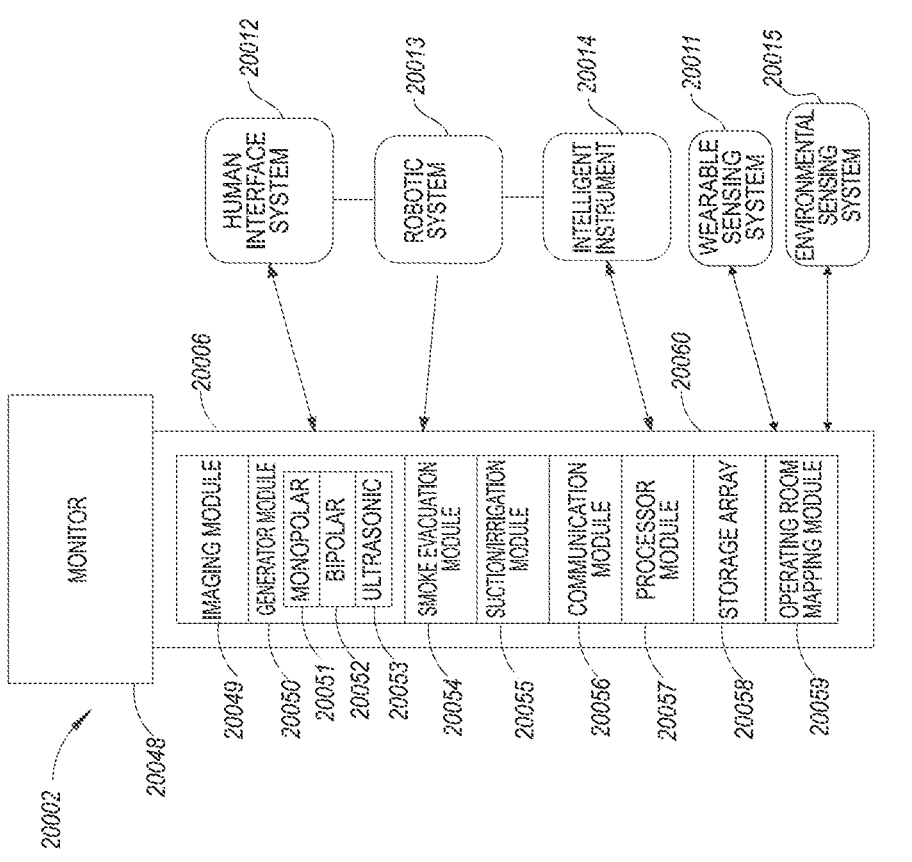
FIG. 3 illustrates an example surgical hub paired with various systems.

FIG. 3 shows an example HCP monitoring system 20002 with a surgical hub 20006 paired with a wearable sensing system 20011, an environmental sensing system 20015, a human interface system 20012, a robotic system 20013, and an intelligent instrument 20014. The hub 20006 includes a display 20048, an imaging module 20049, a generator module 20050, a communication module 20056, a processor module 20057, a storage array 20058, and an operating-room mapping module 20059. In certain aspects, as illus-trated in FIG. 3, the hub 20006 further includes a smoke evacuation module 20054 and/or a suction/irrigation module 20055. During a surgical procedure, energy application to tissue, for sealing and/or cutting, is generally associated with smoke evacuation, suction of excess fluid, and/or irrigation of the tissue. Fluid, power, and/or data lines from different sources are often entangled during the surgical procedure. Valuable time can be lost addressing this issue during a surgical procedure. Detangling the lines may necessitate disconnecting the lines from their respective modules, which may require resetting the modules. The hub modular enclo-sure 20060 offers a unified environment for managing the power, data, and fluid lines, which reduces the frequency of entanglement between such lines. Aspects of the present disclosure present a surgical hub 20006 for use in a surgical procedure that involves energy application to tissue at a surgical site. The surgical hub 20006 includes a hub enclo-sure 20060 and a combo generator module slidably receiv-able in a docking station of the hub enclosure 20060. The docking station includes data and power contacts. The combo generator module includes two or more of an ultra-sonic energy generator component, a bipolar RF energy generator component, and a monopolar RF energy generator component that are housed in a single unit. In one aspect, the combo generator module also includes a smoke evacuation component, at least one energy delivery cable for connecting the combo generator module to a surgical instrument, at least one smoke evacuation component configured to evacuate smoke, fluid, and/or particulates generated by the applica-tion of therapeutic energy to the tissue, and a fluid line extending from the remote surgical site to the smoke evacu-ation component. In one aspect, the fluid line may be a first fluid line, and a second fluid line may extend from the remote surgical site to a suction and irrigation module 20055 slidably received in the hub enclosure 20060. In one aspect, the hub enclosure 20060 may include a fluid interface. Certain surgical procedures may require the application of more than one energy type to the tissue. One energy type may be more beneficial for cutting the tissue, while another different energy type may be more beneficial for sealing the tissue. For example, a bipolar generator can be used to seal the tissue while an ultrasonic generator can be used to cut the sealed tissue. Aspects of the present disclosure present a solution where a hub modular enclosure 20060 is configured to accommodate different generators and facilitate an inter-active communication therebetween. One of the advantages of the hub modular enclosure 20060 is enabling the quick removal and/or replacement of various modules. Aspects of the present disclosure present a modular surgical enclosure for use in a surgical procedure that involves energy appli-cation to tissue. The modular surgical enclosure includes a first energy-generator module, configured to generate a first energy for application to the tissue, and a first docking station comprising a first docking port that includes first data and power contacts, wherein the first energy-generator mod-ule is slidably movable into an electrical engagement with the power and data contacts and wherein the first energy-generator module is slidably movable out of the electrical engagement with the first power and data contacts. Further to the above, the modular surgical enclosure also includes a second energy-generator module configured to generate a second energy, different than the first energy, for application to the tissue, and a second docking station comprising a second docking port that includes second data and power contacts, wherein the second energy generator module is slidably movable into an electrical engagement with the power and data contacts, and wherein the second energy-generator module is slidably movable out of the electrical engagement with the second power and data contacts. In addition, the modular surgical enclosure also includes a communication bus between the first docking port and the second docking port, configured to facilitate communication between the first energy-generator module and the second energy-generator module. Referring to FIG. 3, aspects of the present disclosure are presented for a hub modular enclosure 20060 that allows the modular integration of a generator module 20050, a smoke evacuation module 20054, and a suction/irrigation module 20055. The hub modular enclo-sure 20060 further facilitates interactive communication between the modules 20059, 20054, and 20055. The gen-erator module 20050 can be a generator module 20050 with integrated monopolar, bipolar, and ultrasonic components supported in a single housing unit slidably insertable into the hub modular enclosure 20060. The generator module 20050 can be configured to connect to a monopolar device 20051, a bipolar device 20052, and an ultrasonic device 20053. Alternatively, the generator module 20050 may comprise a series of monopolar, bipolar, and/or ultrasonic generator modules that interact through the hub modular enclosure 20060. The hub modular enclosure 20060 can be configured to facilitate the insertion of multiple generators and inter-active communication between the generators docked into the hub modular enclosure 20060 so that the generators would act as a single generator.

Figure 4:
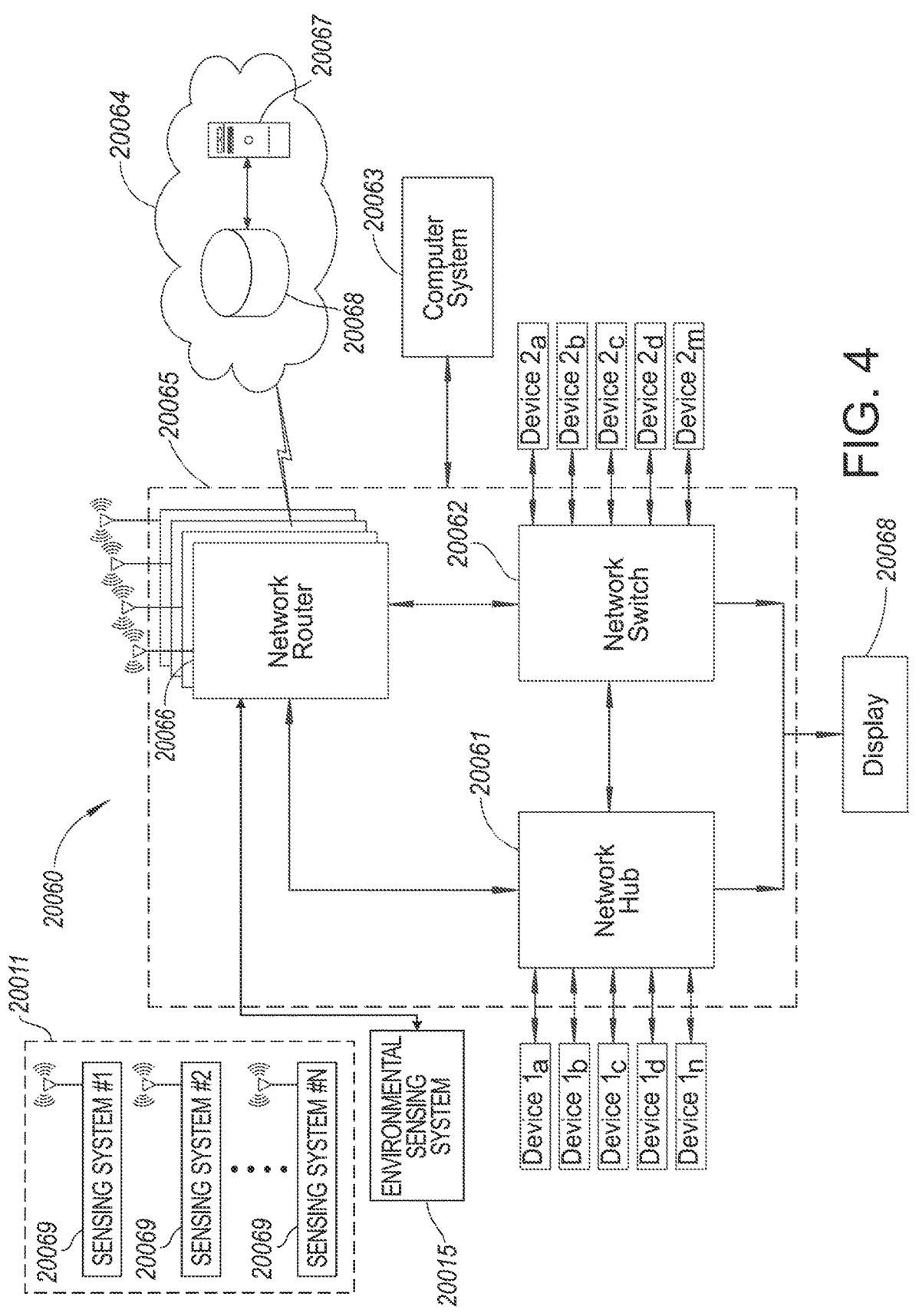
FIG. 4 illustrates a surgical data network having a set of communication surgical hubs configured to connect with a set of sensing systems, an environmental sensing system, a set of devices, etc.

FIG. 4 illustrates a surgical data network having a set of communication hubs configured to connect a set of sensing systems, environment sensing system(s), and a set of other modular devices located in one or more operating theaters of a healthcare facility, a patient recovery room, or a room in a healthcare facility specially equipped for surgical opera-tions, to the cloud, in accordance with at least one aspect of the present disclosure.

As illustrated in FIG. 4, a surgical hub system 20060 may include a modular communication hub 20065 that is con-figured to connect modular devices located in a healthcare facility to a cloud-based system (e.g., a cloud computing system 20064 that may include a remote server 20067 coupled to a remote storage 20068). The modular commu-nication hub 20065 and the devices may be connected in a room in a healthcare facility specially equipped for surgical operations. In one aspect, the modular communication hub 20065 may include a network hub 20061 and/or a network switch 20062 in communication with a network router 20066. The modular communication hub 20065 may be coupled to a local computer system 20063 to provide local computer processing and data manipulation.

The computer system 20063 may comprise a processor and a network interface 20100. The processor may be coupled to a communication module, storage, memory, non-volatile memory, and input/output (I/O) interface via a system bus. The system bus can be any of several types of bus structure(s) including the memory bus or memory controller, a peripheral bus or external bus, and or a local bus using any variety of available bus architectures including, but not limited to, 9-bit bus, Industrial Standard Architecture (ISA), Micro-Charmel Architecture (MSA), Extended ISA (EISA), Intelligent Drive Electronics (IDE), VESA Local Bus (VLB), Peripheral Component Interconnect (PCI), USB, Advanced Graphics Port (AGP), Personal Computer Memory Card International Association bus (PCMCIA), Small Computer Systems Interface (SCSI), or any other proprietary bus.

The processor may be any single-core or multicore processor such as those known under the trade name ARM Cortex by Texas Instruments. In one aspect, the processor may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle serial random access memory (SRAM), an internal read-only memory (ROM) loaded with Stellaris Ware® software, a 2 KB electrically erasable programmable read-only memory (EEPROM), and/or one or more pulse width modulation (PWM) modules, one or more quadrature encoder inputs (QEI) analogs, one or more 12-bit analog-to-digital converters (ADCs) with 12 analog input channels, details of which are available for the product datasheet.

In an example, the processor may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

It is to be appreciated that the computer system 20063 may include software that acts as an intermediary between users and the basic computer resources described in a suitable operating environment. Such software may include an operating system. The operating system, which can be stored on the disk storage, may act to control and allocate resources of the computer system. System applications may take advantage of the management of resources by the operating system through program modules and program data stored either in the system memory or on the disk storage. It is to be appreciated that various components described herein can be implemented with various operating systems or combinations of operating systems.

A user may enter commands or information into the computer system 20063 through input device(s) coupled to the I/O interface. The input devices may include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processor 20102 through the system bus via interface port(s). The interface port(s) include, for example, a serial port, a parallel port, a game port, and a USB. The output device(s) use some of the same types of ports as input device(s). Thus, for example, a USB port may be used to provide input to the computer system 20063 and to output information from the computer system 20063 to an output device. An output adapter may be provided to illustrate that there can be some output devices like monitors, displays, speakers, and printers, among other output devices that may require special adapters. The output adapters may include, by way of illustration and not limitation, video and sound cards that provide a means of connection between the output device and the system bus. It should be noted that other devices and/or systems of devices, such as remote computer(s), may provide both input and output capabilities.

The computer system 20063 can operate in a networked environment using logical connections to one or more remote computers, such as cloud computer(s), or local computers. The remote cloud computer(s) can be a personal computer, server, router, network PC, workstation, microprocessor-based appliance, peer device, or other common network node, and the like, and typically includes many or all of the elements described relative to the computer system. For purposes of brevity, only a memory storage device is illustrated with the remote computer(s). The remote computer(s) may be logically connected to the computer system through a network interface and then physically connected via a communication connection. The network interface may encompass communication networks such as local area networks (LANs) and wide area networks (WANs). LAN technologies may include Fiber Distributed Data Interface (FDDI), Copper Distributed Data Interface (CDDI), Ethernet/IEEE 802.3, Token Ring/IEEE 802.5, and the like. WAN technologies may include, but are not limited to, point-to-point links, circuit-switching networks like Integrated Services Digital Networks (ISDN) and variations thereon, packet-switching networks, and Digital Subscriber Lines (DSL).

In various examples, the computer system 20063 may comprise an image processor, image-processing engine, media processor, or any specialized digital signal processor (DSP) used for the processing of digital images. The image processor may employ parallel computing with single instruction, multiple data (SIMD) or multiple instruction, multiple data (MIMD) technologies to increase speed and efficiency. The digital image-processing engine can perform a range of tasks. The image processor may be a system on a chip with multicore processor architecture.

The communication connection(s) may refer to the hardware/software employed to connect the network interface to the bus. While the communication connection is shown for illustrative clarity inside the computer system 20063, it can also be external to the computer system 20063. The hardware/software necessary for connection to the network interface may include, for illustrative purposes only, internal and external technologies such as modems, including regular telephone-grade modems, cable modems, optical fiber modems, and DSL modems, ISDN adapters, and Ethernet cards. In some examples, the network interface may also be provided using an RF interface.

Surgical data network associated with the surgical hub system 20060 may be configured as passive, intelligent, or switching. A passive surgical data network serves as a conduit for the data, enabling it to go from one device (or segment) to another and to the cloud computing resources. An intelligent surgical data network includes additional features to enable the traffic passing through the surgical data network to be monitored and to configure each port in the network hub 20061 or network switch 20062. An intelligent surgical data network may be referred to as a manageable hub or switch. A switching hub reads the destination address of each packet and then forwards the packet to the correct port.

Modular devices 1a-1n located in the operating theater may be coupled to the modular communication hub 20065. The network hub 20061 and/or the network switch 20062 may be coupled to a network router 20066 to connect the devices 1a-1n to the cloud computing system 20064 or the local computer system 20063. Data associated with the devices 1a-1n may be transferred to cloud-based computers via the router for remote data processing and manipulation. Data associated with the devices 1a-1n may also be transferred to the local computer system 20063 for local data processing and manipulation. Modular devices 2a-2m located in the same operating theater also may be coupled to a network switch 20062. The network switch 20062 may be coupled to the network hub 20061 and/or the network router 20066 to connect the devices 2a-2m to the cloud 20064. Data associated with the devices 2a-2m may be transferred to the cloud computing system 20064 via the network router 20066 for data processing and manipulation. Data associated with the devices 2a-2m may also be transferred to the local computer system 20063 for local data processing and manipulation.

The wearable sensing system 20011 may include one or more sensing systems 20069. The sensing systems 20069 may include an HCP sensing system and/or a patient sensing system. The one or more sensing systems 20069 may be in communication with the computer system 20063 of a surgical hub system 20060 or the cloud server 20067 directly via one of the network routers 20066 or via a network hub 20061 or network switching 20062 that is in communication with the network routers 20066.

The sensing systems 20069 may be coupled to the network router 20066 to connect to the sensing systems 20069 to the local computer system 20063 and/or the cloud computing system 20064. Data associated with the sensing systems 20069 may be transferred to the cloud computing system 20064 via the network router 20066 for data processing and manipulation. Data associated with the sensing systems 20069 may also be transferred to the local computer system 20063 for local data processing and manipulation.

As illustrated in FIG. 4, the surgical hub system 20060 may be expanded by interconnecting multiple network hubs 20061 and/or multiple network switches 20062 with multiple network routers 20066. The modular communication hub 20065 may be contained in a modular control tower configured to receive multiple devices 1a-1n/2a-2m. The local computer system 20063 also may be contained in a modular control tower. The modular communication hub 20065 may be connected to a display 20068 to display images obtained by some of the devices 1a-1n/2a-2m, for example during surgical procedures. In various aspects, the devices 1a-1n/2a-2m may include, for example, various modules such as an imaging module coupled to an endoscope, a generator module coupled to an energy-based surgical device, a smoke evacuation module, a suction/irrigation module, a communication module, a processor module, a storage array, a surgical device coupled to a display, and/or a non-contact sensor module, among other modular devices that may be connected to the modular communication hub 20065 of the surgical data network.

In one aspect, the surgical hub system 20060 illustrated in FIG. 4 may comprise a combination of network hub(s), network switch(es), and network router(s) connecting the devices 1a-1n/2a-2m or the sensing systems 20069 to the cloud-base system 20064. One or more of the devices 1a-1n/2a-2m or the sensing systems 20069 coupled to the network hub 20061 or network switch 20062 may collect data or measurement data in real-time and transfer the data to cloud computers for data processing and manipulation. It will be appreciated that cloud computing relies on sharing computing resources rather than having local servers or personal devices to handle software applications. The word "cloud" may be used as a metaphor for "the Internet," although the term is not limited as such. Accordingly, the term "cloud computing" may be used herein to refer to "a type of Internet-based computing," where different services—such as servers, storage, and applications—are delivered to the modular communication hub 20065 and/or computer system 20063 located in the surgical theater (e.g., a fixed, mobile, temporary, or field operating room or space) and to devices connected to the modular communication hub 20065 and/or computer system 20063 through the Internet. The cloud infrastructure may be maintained by a cloud service provider. In this context, the cloud service provider may be the entity that coordinates the usage and control of the devices 1a-1n/2a-2m located in one or more operating theaters. The cloud computing services can perform a large number of calculations based on the data gathered by smart surgical instruments, robots, sensing systems, and other computerized devices located in the operating theater. The hub hardware enables multiple devices, sensing systems, and/or connections to be connected to a computer that communicates with the cloud computing resources and storage.

Applying cloud computer data processing techniques on the data collected by the devices 1a-1n/2a-2m, the surgical data network can provide improved surgical outcomes, reduced costs, and improved patient satisfaction. At least some of the devices 1a-1n/2a-2m may be employed to view tissue states to assess leaks or perfusion of sealed tissue after a tissue sealing and cutting procedure. At least some of the devices 1a-1n/2a-2m may be employed to identify pathology, such as the effects of diseases, using the cloud-based computing to examine data including images of samples of body tissue for diagnostic purposes. This may include localization and margin confirmation of tissue and phenotypes. At least some of the devices 1a-1n/2a-2m may be employed to identify anatomical structures of the body using a variety of sensors integrated with imaging devices and techniques such as overlaying images captured by multiple imaging devices. The data gathered by the devices 1a-1n/2a-2m, including image data, may be transferred to the cloud computing system 20064 or the local computer system 20063 or both for data processing and manipulation including image processing and manipulation. The data may be analyzed to improve surgical procedure outcomes by determining if further treatment, such as the application of endoscopic intervention, emerging technologies, a targeted radiation, targeted intervention, and precise robotics to tissue-specific sites and conditions, may be pursued. Such data analysis may further employ outcome analytics processing and using standardized approaches may provide beneficial feedback to either confirm surgical treatments and the behavior of the surgeon or suggest modifications to surgical treatments and the behavior of the surgeon.

Applying cloud computer data processing techniques on the measurement data collected by the sensing systems 20069, the surgical data network can provide improved surgical outcomes, improved recovery outcomes, reduced costs, and improved patient satisfaction. At least some of the sensing systems 20069 may be employed to assess physiological conditions of a surgeon operating on a patient or a patient being prepared for a surgical procedure or a patient recovering after a surgical procedure. The cloud-based computing system 20064 may be used to monitor biomarkers associated with a surgeon or a patient in real-time and to generate surgical plans based at least on measurement data gathered prior to a surgical procedure, provide control signals to the surgical instruments during a surgical procedure, notify a patient of a complication during post-surgical period.

The operating theater devices 1a-1n may be connected to the modular communication hub 20065 over a wired channel or a wireless channel depending on the configuration of the devices 1a-1n to a network hub 20061. The network hub 20061 may be implemented, in one aspect, as a local network broadcast device that works on the physical layer of the Open System Interconnection (OSI) model. The network hub may provide connectivity to the devices 1a-1n located in the same operating theater network. The network hub 20061 may collect data in the form of packets and sends them to the router in half duplex mode. The network hub 20061 may not store any media access control/Internet Protocol (MAC/IP) to transfer the device data. Only one of the devices 1a-In can send data at a time through the network hub 20061. The network hub 20061 may not have routing tables or intelligence regarding where to send information and broadcasts all network data across each connection and to a remote server 20067 of the cloud computing system 20064. The network hub 20061 can detect basic network errors such as collisions but having all information broadcast to multiple ports can be a security risk and cause bottlenecks.

The operating theater devices 2a-2m may be connected to a network switch 20062 over a wired channel or a wireless channel. The network switch 20062 works in the data link layer of the OSI model. The network switch 20062 may be a multicast device for connecting the devices 2a-2m located in the same operating theater to the network. The network switch 20062 may send data in the form of frames to the network router 20066 and may work in full duplex mode. Multiple devices 2a-2m can send data at the same time through the network switch 20062. The network switch 20062 stores and uses MAC addresses of the devices 2a-2m to transfer data.

The network hub 20061 and/or the network switch 20062 may be coupled to the network router 20066 for connection to the cloud computing system 20064. The network router 20066 works in the network layer of the OSI model. The network router 20066 creates a route for transmitting data packets received from the network hub 20061 and/or network switch 20062 to cloud-based computer resources for further processing and manipulation of the data collected by any one of or all the devices 1a-1n/2a-2m and wearable sensing system 20011. The network router 20066 may be employed to connect two or more different networks located in different locations, such as, for example, different operating theaters of the same healthcare facility or different networks located in different operating theaters of different healthcare facilities. The network router 20066 may send data in the form of packets to the cloud computing system 20064 and works in full duplex mode. Multiple devices can send data at the same time. The network router 20066 may use IP addresses to transfer data.

In an example, the network hub 20061 may be implemented as a USB hub, which allows multiple USB devices to be connected to a host computer. The USB hub may expand a single USB port into several tiers so that there are more ports available to connect devices to the host system computer. The network hub 20061 may include wired or wireless capabilities to receive information over a wired channel or a wireless channel. In one aspect, a wireless USB short-range, high-bandwidth wireless radio communication protocol may be employed for communication between the devices 1a-1n and devices 2a-2m located in the operating theater.

In examples, the operating theater devices 1a-1n/2a-2m and/or the sensing systems 20069 may communicate to the modular communication hub 20065 via Bluetooth wireless technology standard for exchanging data over short distances (using short-wavelength UHF radio waves in the ISM band from 2.4 to 2.485 GHZ) from fixed and mobile devices and building personal area networks (PANs). The operating theater devices 1a-1n/2a-2m and/or the sensing systems 20069 may communicate to the modular communication hub 20065 via a number of wireless or wired communication standards or protocols, including but not limited to Bluetooth, Low-Energy Bluetooth, near-field communication (NFC), Wi-Fi (IEEE 802.11 family), WiMAX (IEEE 802.16 family), IEEE 802.20, new radio (NR), long-term evolution (LTE), and Ev-DO, HSPA+, HSDPA+, HSUPA+, EDGE, GSM, GPRS, CDMA, TDMA, DECT, and Ethernet derivatives thereof, as well as any other wireless and wired protocols that are designated as 3G, 4G, 5G, and beyond. The computing module may include a plurality of communication modules. For instance, a first communication module may be dedicated to shorter-range wireless communications such as Wi-Fi and Bluetooth Low-Energy Bluetooth, Bluetooth Smart, and a second communication module may be dedicated to longer-range wireless communications such as GPS, EDGE, GPRS, CDMA, WIMAX, LTE, Ev-DO, HSPA+, HSDPA+, HSUPA+, EDGE, GSM, GPRS, CDMA, TDMA, and others.

The modular communication hub 20065 may serve as a central connection for one or more of the operating theater devices 1a-1n/2a-2m and/or the sensing systems 20069 and may handle a data type known as frames. Frames may carry the data generated by the devices 1a-1n/2a-2m and/or the sensing systems 20069. When a frame is received by the modular communication hub 20065, it may be amplified and/or sent to the network router 20066, which may transfer the data to the cloud computing system 20064 or the local computer system 20063 by using a number of wireless or wired communication standards or protocols, as described herein.

The modular communication hub 20065 can be used as a standalone device or be connected to compatible network hubs 20061 and network switches 20062 to form a larger network. The modular communication hub 20065 can be generally easy to install, configure, and maintain, making it a good option for networking the operating theater devices 1a-1n/2a-2m.

Figure 5:
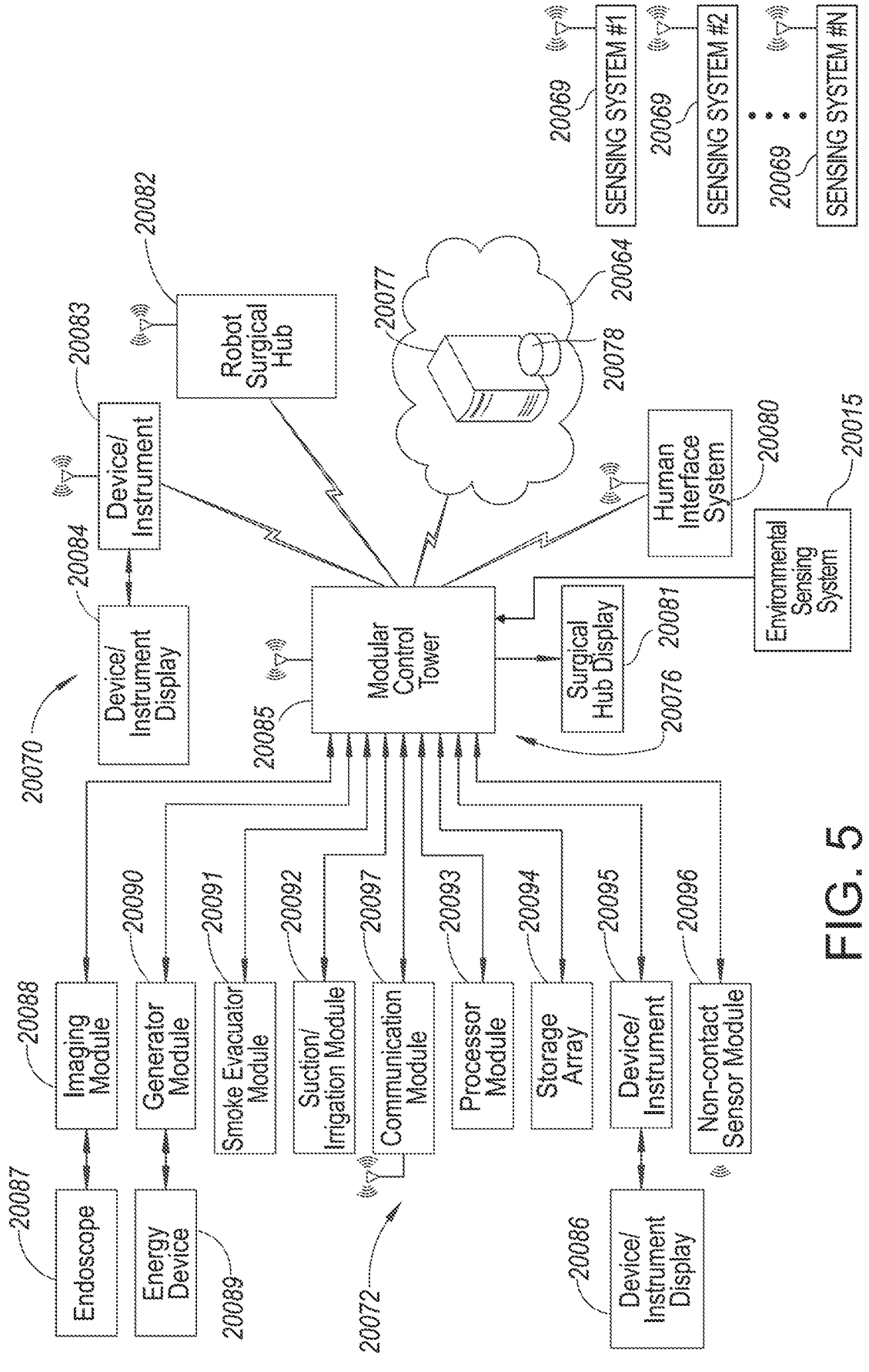
FIG. 5 illustrates an example computer-implemented interactive surgical system that may be part of an HCP monitoring system.

FIG. 5 illustrates a computer-implemented interactive surgical system 20070 that may be a part of the HCP monitoring system 20002. The computer-implemented interactive surgical system 20070 is similar in many respects to the HCP sensing system 20002. For example, the computer-implemented interactive surgical system 20070 may include one or more surgical sub-systems 20072, which are similar in many respects to the HCP monitoring systems 20002. Each sub-surgical system 20072 may include at least one surgical hub 20076 in communication with a cloud computing system 20064 that may include a remote server 20077 and a remote storage 20078. In one aspect, the computer-implemented interactive surgical system 20070 may include a modular control tower 20085 connected to multiple operating theater devices such as sensing systems 20001, intelligent surgical instruments, robots, and other computerized devices located in the operating theater.

As illustrated in the example of FIG. 5, the modular control tower 20085 may be coupled to an imaging module 20088 that may be coupled to an endoscope 20087, a generator module 20090 that may be coupled to an energy device 20089, a smoke evacuator module 20091, a suction/ irrigation module 20092, a communication module 20097, a processor module 20093, a storage array 20094, a smart device/instrument 20095 optionally coupled to a display 20086 and 20084 respectively, and a non-contact sensor module 20096. The non-contact sensor module 20096 may measure the dimensions of the operating theater and generate a map of the surgical theater using, ultrasonic, laser-type, and/or the like, non-contact measurement devices. Other distance sensors can be employed to determine the bounds of an operating room. An ultrasound-based non-contact sensor module may scan the operating theater by transmitting a burst of ultrasound and receiving the echo when it bounces off the perimeter walls of an operating theater as described under the heading "Surgical Hub Spatial Awareness Within an Operating Room" in U.S. Provisional Patent Application Ser. No. 62/611,341, titled INTERACTIVE SURGICAL PLATFORM, filed Dec. 28, 2017, which is herein incorporated by reference in its entirety. The sensor module may be configured to determine the size of the operating theater and to adjust Bluetooth-pairing distance limits. A laser-based non-contact sensor module may scan the operating theater by transmitting laser light pulses, receiving laser light pulses that bounce off the perimeter walls of the operating theater, and comparing the phase of the transmitted pulse to the received pulse to determine the size of the operating theater and to adjust Bluetooth pairing distance limits, for example.

The modular control tower 20085 may also be in communication with one or more sensing systems 20069 and an environmental sensing system 20015. The sensing systems 20069 may be connected to the modular control tower 20085 either directly via a router or via the communication module 20097. The operating theater devices may be coupled to cloud computing resources and data storage via the modular control tower 20085. A robot surgical hub 20082 also may be connected to the modular control tower 20085 and to the cloud computing resources. The devices/instruments 20095 or 20084, human interface system 20080, among others, may be coupled to the modular control tower 20085 via wired or wireless communication standards or protocols, as described herein. The human interface system 20080 may include a display sub-system and a notification sub-system. The modular control tower 20085 may be coupled to a hub display 20081 (e.g., monitor, screen) to display and overlay images received from the imaging module 20088, device/ instrument display 20086, and/or other human interface systems 20080. The hub display 20081 also may display data received from devices connected to the modular control tower 20085 in conjunction with images and overlaid images.

Figure 6:
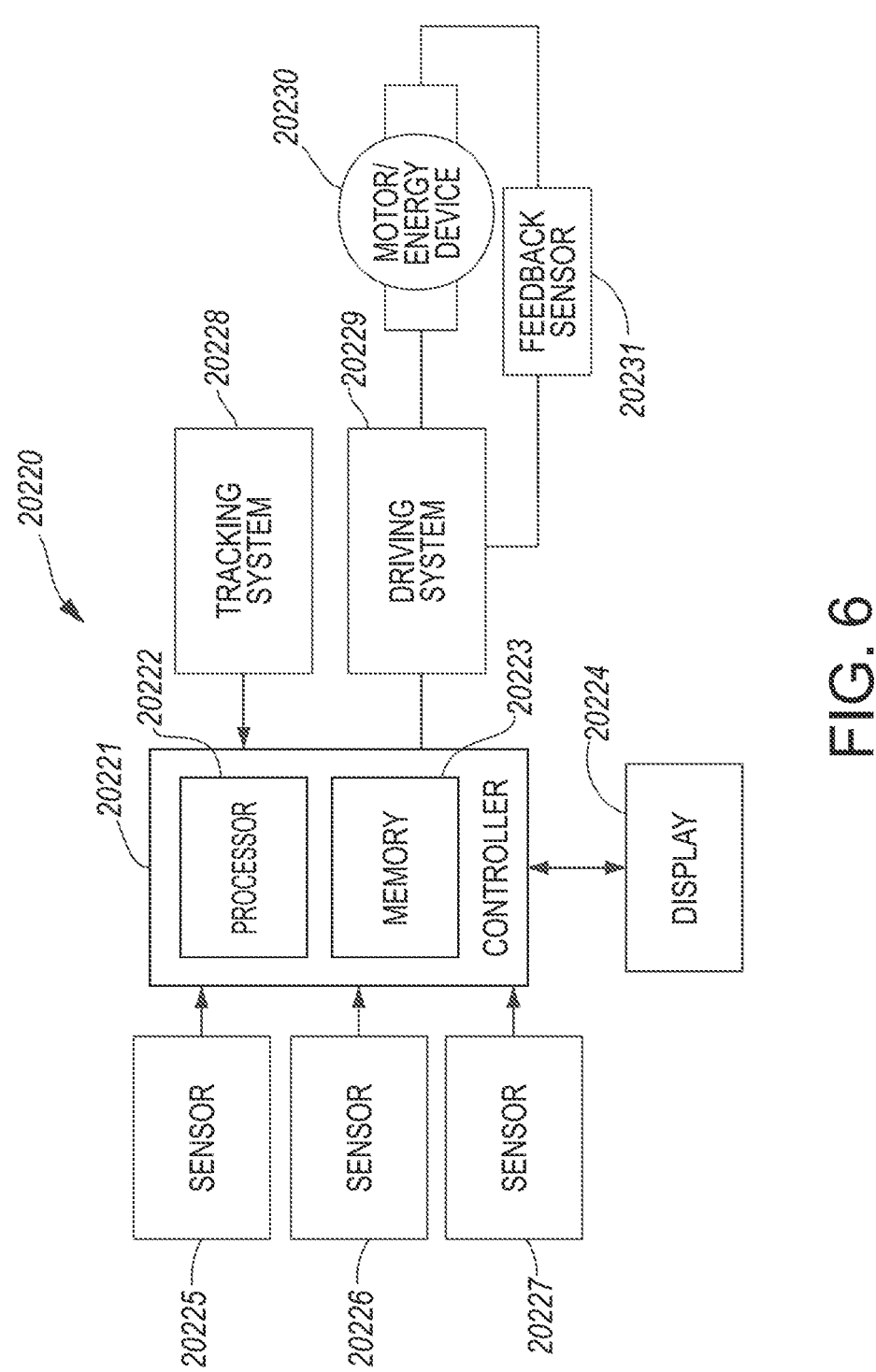
FIG. 6 illustrates a logic diagram of a control system of a surgical instrument.

FIG. 6 illustrates a logical diagram of a control system 20220 of a surgical instrument or a surgical tool in accordance with one or more aspects of the present disclosure. The surgical instrument or the surgical tool may be configurable. The surgical instrument may include surgical fixtures specific to the procedure at-hand, such as imaging devices, surgical staplers, energy devices, endocutter devices, or the like. For example, the surgical instrument may include any of a powered stapler, a powered stapler generator, an energy device, an advanced energy device, an advanced energy jaw device, an endocutter clamp, an energy device generator, an in-operating-room imaging system, a smoke evacuator, a suction-irrigation device, an insufflation system, or the like. The system 20220 may comprise a control circuit. The control circuit may include a microcontroller 20221 comprising a processor 20222 and a memory 20223. One or more of sensors 20225, 20226, 20227, for example, provide real-time feedback to the processor 20222. A motor 20230, driven by a motor driver 20229, operably couples a longitudinally movable displacement member to drive the I-beam knife element. A tracking system 20228 may be configured to determine the position of the longitudinally movable displacement member. The position information may be provided to the processor 20222, which can be programmed or configured to determine the position of the longitudinally movable drive member as well as the position of a firing member, firing bar, and I-beam knife element. Additional motors may be provided at the tool driver interface to control I-beam firing, closure tube travel, shaft rotation, and articulation. A display 20224 may display a variety of operating conditions of the instruments and may include touch screen functionality for data input. Information displayed on the display 20224 may be overlaid with images acquired via endoscopic imaging modules.

The microcontroller 20221 may be any single-core or multicore processor such as those known under the trade name ARM Cortex by Texas Instruments. In one aspect, the main microcontroller 20221 may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle SRAM, and internal ROM loaded with Stellaris Ware® software, a 2 KB EEPROM, one or more PWM modules, one or more QEI analogs, and/or one or more 12-bit ADCs with 12 analog input channels, details of which are available for the product datasheet.

The microcontroller 20221 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The microcontroller 20221 may be programmed to perform various functions such as precise control over the speed and position of the knife and articulation systems. In one aspect, the microcontroller 20221 may include a processor 20222 and a memory 20223. The electric motor 20230 may be a brushed direct current (DC) motor with a gearbox and mechanical links to an articulation or knife system. In one aspect, a motor driver 20229 may be an A3941 available from Allegro Microsystems, Inc. Other motor drivers may be readily substituted for use in the tracking system 20228 comprising an absolute positioning system. A detailed description of an absolute positioning system is described in U.S. Patent Application Publication No. 2017/0296213, titled SYSTEMS AND METHODS FOR CONTROLLING A SURGICAL STAPLING AND CUTTING INSTRUMENT, which published on Oct. 19, 2017, which is herein incorporated by reference in its entirety.

The microcontroller 20221 may be programmed to provide precise control over the speed and position of displacement members and articulation systems. The microcontroller 20221 may be configured to compute a response in the software of the microcontroller 20221. The computed response may be compared to a measured response of the actual system to obtain an "observed" response, which is used for actual feedback decisions. The observed response may be a favorable, tuned value that balances the smooth, continuous nature of the simulated response with the measured response, which can detect outside influences on the system.

The motor 20230 may be controlled by the motor driver 20229 and can be employed by the firing system of the surgical instrument or tool. In various forms, the motor 20230 may be a brushed DC driving motor having a maximum rotational speed of approximately 25,000 RPM. In some examples, the motor 20230 may include a brushless motor, a cordless motor, a synchronous motor, a stepper motor, or any other suitable electric motor. The motor driver 20229 may comprise an H-bridge driver comprising field-effect transistors (FETs), for example. The motor 20230 can be powered by a power assembly releasably mounted to the handle assembly or tool housing for supplying control power to the surgical instrument or tool. The power assembly may comprise a battery which may include a number of battery cells connected in series that can be used as the power source to power the surgical instrument or tool. In certain circumstances, the battery cells of the power assembly may be replaceable and/or rechargeable. In at least one example, the battery cells can be lithium-ion batteries which can be couplable to and separable from the power assembly.

The motor driver 20229 may be an A3941 available from Allegro Microsystems, Inc. A3941 may be a full-bridge controller for use with external N-channel power metal-oxide semiconductor field-effect transistors (MOSFETs) specifically designed for inductive loads, such as brush DC motors. The driver 20229 may comprise a unique charge pump regulator that can provide full (>10 V) gate drive for battery voltages down to 7 V and can allow the A3941 to operate with a reduced gate drive, down to 5.5 V. A bootstrap capacitor may be employed to provide the above battery supply voltage required for N-channel MOSFETs. An internal charge pump for the high-side drive may allow DC (100% duty cycle) operation. The full bridge can be driven in fast or slow decay modes using diode or synchronous rectification. In the slow decay mode, current recirculation can be through the high-side or the low-side FETs. The power FETs may be protected from shoot-through by resistor-adjustable dead time. Integrated diagnostics provide indications of undervoltage, overtemperature, and power bridge faults and can be configured to protect the power MOSFETs under most short circuit conditions. Other motor drivers may be readily substituted for use in the tracking system 20228 comprising an absolute positioning system.

The tracking system 20228 may comprise a controlled motor drive circuit arrangement comprising a position sensor 20225 according to one aspect of this disclosure. The position sensor 20225 for an absolute positioning system may provide a unique position signal corresponding to the location of a displacement member. In some examples, the displacement member may represent a longitudinally movable drive member comprising a rack of drive teeth for meshing engagement with a corresponding drive gear of a gear reducer assembly. In some examples, the displacement member may represent the firing member, which could be adapted and configured to include a rack of drive teeth. In some examples, the displacement member may represent a firing bar or the I-beam, each of which can be adapted and configured to include a rack of drive teeth. Accordingly, as used herein, the term displacement member can be used generically to refer to any movable member of the surgical instrument or tool such as the drive member, the firing member, the firing bar, the I-beam, or any element that can be displaced. In one aspect, the longitudinally movable drive member can be coupled to the firing member, the firing bar, and the I-beam. Accordingly, the absolute positioning system can, in effect, track the linear displacement of the I-beam by tracking the linear displacement of the longitudinally movable drive member. In various aspects, the displacement member may be coupled to any position sensor 20225 suitable for measuring linear displacement. Thus, the longitudinally movable drive member, the firing member, the firing bar, or the I-beam, or combinations thereof, may be coupled to any suitable linear displacement sensor. Linear displacement sensors may include contact or non-contact displacement sensors. Linear displacement sensors may comprise linear variable differential transformers (LVDT), differential variable reluctance transducers (DVRT), a slide potentiometer, a magnetic sensing system comprising a movable magnet and a series of linearly arranged Hall effect sensors, a magnetic sensing system comprising a fixed magnet and a series of movable, linearly arranged Hall effect sensors, an optical sensing system comprising a movable light source and a series of linearly arranged photo diodes or photo detectors, an optical sensing system comprising a fixed light source and a series of movable linearly, arranged photodiodes or photodetectors, or any combination thereof.

The electric motor 20230 can include a rotatable shaft that operably interfaces with a gear assembly that is mounted in meshing engagement with a set, or rack, of drive teeth on the displacement member. A sensor element may be operably coupled to a gear assembly such that a single revolution of the position sensor 20225 element corresponds to some linear longitudinal translation of the displacement member. An arrangement of gearing and sensors can be connected to the linear actuator, via a rack and pinion arrangement, or a rotary actuator, via a spur gear or other connection. A power source may supply power to the absolute positioning system and an output indicator may display the output of the absolute positioning system. The displacement member may represent the longitudinally movable drive member comprising a rack of drive teeth formed thereon for meshing engagement with a corresponding drive gear of the gear reducer assembly. The displacement member may represent the longitudinally movable firing member, firing bar, I-beam, or combinations thereof.

A single revolution of the sensor element associated with the position sensor 20225 may be equivalent to a longitudinal linear displacement d1 of the of the displacement member, where d1 is the longitudinal linear distance that the displacement member moves from point "a" to point "b" after a single revolution of the sensor element coupled to the displacement member. The sensor arrangement may be connected via a gear reduction that results in the position sensor 20225 completing one or more revolutions for the full stroke of the displacement member. The position sensor 20225 may complete multiple revolutions for the full stroke of the displacement member.

A series of switches, where n is an integer greater than one, may be employed alone or in combination with a gear reduction to provide a unique position signal for more than one revolution of the position sensor 20225. The state of the switches may be fed back to the microcontroller 20221 that applies logic to determine a unique position signal corresponding to the longitudinal linear displacement d1+d2+ . . . dn of the displacement member. The output of the position sensor 20225 is provided to the microcontroller 20221. The position sensor 20225 of the sensor arrangement may comprise a magnetic sensor, an analog rotary sensor like a potentiometer, or an array of analog Hall-effect elements, which output a unique combination of position signals or values.

The position sensor 20225 may comprise any number of magnetic sensing elements, such as, for example, magnetic sensors classified according to whether they measure the total magnetic field or the vector components of the magnetic field. The techniques used to produce both types of magnetic sensors may encompass many aspects of physics and electronics. The technologies used for magnetic field sensing may include search coil, fluxgate, optically pumped, nuclear precession, SQUID, Hall-effect, anisotropic magnetoresistance, giant magnetoresistance, magnetic tunnel junctions, giant magnetoimpedance, magnetostrictive/piezoelectric composites, magnetodiode, magnetotransistor, fiber-optic, magneto-optic, and microelectromechanical systems-based magnetic sensors, among others.

The position sensor 20225 for the tracking system 20228 comprising an absolute positioning system may comprise a magnetic rotary absolute positioning system. The position sensor 20225 may be implemented as an AS5055EQFT single-chip magnetic rotary position sensor available from Austria Microsystems, AG. The position sensor 20225 is interfaced with the microcontroller 20221 to provide an absolute positioning system. The position sensor 20225 may be a low-voltage and low-power component and may include four Hall-effect elements in an area of the position sensor 20225 that may be located above a magnet. A high-resolution ADC and a smart power management controller may also be provided on the chip. A coordinate rotation digital computer (CORDIC) processor, also known as the digit-by-digit method and Volder's algorithm, may be provided to implement a simple and efficient algorithm to calculate hyperbolic and trigonometric functions that require only addition, subtraction, bit-shift, and table lookup operations. The angle position, alarm bits, and magnetic field information may be transmitted over a standard serial communication interface, such as a serial peripheral interface (SPI) interface, to the microcontroller 20221. The position sensor 20225 may provide 12 or 14 bits of resolution. The position sensor 20225 may be an AS5055 chip provided in a small QFN 16-pin 4×4×0.85 mm package.

The tracking system 20228 comprising an absolute positioning system may comprise and/or be programmed to implement a feedback controller, such as a PID, state feedback, and adaptive controller. A power source converts the signal from the feedback controller into a physical input to the system: in this case the voltage. Other examples include a PWM of the voltage, current, and force. Other sensor(s) may be provided to measure physical parameters of the physical system in addition to the position measured by the position sensor 20225. In some aspects, the other sensor(s) can include sensor arrangements such as those described in U.S. Pat. No. 9,345,481, titled STAPLE CARTRIDGE TISSUE THICKNESS SENSOR SYSTEM, which issued on May 24, 2016, which is herein incorporated by reference in its entirety; U.S. Patent Application Publication No. 2014/0263552, titled STAPLE CARTRIDGE TISSUE THICKNESS SENSOR SYSTEM, which published on Sep. 18, 2014, which is herein incorporated by reference in its entirety; and U.S. patent application Ser. No. 15/628,175, titled TECHNIQUES FOR ADAPTIVE CONTROL OF MOTOR VELOCITY OF A SURGICAL STAPLING AND CUTTING INSTRUMENT, filed Jun. 20, 2017, which is herein incorporated by reference in its entirety. In a digital signal processing system, an absolute positioning system is coupled to a digital data acquisition system where the output of the absolute positioning system will have a finite resolution and sampling frequency. The absolute positioning system may comprise a compare-and-combine circuit to combine a computed response with a measured response using algorithms, such as a weighted average and a theoretical control loop, that drive the computed response towards the measured response. The computed response of the physical system may take into account properties like mass, inertia, viscous friction, inductance resistance, etc., to predict what the states and outputs of the physical system will be by knowing the input.

The absolute positioning system may provide an absolute position of the displacement member upon power-up of the instrument, without retracting or advancing the displacement member to a reset (zero or home) position as may be required with conventional rotary encoders that merely count the number of steps forwards or backwards that the motor 20230 has taken to infer the position of a device actuator, drive bar, knife, or the like.

A sensor 20226, such as, for example, a strain gauge or a micro-strain gauge, may be configured to measure one or more parameters of the end effector, such as, for example, the amplitude of the strain exerted on the anvil during a clamping operation, which can be indicative of the closure forces applied to the anvil. The measured strain may be converted to a digital signal and provided to the processor 20222. Alternatively, or in addition to the sensor 20226, a sensor 20227, such as, for example, a load sensor, can measure the closure force applied by the closure drive system to the anvil. The sensor 20227, such as, for example, a load sensor, can measure the firing force applied to an I-beam in a firing stroke of the surgical instrument or tool. The I-beam is configured to engage a wedge sled, which is configured to upwardly cam staple drivers to force out staples into deforming contact with an anvil. The I-beam also may include a sharpened cutting edge that can be used to sever tissue as the I-beam is advanced distally by the firing bar. Alternatively, a current sensor 20231 can be employed to measure the current drawn by the motor 20230. The force required to advance the firing member can correspond to the current drawn by the motor 20230, for example. The measured force may be converted to a digital signal and provided to the processor 20222.

For example, the strain gauge sensor 20226 can be used to measure the force applied to the tissue by the end effector. A strain gauge can be coupled to the end effector to measure the force on the tissue being treated by the end effector. A system for measuring forces applied to the tissue grasped by the end effector may comprise a strain gauge sensor 20226, such as, for example, a micro-strain gauge, that can be configured to measure one or more parameters of the end effector, for example. In one aspect, the strain gauge sensor 20226 can measure the amplitude or magnitude of the strain exerted on a jaw member of an end effector during a clamping operation, which can be indicative of the tissue compression. The measured strain can be converted to a digital signal and provided to a processor 20222 of the microcontroller 20221. A load sensor 20227 can measure the force used to operate the knife element, for example, to cut the tissue captured between the anvil and the staple cartridge. A magnetic field sensor can be employed to measure the thickness of the captured tissue. The measurement of the magnetic field sensor also may be converted to a digital signal and provided to the processor 20222.

The measurements of the tissue compression, the tissue thickness, and/or the force required to close the end effector on the tissue, as respectively measured by the sensors 20226, 20227, can be used by the microcontroller 20221 to characterize the selected position of the firing member and/or the corresponding value of the speed of the firing member. In one instance, a memory 20223 may store a technique, an equation, and/or a lookup table which can be employed by the microcontroller 20221 in the assessment.

The control system 20220 of the surgical instrument or tool also may comprise wired or wireless communication circuits to communicate with the modular communication hub 20065 as shown in FIG. 5.

Figure 7:
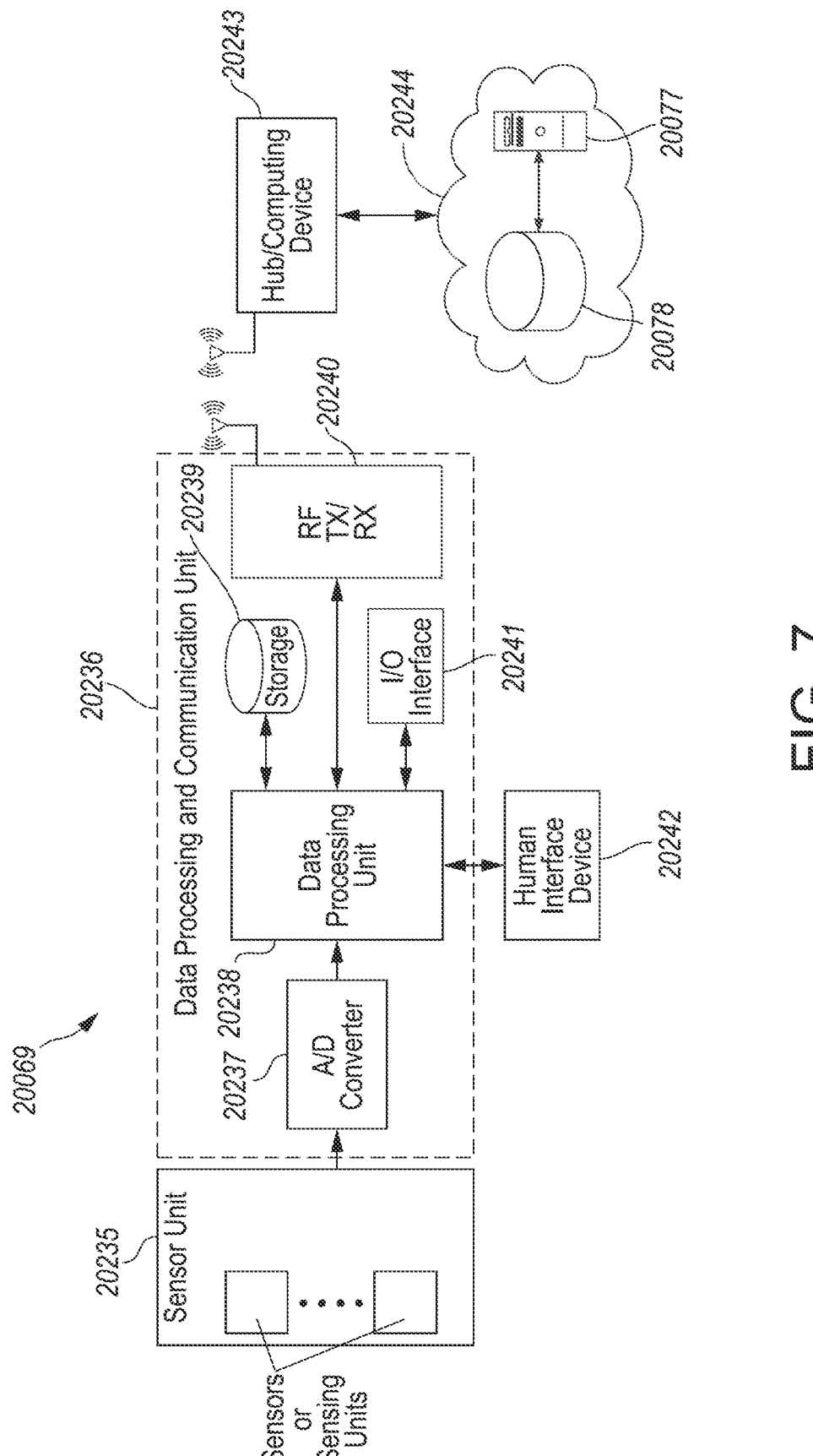
FIG. 7 shows an exemplary sensing system with a sensor unit and a data processing and communication unit.

FIG. 7 shows an example sensing system 20069. The sensing system may be an HCP sensing system or a patient sensing system. The sensing system 20069 may include a sensor unit 20235 and a human interface system 20242 that are in communication with a data processing and communication unit 20236. The data processing and communication unit 20236 may include an analog-to-digital converted 20237, a data processing unit 20238, a storage unit 20239, and an input/output interface 20241, a transceiver 20240. The sensing system 20069 may be in communication with a surgical hub or a computing device 20243, which in turn is in communication with a cloud computing system 20244. The cloud computing system 20244 may include a cloud storage system 20078 and one or more cloud servers 20077.

The sensor unit 20235 may include one or more ex vivo or in vivo sensors for measuring one or more biomarkers. The biomarkers may include, for example, blood pH, hydration state, oxygen saturation, core body temperature, heart rate, heart rate variability, sweat rate, skin conductance, blood pressure, light exposure, environmental temperature, respiratory rate, coughing and sneezing, gastrointestinal motility, gastrointestinal tract imaging, tissue perfusion pressure, bacteria in respiratory tract, alcohol consumption, lactate (sweat), peripheral temperature, positivity and optimism, adrenaline (sweat), cortisol (sweat), edema, mycotoxins, VO2 max, pre-operative pain, chemicals in the air, circulating tumor cells, stress and anxiety, confusion and delirium, physical activity, autonomic tone, circadian rhythm, menstrual cycle, sleep, etc. These biomarkers may be measured using one or more sensors, for example, photosensors (e.g., photodiodes, photoresistors), mechanical sensors (e.g., motion sensors), acoustic sensors, electrical sensors, electrochemical sensors, thermoelectric sensors, infrared sensors, etc. The sensors may measure the biomarkers as described herein using one of more of the following sensing technologies: photoplethysmography, electrocardiography, cephalography, colorimetry, impedimentary, potentiometry, amperometry, etc.

As illustrated in FIG. 7, a sensor in the sensor unit 20235 may measure a physiological signal (e.g., a voltage, a current, a PPG signal, etc.) associated with a biomarker to be measured. The physiological signal to be measured may depend on the sensing technology used, as described herein. The sensor unit 20235 of the sensing system 20069 may be in communication with the data processing and communication unit 20236. In an example, the sensor unit 20235 may communicate with the data processing and communication unit 20236 using a wireless interface. The data processing and communication unit 20236 may include an analog-to-digital converter (ADC) 20237, a data processing unit 20238, a storage 20239, an I/O interface 20241, and an RF transceiver 20240. The data processing unit 20238 may include a processor and a memory unit.

The sensor unit 20235 may transmit the measured physiological signal to the ADC 20237 of the data processing and communication unit 20236. In an example, the measured physiological signal may be passed through one or more filters (e.g., an RC low-pass filter) before being sent to the ADC. The ADC may convert the measured physiological signal into measurement data associated with the biomarker. The ADC may pass measurement data to the data processing unit 20238 for processing. In an example, the data processing unit 20238 may send the measurement data associated with the biomarker to a surgical hub or a computing device 20243, which in turn may send the measurement data to a cloud computing system 20244 for further processing. The data processing unit may send the measurement data to the surgical hub or the computing device 20243 using one of the wireless protocols, as described herein. In an example, the data processing unit 20238 may first process the raw measurement data received from the sensor unit and send the processed measurement data to the surgical hub or a computing device 20243.

In an example, the data processing and communication unit 20236 of the sensing system 20069 may receive a threshold value associated with a biomarker for monitoring from a surgical hub, a computing device 20243, or directly from a cloud server 20077 of the cloud computing system 20244. The data processing unit 20236 may compare the measurement data associated with the biomarker to be monitored with the corresponding threshold value received from the surgical hub, the computing device 20243, or the cloud server 20077. The data processing and communication unit 20236 may send a notification message to the HID 20242 indicating that a measurement data value has crossed the threshold value. The notification message may include the measurement data associated with the monitored biomarker. The data processing and computing unit 20236 may send a notification via a transmission to a surgical hub or a computing device 20243 using one of the following RF protocols: Bluetooth, Bluetooth Low-Energy (BLE), Bluetooth Smart, Zigbee, Z-wave, IPv6 Low-power wireless Personal Area Network (6LoWPAN), Wi-Fi. The data processing unit 20238 may send a notification (e.g., a notification for an HCP) directly to a cloud server via a transmission to a cellular transmission/reception point (TRP) or a base station using one or more of the following cellular protocols: GSM/GPRS/EDGE (2G), UMTS/HSPA (3G), long term evolution (LTE) or 4G, LTE-Advanced (LTE-A), new radio (NR) or 5G. In an example, the sensing unit may be in communication with the hub/computing device via a router.

In an example, the sensor unit may include a sensor and an analog-to-digital converted (ADC). The ADC in the sensor unit may convert a physiological signal measured by the sensor into measurement data associated with a biomarker. The sensor unit may send the measurement data to the data processing and communication unit for further processing. In an example, the sensor unit may send the measurement data to the data processing and communication unit using an inter-integrated circuit (I2C) interface.

The data processing and communication unit includes a data processing unit, a storage unit, and an RF transceiver. The sensing system may be in communication with a surgical hub or a computing device, which in turn may be in communication with a cloud computing system 20244. The cloud computing system 20244 may include a remote server 20077 and an associated remote storage 20078. The sensor unit may include one or more ex vivo or in vivo sensors for measuring one or more biomarkers, as described herein.

The data processing and communication unit after processing the measurement data received from the sensor unit may further process the measurement data and/or send the measurement data to the smart hub or the computing device 20243. In an example, the data processing and communication unit may send the measurement data received from the sensor unit to the remote server 20077 of the cloud computing system 20244 for further processing and/or monitoring.

In an example, the sensor unit may include multiple sensors to measure one or more physiological signals associated with a patient or surgeon's biomarkers and/or one or more physical state signals associated with physical state of a person. A list of biomarkers may include biomarkers such as those biomarkers disclosed herein. The ADC(s) in the sensor unit may convert each of the physiological signals and/or physical state signals measured by the multiple sensors into respective measurement data. The sensor unit may send the measurement data associated with one or more biomarkers as well as the physical state of the person being monitored to the data processing and communication unit for further processing. The sensor unit may send the measurement data to the data processing and communication unit individually for each of the sensors or combined for all the sensors. In an example, the sensor unit may send the measurement data to the data processing and communication unit via an I2C interface.

Figure 8:
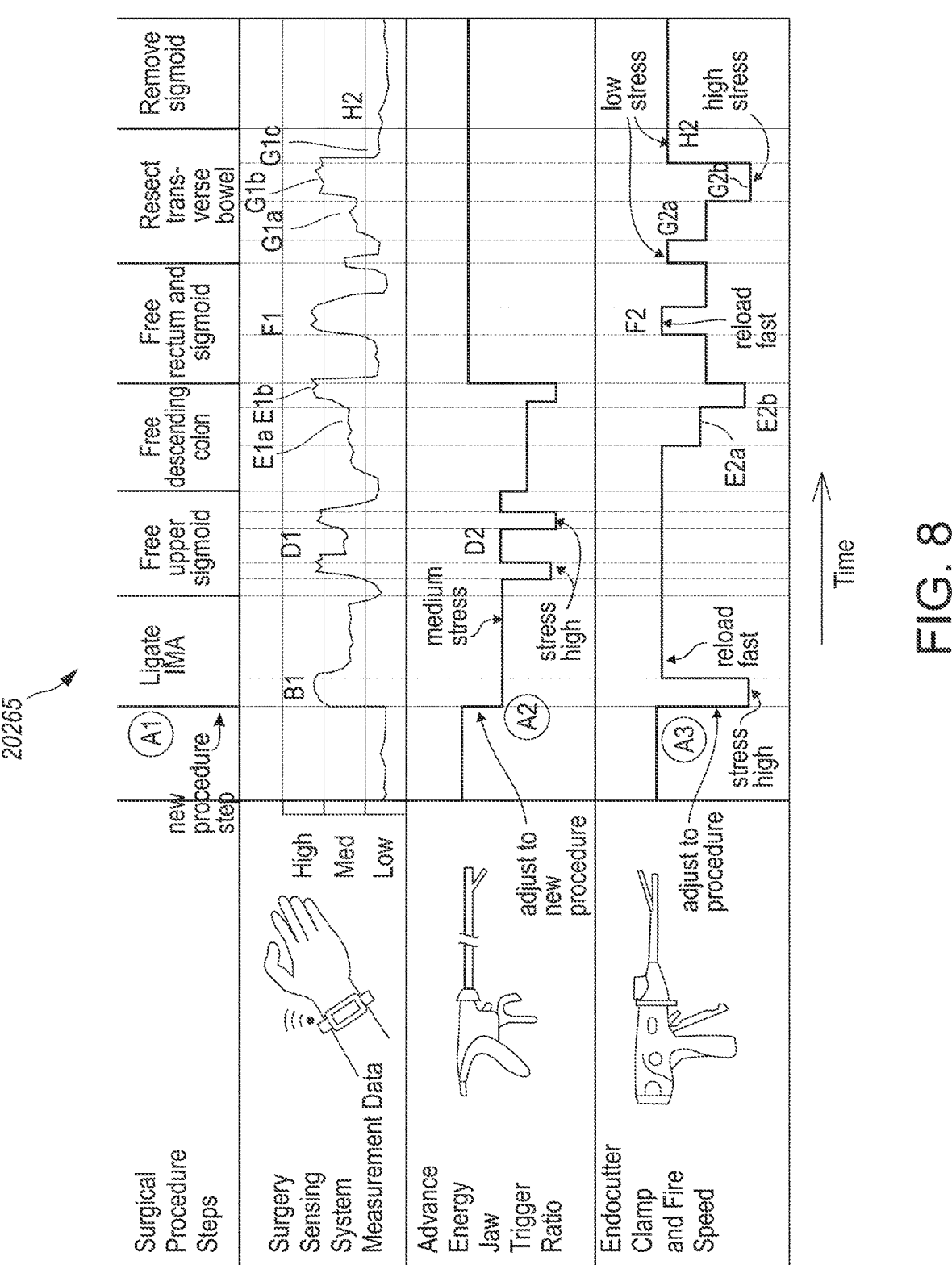
FIG. 8 illustrates an exemplary timeline of an illustrative surgical procedure indicating adjusting operational parameters of a surgical device based on a surgeon biomarker level.

FIG. 8 is an example of using a surgical task situational awareness and measurement data from one or more HCP sensing systems to adjust surgical instrument controls. FIG. 8 illustrates a timeline 20265 of an illustrative surgical procedure and the contextual information that a surgical hub can derive from data received from one or more surgical devices, one or more HCP sensing systems, and/or one or more environmental sensing systems at each step in the surgical procedure. The devices that could be controlled by a surgical hub may include advanced energy devices, endocutter clamps, etc. The HCP sensing systems may include sensing systems for measuring one or more biomarkers associated with the surgeon, for example, heart rate, sweat composition, respiratory rate, etc. The environmental sensing system may include systems for measuring one or more of the environmental attributes, for example, cameras for detecting a surgeon's position/movements/breathing pattern, spatial microphones, for example to measure ambient noise in the surgical theater and/or the tone of voice of a healthcare provider, temperature/humidity of the surroundings, etc.

In the following description of the timeline 20265 illustrated in FIG. 8, reference should also be made to FIG. 5. FIG. 5 provides various components used in a surgical procedure. The timeline 20265 depicts the steps that may be taken individually and/or collectively by the nurses, surgeons, and other medical personnel during the course of an exemplary colorectal surgical procedure. In a colorectal surgical procedure, a situationally aware surgical hub 20076 may receive data from various data sources throughout the course of the surgical procedure, including data generated each time an HCP utilizes a modular device/instrument 20095 that is paired with the surgical hub 20076. The surgical hub 20076 may receive this data from the paired modular devices 20095. The surgical hub may receive measurement data from sensing systems 20069. The surgical hub may use the data from the modular device/instruments 20095 and/or measurement data from the sensing systems 20069 to continually derive inferences (i.e., contextual information) about an HCP's stress level and the ongoing procedure as new data is received, such that the stress level of the surgeon relative to the step of the procedure that is being performed is obtained. The situational awareness system of the surgical hub 20076 may perform one or more of the following: record data pertaining to the procedure for generating reports, verify the steps being taken by the medical personnel, provide data or prompts (e.g., via a display screen) that may be pertinent for the particular procedural step, adjust modular devices based on the context (e.g., activate monitors, adjust the FOV of the medical imaging device, change the energy level of an ultrasonic surgical instrument or RF electrosurgical instrument), or take any other such action described herein. In an example, these steps may be performed by a remote server 20077 of a cloud system 20064 and communicated with the surgical hub 20076.

As a first step (not shown in FIG. 8 for brevity), the hospital staff members may retrieve the patient's EMR from the hospital's EMR database. Based on select patient data in the EMR, the surgical hub 20076 may determine that the procedure to be performed is a colorectal procedure. The staff members may scan the incoming medical supplies for the procedure. The surgical hub 20076 may cross-reference the scanned supplies with a list of supplies that can be utilized in various types of procedures and confirms that the mix of supplies corresponds to a colorectal procedure. The surgical hub 20076 may pair each of the sensing systems 20069 worn by different HCPs.

Once each of the devices is ready and pre-surgical preparation is complete, the surgical team may begin by making incisions and place trocars. The surgical team may perform access and prep by dissecting adhesions, if any, and identifying inferior mesenteric artery (IMA) branches. The surgical hub 20076 can infer that the surgeon is in the process of dissecting adhesions, at least based on the data it may receive from the RF or ultrasonic generator indicating that an energy instrument is being fired. The surgical hub 20076 may cross-reference the received data with the retrieved steps of the surgical procedure to determine that an energy instrument being fired at this point in the process (e.g., after the completion of the previously discussed steps of the procedure) corresponds to the dissection step.

After dissection, the HCP may proceed to the ligation step (e.g., indicated by A1) of the procedure. As illustrated in FIG. 8, the HCP may begin by ligating the IMA. The surgical hub 20076 may infer that the surgeon is ligating arteries and veins because it may receive data from the advanced energy jaw device and/or the endocutter indicating that the instrument is being fired. The surgical hub may also receive measurement data from one of the HCP's sensing systems indicating higher stress level of the HCP (e.g., indicated by B1 mark on the time axis). For example, higher stress level may be indicated by change in the HCP's heart rate from a base value. The surgical hub 20076, like the prior step, may derive this inference by cross-referencing the receipt of data from the surgical stapling and cutting instrument with the retrieved steps in the process (e.g., as indicated by A2 and A3). The surgical hub 20076 may monitor the advance energy jaw trigger ratio and/or the endocutter clamp and firing speed during the high stress time periods. In an example, the surgical hub 20076 may send an assistance control signal to the advanced energy jaw device and/or the endocutter device to control the device in operation. The surgical hub may send the assistance signal based on the stress level of the HCP that is operating the surgical device and/or situational awareness known to the surgical hub. For example, the surgical hub 20076 may send control assistance signals to an advanced energy device or an endocutter clamp, as indicated in FIG. 8 by A2 and A3.

The HCP may proceed to the next step of freeing the upper sigmoid followed by freeing descending colon, rectum, and sigmoid. The surgical hub 20076 may continue to monitor the high stress markers of the HCP (e.g., as indicated by D1, E1a, E1b, F1). The surgical hub 20076 may send assistance signals to the advanced energy jaw device and/or the endocutter device during the high stress time periods, as illustrated in FIG. 8.

After mobilizing the colon, the HCP may proceed with the segmentectomy portion of the procedure. For example, the surgical hub 20076 may infer that the HCP is transecting the bowel and sigmoid removal based on data from the surgical stapling and cutting instrument, including data from its cartridge. The cartridge data can correspond to the size or type of staple being fired by the instrument, for example. As different types of staples are utilized for different types of tissues, the cartridge data can thus indicate the type of tissue being stapled and/or transected. It should be noted that surgeons regularly switch back and forth between surgical stapling/cutting instruments and surgical energy (e.g., RF or ultrasonic) instruments depending upon the step in the procedure because different instruments are better adapted for particular tasks. Therefore, the sequence in which the stapling/cutting instruments and surgical energy instruments are used can indicate what step of the procedure the surgeon is performing.

The surgical hub may determine and send a control signal to surgical device based on the stress level of the HCP. For example, during time period G1b, a control signal G2b may be sent to an endocutter clamp. Upon removal of the sigmoid, the incisions are closed, and the post-operative portion of the procedure may begin. The patient's anesthesia can be reversed. The surgical hub 20076 may infer that the patient is emerging from the anesthesia based on one or more sensing systems attached to the patient.

Figure 9:
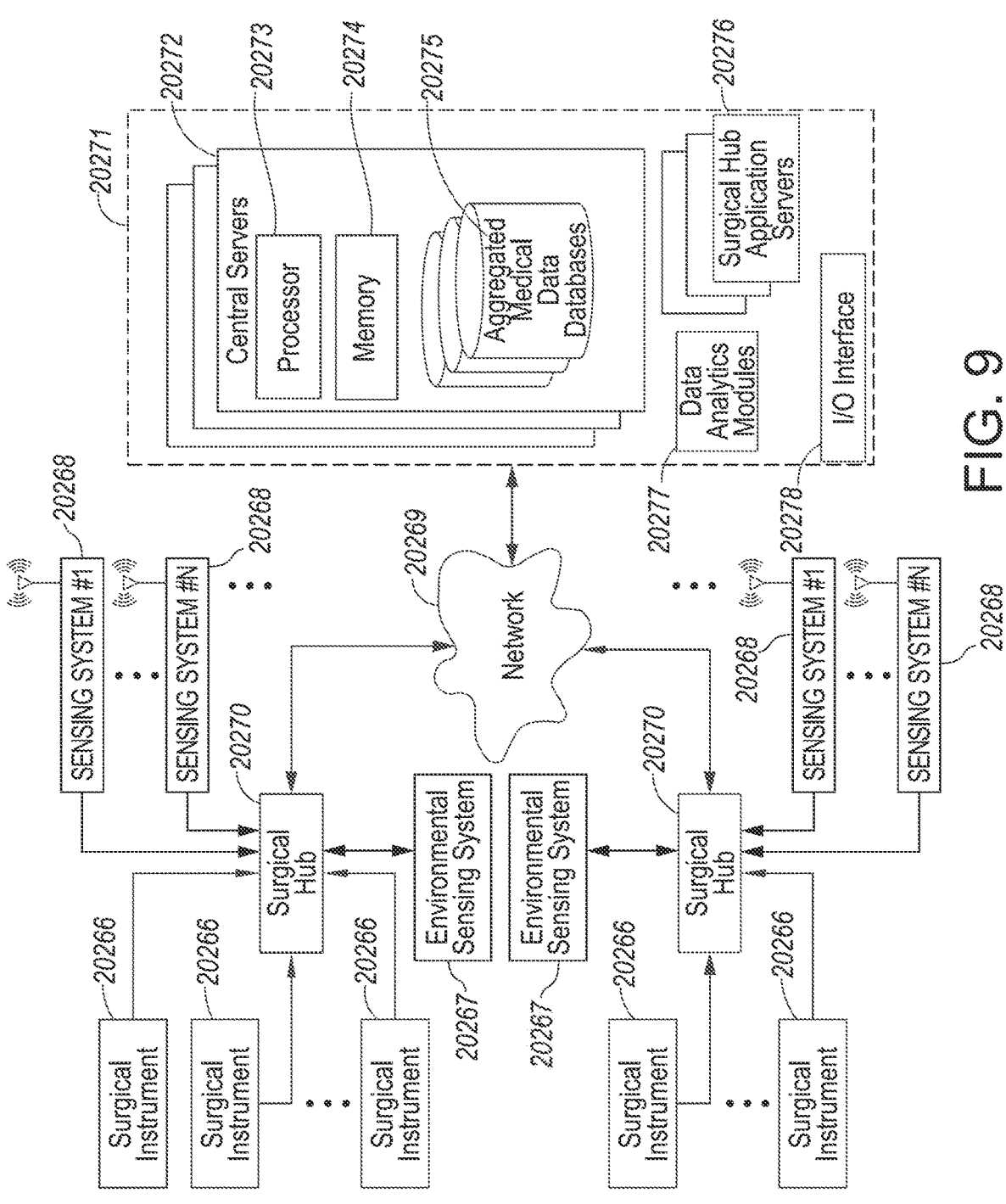
FIG. 9 is a block diagram of the computer-implemented interactive HCP monitoring system.

FIG. 9 shows an example computer-implemented interactive surgical system may be configured to monitor HCP biomarkers using one or more sensing systems 20001. The computer-implemented interactive surgical system may be configured to monitor HCP biomarkers using one or more sensing systems 20069. The HCP biomarkers and/or the patient biomarkers may be measured before, after, and/or during a surgical procedure. In one aspect, the computer-implemented interactive surgical system may be configured to monitor and analyze data related to the operation of various surgical systems 20069 that include surgical hubs, surgical instruments, robotic devices and operating theaters or healthcare facilities. The computer-implemented interactive surgical system may include a cloud-based analytics system. The computer-implemented interactive surgical system may include a local analytics system. The cloud-based analytics system may include one or more analytics servers.

A monitoring and analytics system may include a plurality of sensing systems 20268 (may be the same or similar to the sensing systems 20069), surgical instruments 20266 (may be the same or similar to instruments 20031), and/or a plurality of surgical hubs 20270 (may be the same or similar to hubs 20006). A surgical data network 20269 (may be the same or similar to the surgical data network described in FIG. 4) may couple the surgical hubs 20270 to the computing system 20271 (may be a local computing system, an edge computing system, or may be a cloud computing system such as cloud computing system 20064). The surgical hubs 20270 may be communicatively coupled to one or more surgical instruments 20266. The surgical hubs 20270 may also be communicatively coupled to the one or more sensing systems 20268, and the cloud 20271 of the computer-implemented interactive surgical system via the network 20269. The surgical hubs 20270 and the sensing systems 20268 may be communicatively coupled using wireless protocols as described herein. The computing system 20271 may be a local or remote centralized source of hardware and software for storing, processing, manipulating, and communicating measurement data from the sensing systems 20268 and data generated based on the operation of various surgical instruments 20266.

As shown in FIG. 9, access to the computing system 20271 may be achieved via the network 20269. The network 20269 may be the Internet or some other suitable computer network. Surgical hubs 20270 that may be coupled to the computing system 20271 can be considered the client side of the computing system (e.g., cloud-based analytics system). Surgical instruments 20266 may be paired with the surgical hubs 20270 for control and implementation of various surgical procedures and/or operations, as described herein. Sensing systems 20268 may be paired with surgical hubs 20270 for in-surgical HCP monitoring of surgeon related biomarkers, pre-surgical HCP monitoring, monitoring, or post-surgical HCP monitoring. Environmental sensing systems 20267 may be paired with surgical hubs 20270 measuring environmental attributes associated with an HCP.

Surgical instruments 20266, environmental sensing systems 20267, and sensing systems 20268 may comprise wired or wireless transceivers for data transmission to and from their corresponding surgical hubs 20270 (which may also comprise transceivers). Combinations of one or more of surgical instruments 20266, sensing systems 20268, or surgical hubs 20270 may indicate particular locations, such as operating theaters, intensive care unit (ICU) rooms, or recovery rooms in healthcare facilities (e.g., hospitals), for providing medical operations, pre-surgical preparation, and/or post-surgical recovery. For example, the memory of a surgical hub 20270 may store location data.

As shown in FIG. 9, the computing system 20271 may include one or more central servers 20272 (may be same or similar to remote server 20067), surgical hub application servers 20276, data analytics modules 20277, and an input/output ("I/O") interface 20278. The central servers 20272 of the computing system 20271 may collectively administer the cloud computing system, which includes monitoring requests by client surgical hubs 20270 and managing the processing capacity of the computing system 20271 for executing the requests. Each of the central servers 20272 may comprise one or more processors 20273 coupled to suitable memory devices 20274 which can include volatile memory such as random-access memory (RAM) and non-volatile memory such as magnetic storage devices. The memory devices 20274 may comprise machine executable instructions that when executed cause the processors 20273 to execute the data analytics modules 20277 for the cloud-based data analysis, real-time monitoring of measurement data received from the sensing systems 20268, operations, recommendations, and other operations as described herein. The processors 20273 can execute the data analytics modules 20277 independently or in conjunction with hub applications independently executed by the hubs 20270. The central servers 20272 also may include aggregated medical data databases 20275, which can reside in the memory 20274.

Based on connections to various surgical hubs 20270 via the network 20269, the computing system 20271 can aggregate data from specific data generated by various surgical instruments 20266, real-time data from sensing systems 20268, and/or the surgical hubs 20270. Such aggregated data may be stored within the aggregated medical databases 20275 associated with the computing system 20271. The computing system 20271 may track real-time measurement data from the sensing systems 20268 and/or perform data analysis and operations on the measurement data and/or the aggregated data to yield insights and/or perform functions that individual hubs 20270 could not achieve on their own.

As shown in FIG. 9, the computing system 20271 and the surgical hubs 20270 may be communicatively coupled to send and receive information. The I/O interface 20278 is connected to the plurality of surgical hubs 20270 via the network 20269. The I/O interface 20278 can be configured to transfer information between the surgical hubs 20270 and the aggregated medical data databases 20275. The I/O interface 20278 may facilitate read/write operations of the cloud-based analytics system. Such read/write operations may be executed in response to requests from hubs 20270. These requests could be transmitted to the surgical hubs 20270 through the hub applications. The I/O interface 20278 may include one or more high speed data ports, which may include universal serial bus (USB) ports, IEEE 1394 ports, as well as Wi-Fi and Bluetooth I/O interfaces for connecting the computing system 20271 to surgical hubs 20270. The hub application servers 20276 of the computing system 20271 may be configured to host and supply shared capabilities to software applications (e.g., hub applications) executed by surgical hubs 20270. For example, the hub application servers 20276 may manage requests made by the hub applications through the hubs 20270, control access to the aggregated medical data databases 20275, and perform load balancing.

The computing system may address various issues arising in the context of medical operations (e.g., pre-surgical monitoring, in-surgical monitoring, and post-surgical monitoring) and procedures performed using medical devices, such as the surgical instruments 20266, 20031. The surgical instruments 20266 may be digital surgical devices configured to interact with the computing system 20271 for implementing techniques to improve the performance of surgical operations. The computing system may address various issues arising in the context of monitoring one or more biomarkers associated with HCP(s) or a patient in pre-surgical, in-surgical, and post-surgical procedures using sensing systems 20268. Sensing systems 20268 may interact with the surgical hub 20270 and/or with the computing system 20271 for implementing techniques to monitor surgeon biomarkers and/or patient biomarkers. The sensing systems 20268 may include systems with one or more sensors that are configured to measure one or more biomarkers associated with an HCP participating in a medical operation and/or a patient on whom a medical operation is planned to be performed, is being performed or has been performed. Various surgical instruments 20266, sensing systems 20268, and/or surgical hubs 20270 may include human interface systems (e.g., having a touch-controlled user interfaces) such that HCPS and/or patients may control aspects of interaction between the surgical instruments 20266 or the sensing system 20268 and the computing system 20271. Other suitable user interfaces for control such as auditory controlled user interfaces may also be used.

Figure 10:
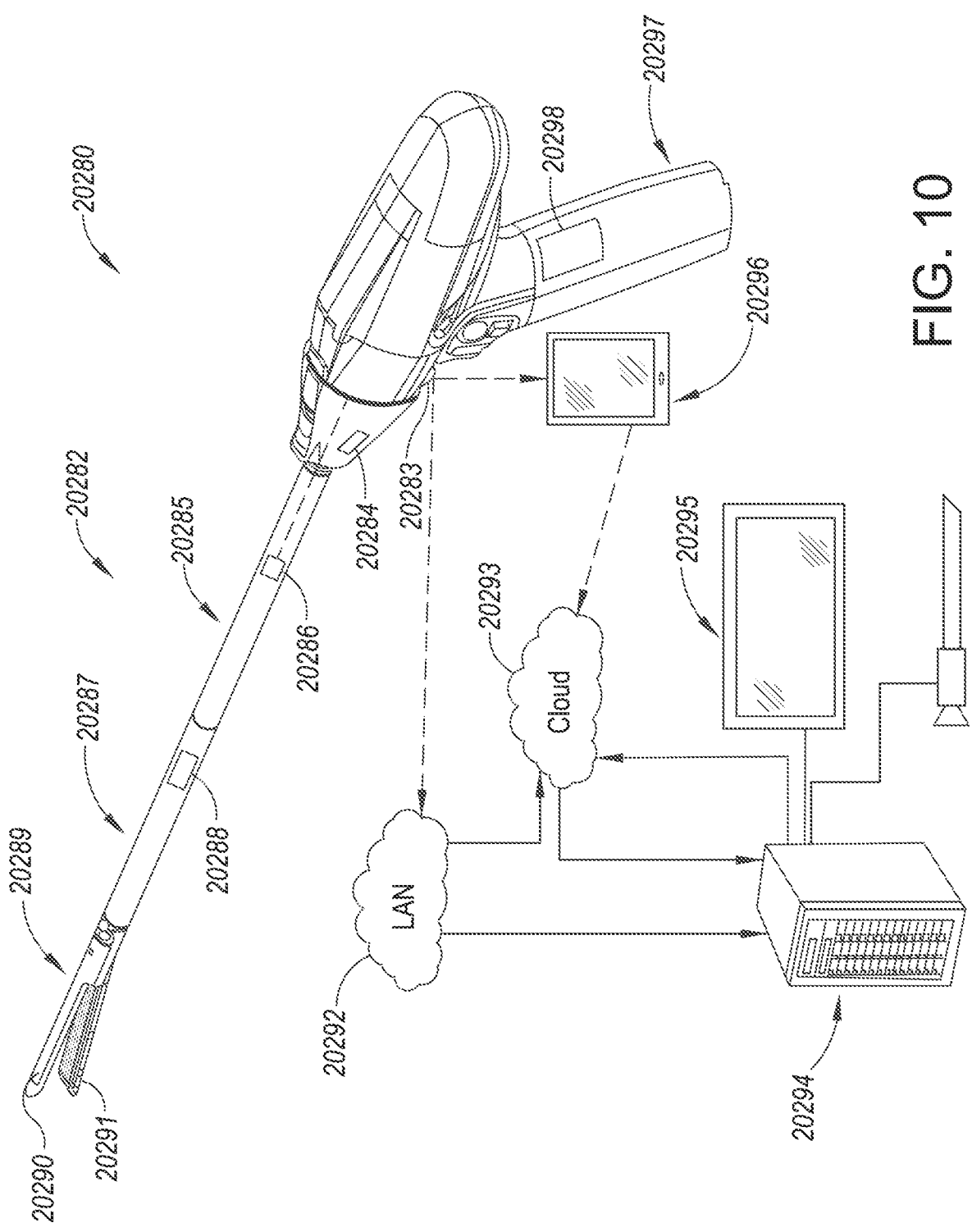
FIG. 10 shows an example surgical system having a surgical instrument in communication with a console or a portable device.

FIG. 10 illustrates an example surgical system 20280 in accordance with the present disclosure and may include a surgical instrument 20282 that can be in communication with a console 20294 or a portable device 20296 through a local area network 20292 and/or a cloud network 20293 via a wired and/or wireless connection. The console 20294 and the portable device 20296 may be any suitable computing device. The surgical instrument 20282 may include a handle 20297, an adapter 20285, and a loading unit 20287. The adapter 20285 releasably couples to the handle 20297 and the loading unit 20287 releasably couples to the adapter 20285 such that the adapter 20285 transmits a force from a drive shaft to the loading unit 20287. The adapter 20285 or the loading unit 20287 may include a force gauge (not explicitly shown) disposed therein to measure a force exerted on the loading unit 20287. The loading unit 20287 may include an end effector 20289 having a first jaw 20291 and a second jaw 20290. The loading unit 20287 may be an in-situ loaded or multi-firing loading unit (MFLU) that allows a clinician to fire a plurality of fasteners multiple times without requiring the loading unit 20287 to be removed from a surgical site to reload the loading unit 20287.

The first and second jaws 20291, 20290 may be configured to clamp tissue therebetween, fire fasteners through the clamped tissue, and sever the clamped tissue. The first jaw 20291 may be configured to fire at least one fastener a plurality of times or may be configured to include a replaceable multi-fire fastener cartridge including a plurality of fasteners (e.g., staples, clips, etc.) that may be fired more than one time prior to being replaced. The second jaw 20290 may include an anvil that deforms or otherwise secures the fasteners, as the fasteners are ejected from the multi-fire fastener cartridge.

The handle 20297 may include a motor that is coupled to the drive shaft to affect rotation of the drive shaft. The handle 20297 may include a control interface to selectively activate the motor. The control interface may include buttons, switches, levers, sliders, touchscreen, and any other suitable input mechanisms or user interfaces, which can be engaged by a clinician to activate the motor.

The control interface of the handle 20297 may be in communication with a controller 20298 of the handle 20297 to selectively activate the motor to affect rotation of the drive shafts. The controller 20298 may be disposed within the handle 20297 and may be configured to receive input from the control interface and adapter data from the adapter 20285 or loading unit data from the loading unit 20287. The controller 20298 may analyze the input from the control interface and the data received from the adapter 20285 and/or loading unit 20287 to selectively activate the motor. The handle 20297 may also include a display that is viewable by a clinician during use of the handle 20297. The display may be configured to display portions of the adapter or loading unit data before, during, or after firing of the instrument 20282.

The adapter 20285 may include an adapter identification device 20284 disposed therein and the loading unit 20287 may include a loading unit identification device 20288 disposed therein. The adapter identification device 20284 may be in communication with the controller 20298, and the loading unit identification device 20288 may be in communication with the controller 20298. It will be appreciated that the loading unit identification device 20288 may be in communication with the adapter identification device 20284, which relays or passes communication from the loading unit identification device 20288 to the controller 20298.

The adapter 20285 may also include a plurality of sensors 20286 (one shown) disposed thereabout to detect various conditions of the adapter 20285 or of the environment (e.g., if the adapter 20285 is connected to a loading unit, if the adapter 20285 is connected to a handle, if the drive shafts are rotating, the torque of the drive shafts, the strain of the drive shafts, the temperature within the adapter 20285, a number of firings of the adapter 20285, a peak force of the adapter 20285 during firing, a total amount of force applied to the adapter 20285, a peak retraction force of the adapter 20285, a number of pauses of the adapter 20285 during firing, etc.). The plurality of sensors 20286 may provide an input to the adapter identification device 20284 in the form of data signals. The data signals of the plurality of sensors 20286 may be stored within or be used to update the adapter data stored within the adapter identification device 20284. The data signals of the plurality of sensors 20286 may be analog or digital. The plurality of sensors 20286 may include a force gauge to measure a force exerted on the loading unit 20287 during firing.

The handle 20297 and the adapter 20285 can be configured to interconnect the adapter identification device 20284 and the loading unit identification device 20288 with the controller 20298 via an electrical interface. The electrical interface may be a direct electrical interface (i.e., include electrical contacts that engage one another to transmit energy and signals therebetween). Additionally, or alternatively, the electrical interface may be a non-contact electrical interface to wirelessly transmit energy and signals therebetween (e.g., inductively transfer). It is also contemplated that the adapter identification device 20284 and the controller 20298 may be in wireless communication with one another via a wireless connection separate from the electrical interface.

The handle 20297 may include a transceiver 20283 that is configured to transmit instrument data from the controller 20298 to other components of the system 20280 (e.g., the LAN 20292, the cloud 20293, the console 20294, or the portable device 20296). The controller 20298 may also transmit instrument data and/or measurement data associated with one or more sensors 20286 to a surgical hub 20270, as illustrated in FIG. 9. The transceiver 20283 may receive data (e.g., cartridge data, loading unit data, adapter data, or other notifications) from the surgical hub 20270. The transceiver 20283 may receive data (e.g., cartridge data, loading unit data, or adapter data) from the other components of the system 20280. For example, the controller 20298 may transmit instrument data including a serial number of an attached adapter (e.g., adapter 20285) attached to the handle 20297, a serial number of a loading unit (e.g., loading unit 20287) attached to the adapter 20285, and a serial number of a multi-fire fastener cartridge loaded into the loading unit to the console 20294. Thereafter, the console 20294 may transmit data (e.g., cartridge data, loading unit data, or adapter data) associated with the attached cartridge, loading unit, and adapter, respectively, back to the controller 20298. The controller 20298 can display messages on the local instrument display or transmit the message, via transceiver 20283, to the console 20294 or the portable device 20296 to display the message on the display 20295 or portable device screen, respectively.

Figure 11:
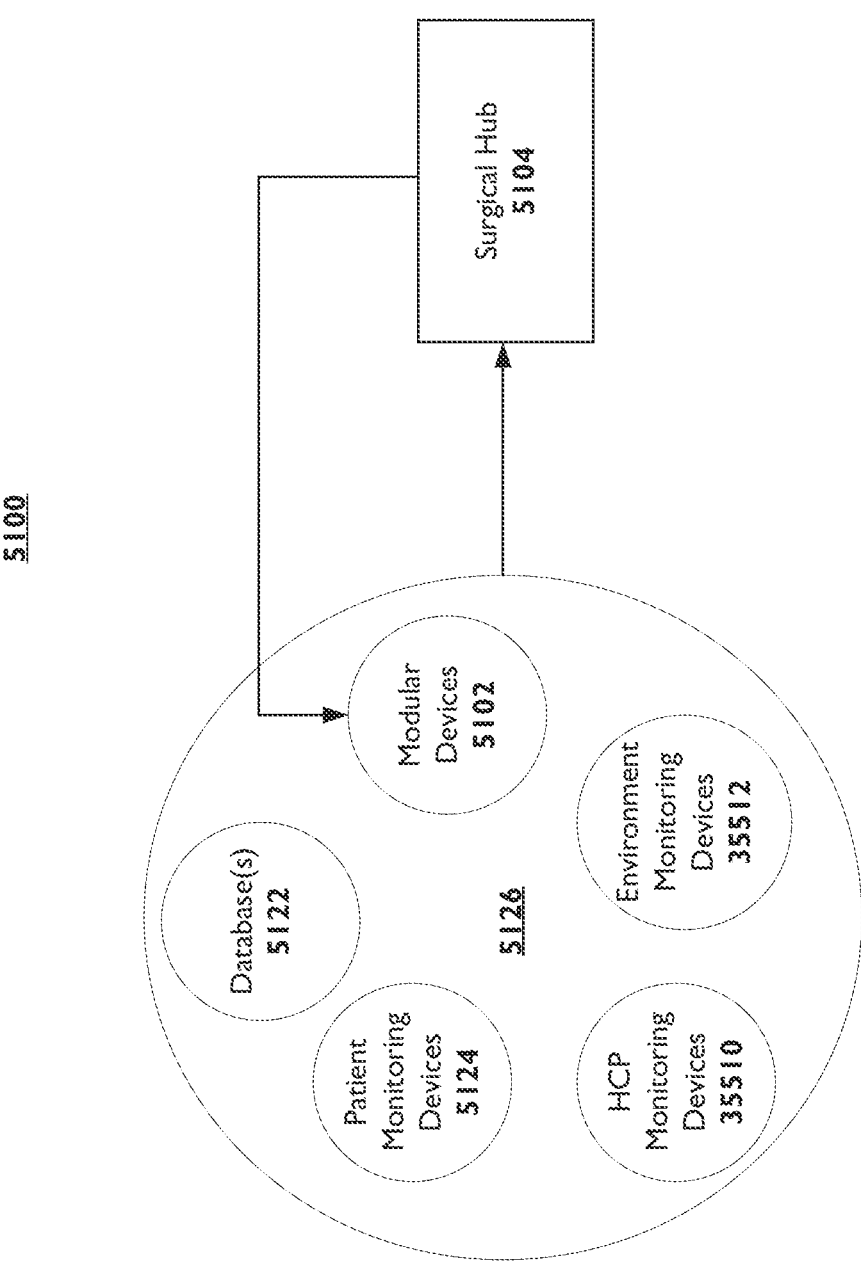
FIG. 11 is a diagram of an example situationally aware surgical system.

FIG. 11 illustrates a diagram of a situationally aware surgical system 5100, in accordance with at least one aspect of the present disclosure. The data sources 5126 may include, for example, the modular devices 5102 (which can include sensors configured to detect parameters associated with the patient, HCPs and environment and/or the modular device itself), databases 5122 (e.g., an EMR database containing patient records), and patient monitoring devices 5124 (e.g., a blood pressure (BP) monitor and an electrocardiography (EKG) monitor), HCP monitoring devices 35510, and/or environment monitoring devices 35512. The surgical hub 5104 can be configured to derive the contextual information pertaining to the surgical procedure from the data based upon, for example, the particular combination(s) of received data or the particular order in which the data is received from the data sources 5126. The contextual information inferred from the received data can include, for example, the type of surgical procedure being performed, the particular step of the surgical procedure that the surgeon is performing, the type of tissue being operated on, or the body cavity that is the subject of the procedure. This ability by some aspects of the surgical hub 5104 to derive or infer information related to the surgical procedure from received data can be referred to as "situational awareness." For example, the surgical hub 5104 can incorporate a situational awareness system, which is the hardware and/or programming associated with the surgical hub 5104 that derives contextual information pertaining to the surgical procedure from the received data.

The situational awareness system of the surgical hub 5104 can be configured to derive the contextual information from the data received from the data sources 5126 in a variety of different ways. For example, the situational awareness system can include a pattern recognition system, or machine learning system (e.g., an artificial neural network), that has been trained on training data to correlate various inputs (e.g., data from database(s) 5122, patient monitoring devices 5124, modular devices 5102, HCP monitoring devices 35510, and/or environment monitoring devices 35512) to corresponding contextual information regarding a surgical procedure. A machine learning system can be trained to accurately derive contextual information regarding a surgical procedure from the provided inputs. In examples, the situational awareness system can include a lookup table storing pre-characterized contextual information regarding a surgical procedure in association with one or more inputs (or ranges of inputs) corresponding to the contextual information. In response to a query with one or more inputs, the lookup table can return the corresponding contextual information for the situational awareness system for controlling the modular devices 5102. In examples, the contextual information received by the situational awareness system of the surgical hub 5104 can be associated with a particular control adjustment or set of control adjustments for one or more modular devices 5102. In examples, the situational awareness system can include a further machine learning system, lookup table, or other such system, which generates or retrieves one or more control adjustments for one or more modular devices 5102 when provided the contextual information as input.

A surgical hub 5104 incorporating a situational awareness system can provide a number of benefits for the surgical system 5100. One benefit may include improving the interpretation of sensed and collected data, which would in turn improve the processing accuracy and/or the usage of the data during the course of a surgical procedure. To return to a previous example, a situationally aware surgical hub 5104 could determine what type of tissue was being operated on; therefore, when an unexpectedly high force to close the surgical instrument's end effector is detected, the situationally aware surgical hub 5104 could correctly ramp up or ramp down the motor of the surgical instrument for the type of tissue.

The type of tissue being operated can affect the adjustments that are made to the compression rate and load thresholds of a surgical stapling and cutting instrument for a particular tissue gap measurement. A situationally aware surgical hub 5104 could infer whether a surgical procedure being performed is a thoracic or an abdominal procedure, allowing the surgical hub 5104 to determine whether the tissue clamped by an end effector of the surgical stapling and cutting instrument is lung (for a thoracic procedure) or stomach (for an abdominal procedure) tissue. The surgical hub 5104 could then adjust the compression rate and load thresholds of the surgical stapling and cutting instrument appropriately for the type of tissue.

The type of body cavity being operated in during an insufflation procedure can affect the function of a smoke evacuator. A situationally aware surgical hub 5104 could determine whether the surgical site is under pressure (by determining that the surgical procedure is utilizing insufflation) and determine the procedure type. As a procedure type can be generally performed in a specific body cavity, the surgical hub 5104 could then control the motor rate of the smoke evacuator appropriately for the body cavity being operated in. Thus, a situationally aware surgical hub 5104 could provide a consistent amount of smoke evacuation for both thoracic and abdominal procedures.

The type of procedure being performed can affect the optimal energy level for an ultrasonic surgical instrument or radio frequency (RF) electrosurgical instrument to operate at. Arthroscopic procedures, for example, may require higher energy levels because the end effector of the ultrasonic surgical instrument or RF electrosurgical instrument is immersed in fluid. A situationally aware surgical hub 5104 could determine whether the surgical procedure is an arthroscopic procedure. The surgical hub 5104 could then adjust the RF power level or the ultrasonic amplitude of the generator (e.g., "energy level") to compensate for the fluid filled environment. Relatedly, the type of tissue being operated on can affect the optimal energy level for an ultrasonic surgical instrument or RF electrosurgical instrument to operate at. A situationally aware surgical hub 5104 could determine what type of surgical procedure is being performed and then customize the energy level for the ultrasonic surgical instrument or RF electrosurgical instrument, respectively, according to the expected tissue profile for the surgical procedure. Furthermore, a situationally aware surgical hub 5104 can be configured to adjust the energy level for the ultrasonic surgical instrument or RF electrosurgical instrument throughout the course of a surgical procedure, rather than just on a procedure-by-procedure basis. A situationally aware surgical hub 5104 could determine what step of the surgical procedure is being performed or will subsequently be performed and then update the control algorithms for the generator and/or ultrasonic surgical instrument or RF electrosurgical instrument to set the energy level at a value appropriate for the expected tissue type according to the surgical procedure step.

In examples, data can be drawn from additional data sources 5126 to improve the conclusions that the surgical hub 5104 draws from one data source 5126. A situationally aware surgical hub 5104 could augment data that it receives from the modular devices 5102 with contextual information that it has built up regarding the surgical procedure from other data sources 5126. For example, a situationally aware surgical hub 5104 can be configured to determine whether hemostasis has occurred (e.g., whether bleeding at a surgical site has stopped) according to video or image data received from a medical imaging device. The surgical hub 5104 can be further configured to compare a physiologic measurement (e.g., blood pressure sensed by a BP monitor communicably connected to the surgical hub 5104) with the visual or image data of hemostasis (e.g., from a medical imaging device communicably coupled to the surgical hub 5104) to make a determination on the integrity of the staple line or tissue weld. The situational awareness system of the surgical hub 5104 can consider the physiological measurement data to provide additional context in analyzing the visualization data. The additional context can be useful when the visualization data may be inconclusive or incomplete on its own.

For example, a situationally aware surgical hub 5104 could proactively activate the generator to which an RF electrosurgical instrument is connected if it determines that a subsequent step of the procedure requires the use of the instrument. Proactively activating the energy source can allow the instrument to be ready for use a soon as the preceding step of the procedure is completed.

The situationally aware surgical hub 5104 could determine whether the current or subsequent step of the surgical procedure requires a different view or degree of magnification on the display according to the feature(s) at the surgical site that the surgeon is expected to need to view. The surgical hub 5104 could proactively change the displayed view (supplied by, e.g., a medical imaging device for the visualization system 108) accordingly so that the display automatically adjusts throughout the surgical procedure.

The situationally aware surgical hub 5104 could determine which step of the surgical procedure is being performed or will subsequently be performed and whether particular data or comparisons between data will be required for that step of the surgical procedure. The surgical hub 5104 can be configured to automatically call up data screens based upon the step of the surgical procedure being performed, without waiting for the surgeon to ask for the particular information.

Errors may be checked during the setup of the surgical procedure or during the course of the surgical procedure. For example, the situationally aware surgical hub 5104 could determine whether the operating theater is setup properly or optimally for the surgical procedure to be performed. The surgical hub 5104 can be configured to determine the type of surgical procedure being performed, retrieve the corresponding checklists, product location, or setup needs (e.g., from a memory), and then compare the current operating theater layout to the standard layout for the type of surgical procedure that the surgical hub 5104 determines is being performed. In some exemplifications, the surgical hub 5104 can compare the list of items for the procedure and/or a list of devices paired with the surgical hub 5104 to a recommended or anticipated manifest of items and/or devices for the given surgical procedure. If there are any discontinuities between the lists, the surgical hub 5104 can provide an alert indicating that a particular modular device 5102, patient monitoring device 5124, HCP monitoring devices 35510, environment monitoring devices 35512, and/or other surgical item is missing. In some examples, the surgical hub 5104 can determine the relative distance or position of the modular devices 5102 and patient monitoring devices 5124 via proximity sensors, for example. The surgical hub 5104 can compare the relative positions of the devices to a recommended or anticipated layout for the particular surgical procedure. If there are any discontinuities between the layouts, the surgical hub 5104 can be configured to provide an alert indicating that the current layout for the surgical procedure deviates from the recommended layout.

The situationally aware surgical hub 5104 could determine whether the surgeon (or other HCP(s) was making an error or otherwise deviating from the expected course of action during the course of a surgical procedure. For example, the surgical hub 5104 can be configured to determine the type of surgical procedure being performed, retrieve the corresponding list of steps or order of equipment usage (e.g., from a memory), and then compare the steps being performed or the equipment being used during the course of the surgical procedure to the expected steps or equipment for the type of surgical procedure that the surgical hub 5104 determined is being performed. The surgical hub 5104 can provide an alert indicating that an unexpected action is being performed or an unexpected device is being utilized at the particular step in the surgical procedure.

The surgical instruments (and other modular devices 5102) may be adjusted for the particular context of each surgical procedure (such as adjusting to different tissue types) and validating actions during a surgical procedure. Next steps, data, and display adjustments may be provided to surgical instruments (and other modular devices 5102) in the surgical theater according to the specific context of the procedure.

Object detection can be performed via computer vision and image processing that deals with detecting instances of semantic objects of a certain class (such as humans, equipment, or objects) in digital images and videos. Object detection is used in computer vision tasks such as image annotation, activity recognition, face detection, face recognition, video object co-segmentation. Object detection is used in tracking objects, for example tracking a ball during a football match, tracking movement of a cricket bat, or tracking a person in a video. Object detection may be performed via neural network-based approach(es), and/or non-neural approaches. For example, features may be defined and classification may be performed based on the defined features, for example, via support vector machine (SVM). Neural techniques may perform object detection without specifically defining features, and may be based on convolutional neural networks (CNN).

Moving object detection may be performed to recognize the physical movement of a person or an object in a given place or region. By acting segmentation among moving objects and stationary area or region, the moving objects motion could be tracked and thus could be analyzed later. Moving object detection may be performed via background subtraction, frame differencing, temporal differencing, and or optical flow analysis.

Smart and self-identifying RF systems may be used to locate HCPs and equipment in the OR. HCPs, instruments, equipment and/or boundaries may be located using spatial identifying sensors. The locations of HCPs, equipment and/or boundaries may be tracked with respect to the room and/or with respect to the patient, via wireless sensors and beacons.

A wearable monitoring system may be coupled to a person, such as an HCP or a patient. Ultra-wide band monitoring may be performed to identify the location of the person within the OR, and/or the person's relative position to an equipment, a surgical instrument, another person, a boundary, and/or the like.

RF element identification and boundary monitoring may be performed. RF beacons may be placed on equipment or instruments. BLE beacons may be placed in physical OR's. For example, beacons may be placed in corners of the OR, outlining the boundaries of the room. BLE beacons may be place on structures, such as large structures within the OR. BLE beacons may be placed on device for monitoring the device location relative to one or more boundaries.

For example, RFID tags may be affixed onto instruments and/or HCPs. Electromagnetic gates may be placed in the OR to prevent or to minimize violation of boundaries.

Boundary violations may be detected by tracking beacon movements. For example, the surgical hub may detect a boundary violation upon determining that the beacon has moved across a boundary. If the boundary violation is associated with a device crossing a boundary, the surgical hub may deactivate the device and alert an HCP of change of status. If the boundary violation is a larger structure, an urgent message can be displayed to indicate the equipment is of concern.

RF beacons may be used to locate HCPS in the OR theater. The location of an HCP may be tracked via their identification badge. The identification badge may have an imbedded RF beacon. The RF beacon may be high frequency (HF) or ultra-high frequency (UHF). The read range may not be affected by fluids or the need to penetrate structures. Since the size of the OR's can vary, the HF or UHF can provide sufficient coverage to accommodate potential distance from the surgical hub.

A surgical instrument may be associated with a unique RFID identification. The location of the surgical instrument may be tracked. The current use and/or the previous history of the surgical instrument may be determined based on location tracking. An external reader from the surgical hub may be positioned around the patient. The external reader may be used to track surgical instruments that enter the OR field. A low frequency or an HF chip may be used on instruments. The low or high frequencies may enable the reader to penetrate body fluids.

Instrument use can be determined and tracked based on its location. For example, the number of times a surgical instrument has been used, the length of time a device was in the patient, and/or a level of security that the device had been through a sterilization cycle prior to being introduced into the OR may be determined via location tracking. Whether an instrument has been left in the patient may be detected via location tracking of the instrument.

OR room imaging may be performed by multiple sources via various technologies to determine HCP, instrument, and/or equipment locations and their aspects. More than one imaging device can be used through different energy types to locate objects and people within the OR, the walls of the OR, and/or their proximity. The location and/or proximity information may be used to identify and/or control their interactions. Instruments and/or equipment may be configured based on the identified interactions.

For example, ultrasonic echo location may be used to determine object motion and measurements of location. OR visual or multi-spectral imaging may be used to monitor user location, interaction, and communication. Audio monitoring may be used to determine and record noise generating monitoring and tracking.

Infrared (IR) thermographic monitoring may be used to monitor the core temperate and the changes of temperature of HCPs and patient to adjust systems, monitor for infection, and/or understand situational awareness. As an HCP enters into the OR, an IR signature may be created for the HCP. An initial IR association response may be logged, for example, via the surgical hub. During a procedure, if the stress levels of the HCP increases, the IR signature may display or register the increased stress levels.

The various imaging systems may be used in concert. For example, the surgical hub may be positioned in the OR. Once powered up, the surgical hub may use an ultrasonic echo to determine the OR boundaries (e.g., walls) and large equipment locations to map room. A grid map may be established with all required boundaries.

When an HCP enters into OR theater, the HCP may be identified as entering via a BLE beacon associated with HCP. The surgical hub may check the HCP into theater. The surgical hub may begin tracking the HCP via an optical camera. The IR camera may perform the initial scan of the identified HCP for base line stress level(s). Once procedure begins, the audio monitoring system may monitor and record sounds. The surgical hub may monitor for voice inflections and/or raised nervous voices The audio monitoring system can be synchronized with the IR camera, for example, for verifying an increase in stress levels. This process may be performed for multiple HCPs.

The HCPs in the OR may be recognized and tracked via an ID badge having an RFID, NFC, and/or a wearable device. For example, as an HCP move in and out of a room, as they come close to another wearable device, as they come close to a surgical hub, the identity of the HCP may be determined. The surgical hub may request HCP identifying information from an RFID reader, NFC reader, or a wearable device, upon detecting an HCP entering the OR. The surgical hub may confirm the identity of an HCP based on other source(s) of information. The surgical hub may assume that the identity of the HCP associated with an ID badge or a wearable device until the ID badge or wearable device is off. Details related to identifying an HCP and/or a user role via a wearable device may be found in U.S. application Ser. No. 17/156,324, entitled ACTIVE RECOGNITION AND PAIRING SENSING SYSTEMS, which is herein incorporated by reference in its entirety.

The HCPs in the OR may be recognized and tracked via video processing from video captured by one or more cameras in the OR. Various known image or video processing technologies, such as keypoint detection and analysis, bounding box annotation, polygon mesh processing, image segmentation, facial recognition, gesture recognition, point cloud, lines and splines, and/or the like may be used to analyze the video feeds.

The location, movement, and/or orientation of various surgical products and instruments in the operating room may be identified and tracked. For example, a gyroscope or 3 axis accelerometers may be used to determine device orientation and position.

For example, a surgical instrument may be identified via one or more spatial registration markers located thereon. For example, visible fiducial markers could be placed on the instrument. The surgical hub may monitor the location, movement, and/or orientation of the surgical instrument via one or more camera in the OR. The fiducial marks may be in a predefined pattern. The surgical hub may associate a surgical instrument with particular fiducial mark(s) and may use the mark(s) to identify and model the instrument with the 3D computer environment it creates and records. The registration allows for the compensation for translation, rotation, scale, skew, and perspective. This may enable the surgical hub to detect and monitor the instruments even once a portion of the instrument is obscured.

For visible monitoring, camera calibration may be conducted when the system starts up. A predefined set of calibration markers within the hub camera view that may be fixed, such that the surgical hub may calibrate the camera for distance and focal length. The surgical hub may determine the exact length from itself to another calibration preset scale in the OR, and may use the measurement and the scale to calibrate the camera and focal distance.

For example, the surgical hub may determine the exact distance via a measurement system. For example, measurement system(s) that employ laser Doppler, ultrasonic pinging, RF and/or other energy digital communication may be perform distance measurement and send the measurements to the surgical hub. The measurement system may be included in the surgical hub.

Distance may be inferred from active and/or passive electronic signal processing. For example, by monitoring the signal strength and compensating for emission power, emitting device antenna path, fight path, receiving device antenna path, and/or receiver sensitivity the communication between two paired systems or devices, the distance between the two systems or devices may be determined. For example, UHF or HF RFID tagged object may be tracked through a combination of predefined tag and distances in combination with unknown tags. The tags may be used to identify a product, device or instrument, and may allow the product, device or instrument tracked within the OR once identified. The tags may provide further information about the identified product, device or instrument. A RFID map may be generated from passive or active references tags with known locations (e.g., landmarks) to locate any unknown tag detected by the RFID reader antennas. The distances between the readers and the common detected tags may be measured using a large-scale path loss propagation model. The distance between the unknown tag and the detected landmarks (e.g., inter-tags distance) may be calculated.

A millimeter-wave radar may be used to track objects. Millimeter-wave radar may achieve an accuracy of around a few micrometers. With the radar operating using frequency-modulated continuous waves (FMCW), frequency and/and phase of radar beat signal may be used to determine the distance between the radar sensor and the object from which the radar signal is reflected.

A mapping or evaluation of the bounds of the operating room may be performed. For example, the surgical hub 20006 may maintain spatial awareness during operation by periodically mapping its operating room, which can be helpful in determining if the surgical hub 20006 has been moved. The reevaluation can be performed periodically or it can be triggered by an event such as observing a change in the devices of the HCP monitoring system 20002 that are deemed within the operating room. The change may be the detection of a new device that was not previously deemed as within the bounds of the operating room. The change may be a disappearance, disconnection, or un-pairing of a paired device that was previously deemed as residing within the operating room. The surgical hub 20006 may continuously monitor the connection with paired devices to detect the disappearance, disconnection, or un-pairing of a paired device.

An operating-room mapping module may contain a compass and integrated Bluetooth transceiver. Other communication mechanisms, which are not significantly affected by the hospital environment or geographical location, can be employed. Bluetooth Low Energy (BLE) beacon technology may achieve indoor distance measurements with accuracy of about 1-2 meters, with improved accuracy in closer proximities (within 0-6 meters). To improve the accuracy of the distance measurements, a compass is used with the BLE. The operating-room mapping module may the BLE and/or the compass to determine where modules are located in relation to the patient. For example, two modules facing each other (detected by compass) with greater than one meter distance between them may clearly indicate that the modules are on opposite sides of the patient. The more "hub"-enabled modules that reside in the operating room, the greater the achievable accuracy becomes due to triangulation techniques. The operating-room mapping module may be included in the surgical hub 20006 as described herein. The operating-room mapping module may be in operative communication with the surgical hub 20006 as described herein.

The operating-room mapping module may map the physical location of device(s) and/or surgical modules that resides within the operating room. This information could be used by the user interface to display a virtual map of the room, enabling the user to identify which modules more easily are present and enabled, as well as their current status. The mapping data collected by surgical hub 20006 may be analyzed for identifying how an operating room is physically setup, for example.

For example, the surgical hub 20006 may determine a device's location by assessing transmission radio signal strength and direction. For Bluetooth protocols, the Received Signal Strength Indication (RSSI) is a measurement of the received radio signal strength. In one aspect, the devices of the HCP monitoring system 20002 can be equipped with USB Bluetooth dongles. The surgical hub 20006 may scan the USB Bluetooth beacons to get distance information. For example, multiple high-gain antennas on a Bluetooth access point with variable attenuators can produce more accurate results than RSSI measurements. The hub surgical hub 20006 may determine the location of a device by measuring the signal strength from multiple antennas.

The surgical hub 20006 can identify components of the HCP monitoring system 20002 as they are brought into an operating room. For example, the devices of the HCP monitoring system 20002 can be equipped with an identifier recognizable by the surgical hub 20006, such as, for example, a bar code or an RFID tag. NFC can also be employed. The surgical hub 20006 can be equipped with a suitable reader or scanner for detecting the devices brought into the operating room. [Details related to Spatial awareness of surgical hubs in operating rooms, can be found in U.S. patent application Ser. No. 15/940,666, titled SPATIAL AWARENESS OF SURGICAL HUBS IN OPERATING ROOMS, filed Mar. 29, 2018, which is herein incorporated by reference in its entirety.

An aggregated network of surgical hubs can enable analysis of the efficiencies of operating room (OR), instruments, and HCPs. A computing system may link the inputs from multiple hub systems, track and aggregate the OR(s) and room turn over, instrument stock and utilization, costs, and efficiency of motion of the HCP(s) within and outside the OR(s). The efficiency of HCPs may be determined by OR utilization, OR turnover, efficiency within the procedure of movements, repositions, instrument exchanges, and/or repeated tasks. The computing system may identify the repeated movement paths of individual HCPs and compare the movement paths to the overall group. The efficiency of HCPs may be determined by aggregated OR utilization data, aggregated OR turnover data, aggregated HCP reposition data, and/or aggregated instrument exchange data associated with multiple surgical procedures in multiple ORs. The computing system may compare the movement paths to movement paths associated with various OR setups and/or instrument exchanges.

The computing system may obtain, and aggregate surgical monitored data associated multiple surgical procedures. The computing system may determine resource utilization adjustment(s) based on the aggregated surgical resource monitoring data and generate an output based on the determined adjustment(s). Surgical resource may include HCPs, surgical instruments, devices, medical supplies, and/or ORs etc. Surgical resource monitoring data may include HCP monitoring data and/or surgical instrument utilization data. The output may include, but not limited to, a control signal for adjusting an HCP assignment, adjusting surgery scheduling, adjusting surgical instrument allocation, adjusting surgical plan(s), notifying HCPs and/or administrators of surgical resource adjustments, notifying potential issues and/or providing recommendations.

The computing system may be or may include an HCP monitoring system such as the HCP monitoring system 20000, 20002, 20003, or 20004 as described herein with respect to FIGS. 1-3. The computing system may be a computing system operatively connected to the HCP monitoring system(s) 20000, 20002, 20003, and/or 20004. The computing system may be or may include the computing system 20271 described herein with respect to FIG. 9. The computing system may be or may include the computer system 20063 described herein, for example, with respect to FIG. 4. The computing system may be or may include the computer system 20064 described herein, for example, with respect to FIG. 4. The computing system may be or may include the surgical hub 20006 as described herein with respect to FIGS. 1-3, surgical hub system 20060 in FIG. 4, the computer-implemented interactive surgical system 20070, in FIG. 5, the surgical hub or computing device 20243 in FIG. 7, the surgical hub 20270 in FIG. 9, the console 20294 in FIG. 10, and/or the surgical hub 5104 in FIG. 11. For example, the computing system may obtain surgical monitoring data associated with one or more surgical procedures. The surgical procedures may take place in an OR or multiple ORs.

The surgical monitoring data may be obtained via the surgical hubs. For example, a surgical hub may obtain surgical monitoring data from various sensing systems such as the wearable sensing system(s) 20011, and/or environmental sensing system(s) 20015 described herein with respect to FIG. 1. The surgical hub may obtain surgical monitoring data from HCP monitoring devices 35510, environmental monitoring devices 35512, patient monitoring devices 5124, and/or modular devices 5102 as described herein with respect to FIG. 11.

The computing system may obtain the surgical monitoring data from various sensing systems such as the wearable sensing system(s) 20011, and/or environmental sensing system(s) 20015 described herein with respect to FIG. 1. The surgical monitoring data may be obtained from HCP monitoring devices 35510, environmental monitoring devices 35512, patient monitoring devices 5124, and/or modular devices 5102 as described herein with respect to FIG. 11.

The computing system may obtain surgical resource monitoring data associated with multiple surgical procedures, determine surgical resource efficiency based on the surgical resource monitoring data, and generate an output based on the determined surgical resource efficiency. The output may include but not limited to, a control signal for improving efficiency. For example, the computing system may aggregate surgical resource monitoring data associated with multiple surgical procedures and determine the surgical resource efficiency based on the aggregated surgical resource monitoring data.

Figure 12:
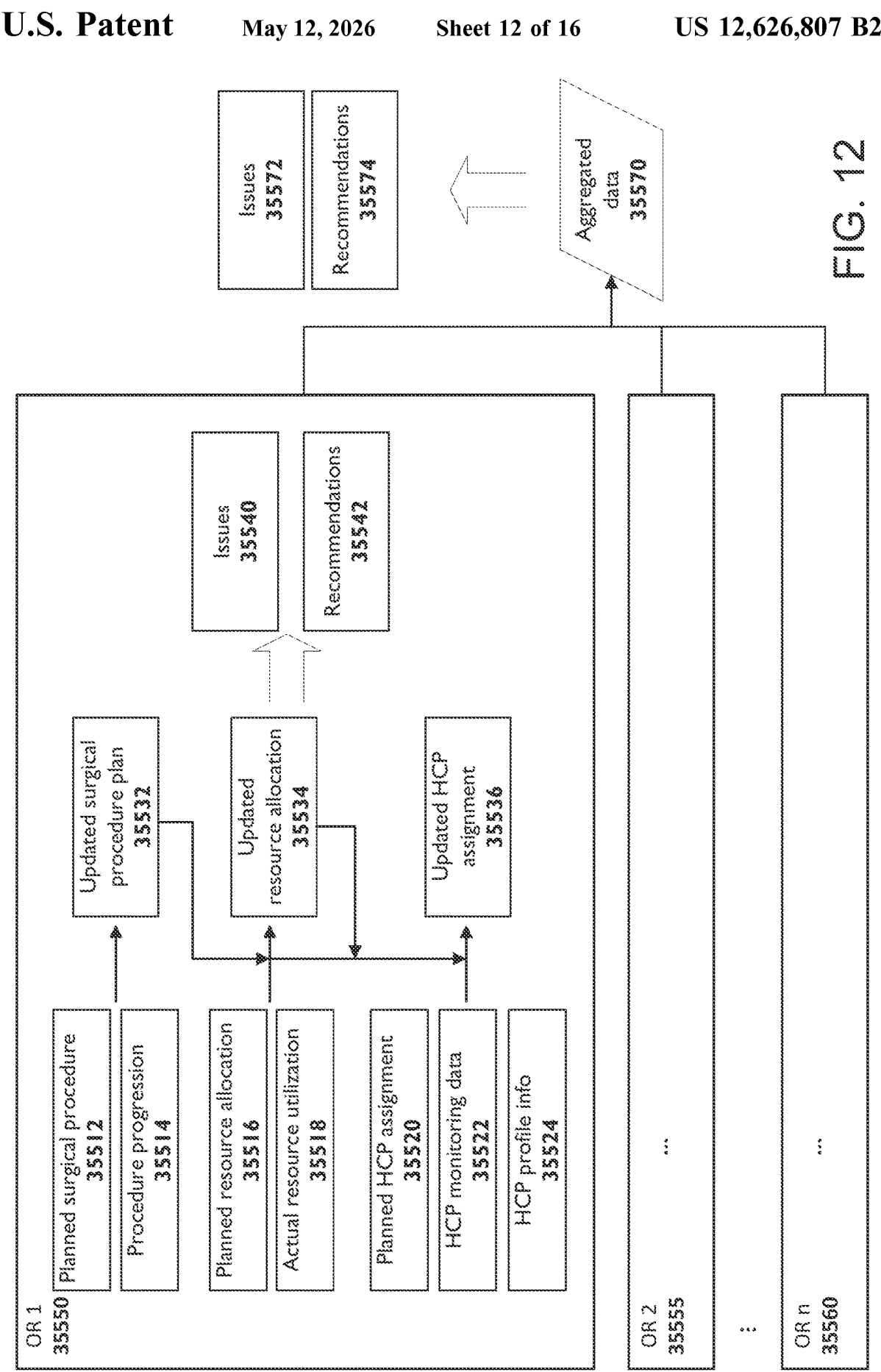
FIG. 12 shows an example surgical monitoring and analysis.

FIG. 12 shows an example surgical monitoring and analysis. As shown in FIG. 12, data inputs from multiple operating rooms such as OR1 35550, OR2 35555, through ORn 35560 may be aggregated to generate aggregated data 35570. Potential issues 35572, such as inefficient use of resources, repetitive tasks, interruptions to surgical procedure(s), task mismatch and/or deficient surgical supply stock may be identified based on the aggregated data 35570. Recommendations 35574, such as HCP task assignment adjustments, OR layout adjustments, resource allocation adjustments, and/or OR assignment adjustments may be generated based on the aggregated data 35570. Recommendations 35574 may include planning of OR(s), surgical instrument use, surgical instrument configuration, and/or capital spending to improve efficiency.

As shown in FIG. 12, planned data may be updated based on surgical monitoring data. Using OR1 35550 as an example, planned surgical data may include, but not limited to, planned surgical procedure 35512 (e.g., procedure steps, scheduled timing and expected duration associated with the procedure steps, and/or the like), planned resource allocation 35516 (e.g., surgical instrument or other supplies associated with the procedure steps), and/or planned HCP assignment 35520 (e.g., which HCP is assigned to which surgical task(s)). Surgical monitoring data may include, but not limited to, procedure progression data 35514, actual resource utilization information 35518 (e.g., information indicating if and when a surgical instrument is used during a surgical procedure), and/or HCP monitoring data 35522 (e.g., biomarker measurements and/or biomarker indications obtained via the wearable sensing system(s) 20011 described herein, HCP movement data, HCP step monitoring data, and/or other HCP monitoring data obtained via camera(s) in the OR). Procedure progression data 35514 may indicate the type of the surgery, current step of the surgery, the HCP(s) working on the surgery and/or other information indicative of procedure progression. Procedure progression data 35514 may include the surgical procedure and the contextual information that a surgical hub may derive as described herein with respect to FIGS. 8 and 11, and/or information that may be derived via camera-based surgical monitoring data.

As shown, planned surgical procedure data 35512 and procedure progression data 35514 may be combined to generate an updated surgical procedure plan 35532. For example, if the procedure progression data 35514 indicates a procedural step took longer than planned, the updated surgical procedure plan 35532 may be generated to reflect the delay. For example, if the procedure progression data 35514 indicates a complication has occurred, the updated surgical procedure plan 35532 may be generated with steps and/or instrument(s) to mitigate the complication.

Updated resource allocation information 35534 may be determined based on planned resource allocation 35516, actual resource utilization information 35518, and/or updated surgical procedure plan 35532. Updated HCP assignments 35536 may be generated based on planned HCP assignment 35520, HCP monitoring data 35522, HCP profile information 35524, updated surgical procedure plan 35532 and/or updated resource allocation information 35534.

Potential issues 35540, such as inefficient use of resources, repetitive tasks, interruptions to surgical procedure(s), task mismatch, the occurrence of the irregularity, accidental drop of an instrument, a potential complication, and/or deficient surgical supply stock associated with the surgical procedure taking place in OR1 may be identified, directly or indirectly, based on surgical monitoring data including procedure progression data 35514, actual resource utilization data 35518 and/or HCP monitoring data 35522. Potential issues 35540) may be identified based on the updated surgical procedure plan 35532, updated resource allocation information 35534 and/or the updated HCP assignments 35536.

Recommendations 35542 that may remediate the identified issues 35540 may be generated. For example, the computing system may generate a recommendation that additional HCP(s) outside the surgical room need to scrub and enter room. The recommendation may be generated, based on a detected surgical complication, for example. The recommendation may be sent via a display described herein, a speaker, an earpiece (e.g., ear bud, headset), a message board, etc. The recommendation may include instructions for an HCP to prepare for specific procedural steps, actions and/or other needs prior to entering the operating room.

Recommendations 35542 may be determined based, at least in part, on the surgical monitoring data. Recommendations 35542 may include HCP task assignment adjustments, OR layout adjustments, resource allocation adjustments, and/or OR assignment adjustments.

Figure 13:
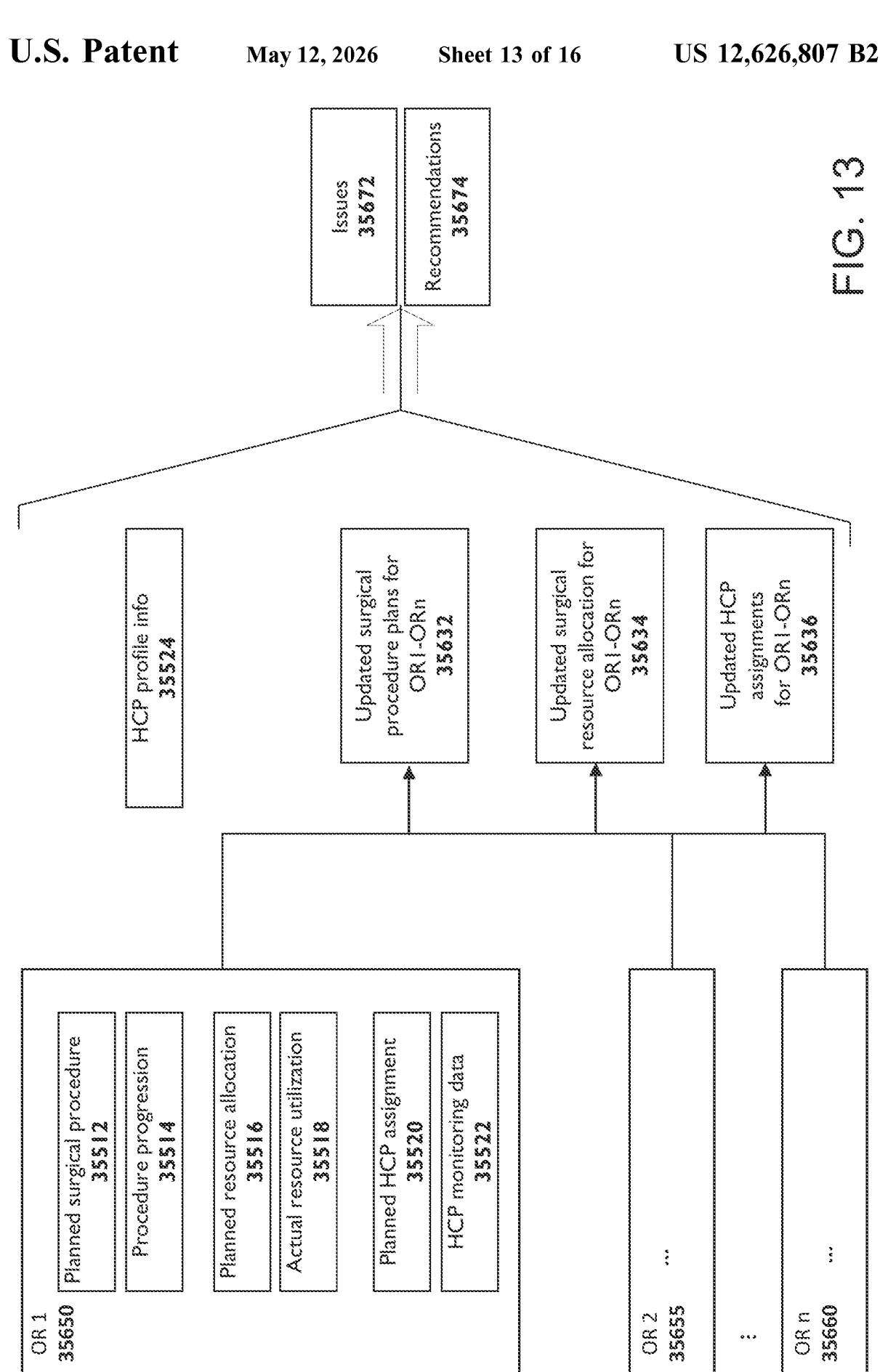
FIG. 13 shows an example surgical monitoring and aggregated analysis across multiple operating rooms.

FIG. 13 shows an example surgical monitoring and aggregated analysis across multiple operating rooms. As shown in FIG. 13, data inputs from multiple operating rooms such as OR1 35650, OR2 35655, through ORn 35660 may be considered collectively to generate updated surgical planning information for multiple operating rooms. Potential issues 35672 and recommendations 35674 for multiple operating rooms may be generated based on surgical monitoring data across the multiple operating rooms.

Surgical procedure plans for multiple ORs may be updated collectively based on surgical monitoring data across the ORs. For example, the surgical monitoring data associated with the procedure taking place in one OR may be used to update the surgical procedure plan for another procedure taking place in a different OR.

As shown in FIG. 13, updated surgical procedure plans 35632 for OR1-ORn, updated resource allocation information 35634 for OR1-ORn, and/or updated HCP assignments 35636 for OR1-ORn may be generated based on surgical monitoring data across OR1-ORn. For example, the computing system may obtain planned surgical procedure 35512, planned resource allocation 35516, planned HCP assignment 35520, procedure progression data 35514, actual resource utilization information 35518, and/or HCP biomarker monitoring information 35522 from OR1 35650, OR2 35655 through ORn 35660 (e.g., via the surgical hub systems associated with the ORs). As described herein, the HCP biomarker monitoring information may be used to derive the HCP's fatigue level, stress level, concentration level and/or other conditions that may impact their performance during a procedure. The computing system may aggregate the obtained multi-OR surgical information and use the aggregated data to generate the updated surgical procedure plans 35632 for OR1-ORn, updated resource allocation information 35634 for OR1-ORn, and/or updated HCP assignments 35636 for OR1-ORn.

HCP profile information 35524 may include the skill set(s) of the HCPs, certifications, and/or the experience level of HCPs. For example, HCP profile information may indicate the number of years an HCP has worked on a type of task, a type of surgery, and/or in the field. HCP profile information may indicate an expected duration an HCP takes to complete a task. HCP profile information 35524 may include surgical outcomes associated with the HCPs. HCP profile information 35524 may include HCP collaboration data, such as the number of procedures certain HCPs have worked together on. HCP profile information 35524 may include hours worked (e.g., during a period of time), and/or work hours (e.g., when an upcoming shift may start, when the current shift may end).

HCP profile information 35524 may be used to predict procedure time and outcomes. The computing system may identify HCP(s) to be assigned to a procedure, or pair HCPs with surgeons to improve surgical outcome and/or efficiency.

The aggregated data 35572 may be used to determine upcoming activity levels and may identify the time and location where additional HCP(s) may be needed. The skill level and/or experiences associated with the additional HCP(s) may be determined and indicated by the computing system. The computing system may identify HCP(s) to accommodate the needs, for example, based on the HCP profile information 35524, planned HCP assignment 35520, HCP monitoring data 35522 (e.g., HCP biomarker measurements), and/or updated HCP assignment 35536. HCP skill level, experience level, availability, fatigue level and/or stress level may be determined based on the HCP profile information 35524, planned HCP assignment 35520, HCP biomarkers 35522, and/or updated HCP assignment 35536, and used by the computing system to identify HCP(s) suitable for meeting the identified needs.

The computing system may determine skillset(s) associated with a procedure, based on the type of procedure to be or is being performed, the risk of complications, the patient's characteristics, operating room layout, surgical equipment layout, surgical instrument(s) that may be used. The computing system may identify an HCP or a team of HCPs to complete the procedure based on HCP availability, the determined skillset(s) associated with the procedure, the HCPs' experience level, the HCPs' skill level, surgical outcomes associated with the HCPs and/or HCP collaboration data. The computing system may identify the best overall team to complete the procedure for the patient outcomes, efficiency and/or cost.

For example, issues 35672 may include a lack of HCP having a needed skillset in the OR during a procedure. The computing system may identify, for example, based on planned surgical procedure 35512 and/or the procedure progression 35514 information, a skillset associated with an upcoming task in the procedure. The computing system may determine whether at least one HCP in the OR possess such skillset. Upon determining a lack of HCP having this needed skillset, the computing system may send a notification to a notification device outside the OR (e.g., a device associated with an HCP scheduling personnel), indicating that the skill set is not supported within the OR. The task mismatch with the skill sets available in the OR may be identified and indicated to an HCP in the OR.

For example, the computing system may identify potential issue(s) that may inhibit the coming procedures and provide an indication of such issue(s), associated time, and/or location. For example, the computing system may identify potential issue(s) associated increased activity levels and/or special expertise and may provide an indication of such issue(s), associated time, and/or location.

Figure 14:
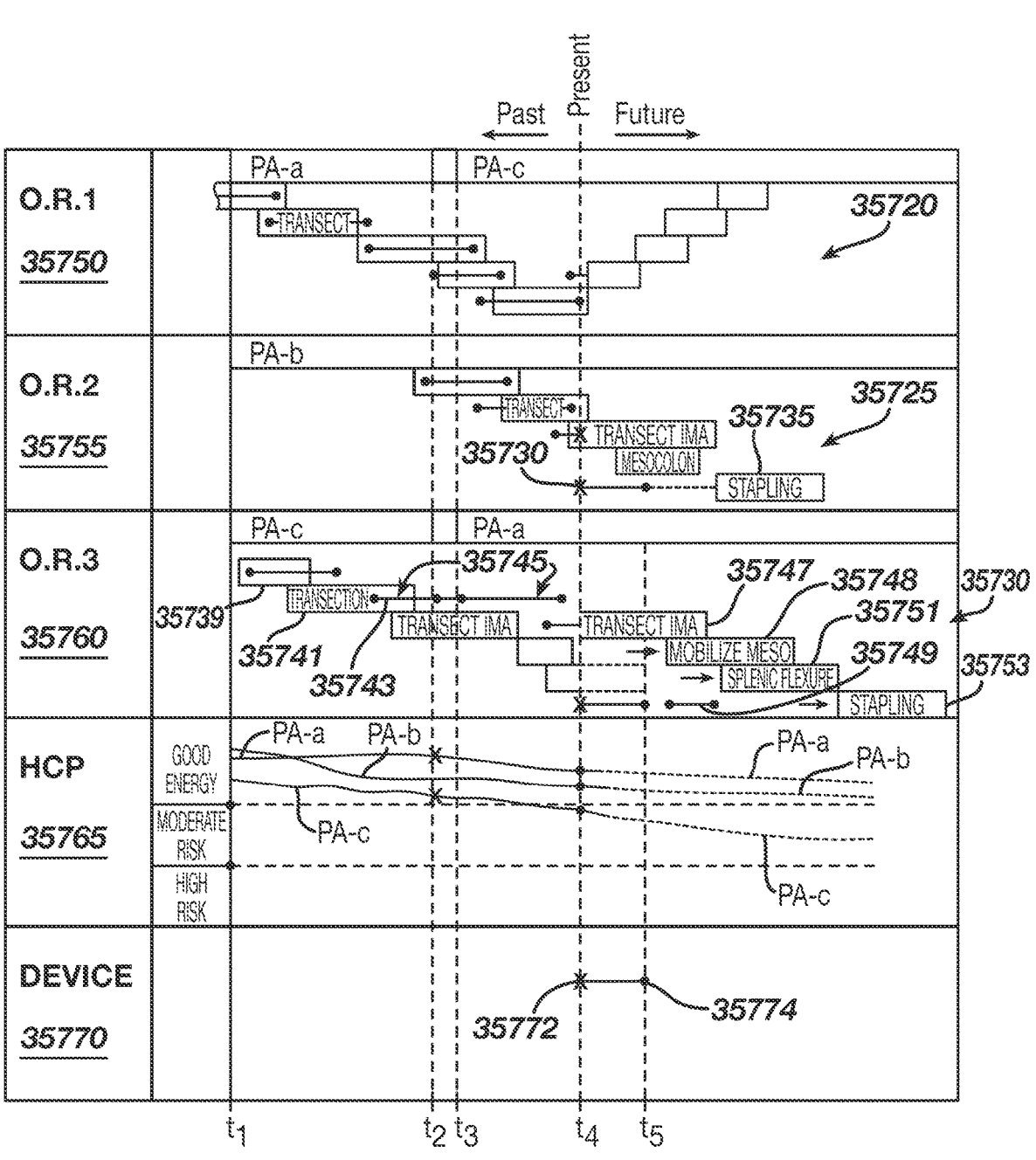
FIG. 14 shows example display summarizing surgical procedures, HCP, surgical device stock status, highlighting deficiencies and recommending remediations across multiple operating rooms.

FIG. 14 show example display summarizing surgical procedures, HCP, surgical device stock status, highlighting deficiencies and recommending remediations across multiple operating rooms. The procedure summary information may indicate the type of surgery, the planned duration for each surgical step, and projected/update duration for the surgical step based on the surgical monitoring information. Procedure summary information may include planned, actual and projected HCP assignment information, planned, actual and projected surgical step information, and/or planned, actual and projected surgical resource information.

As shown in FIG. 14, surgical planning information and surgical monitoring information across multiple ORs may be summarized and analyzed collectively. As shown, multiple surgical procedures may be carried out in different ORs, such as OR1 35750, OR2 35755, OR3 35760. Procedure summary information 35720, 35725 and 35730 for ORs 35750, 35755 and 35760 may be displayed side by side in a time aligned fashion. The procedure summary information may indicate the type of surgery associated with each OR.

For example, the procedure summary information 35720 for OR1 35750 may indicate that a lung lobectomy procedure is being carried out in OR1 35750. The procedure summary information 35725 for OR2 35755 may indicate that the procedure carried out in OR2 35755 is a gastrectomy procedure. The procedure summary information 35730 for OR3 35760 may indicate that the procedure carried out in OR3 35760 is a colon laparoscopic low anterior resection procedure.

Procedure summary information 35720, 35725 and 35730 may include HCP assignment information, surgical step information, and/or surgical resource information, which may be updated in real time as the surgeries progress. HCP monitoring data 35765 may be indicated along the same timeline. As shown, the energy levels of the HCPs, for example, physician assistant a (PA-a), physician assistant b (PA-b), physician assistant c (PA-c), who are assigned to OR1 35750, OR2 35755, OR3 35760 may be indicated. Device utilization information 35770 may be indicated along the same timeline as the procedure summary information 35720, 35725 and 35730.

The procedure summary information may indicate planned surgical procedure information, surgical progression information and/or updated surgical procedure plans as described herein, for example, with respect to FIGS. 12 and 13. As shown, time t1 may indicate the beginning of one or more procedures. Before the surgeries begin, for example, at t1 or before t1, the planned surgical procedure information, the planned resource application and/or the planned HCP assignment as described herein with respect to FIGS. 12 and 13, may be displayed as procedure summary information. The procedure summary information may include planned surgical steps, shown in boxes, such as transect, transect IMA, stapling, mobilize meso, etc, as shown in FIG. 14. As time progresses, the monitored procedure step start time and end time may be indicated in the procedure summary information. Present time line t4 may indicate the present time and may move as time progresses. The planned surgical steps may be updated by the computing system based on surgical monitoring data, as described herein. The monitored procedure step start time and end time (e.g., actual start and end times) may be indicated in the procedure summary information. As shown in FIG. 14, the monitored procedure step start and completion times may be indicated via dots connected with solid lines.

The computing system may derive the actual procedural step start time and completion time based on surgical monitoring data derived via various sensing systems and/or situational awareness information as described herein. For example, the transect step in OR1 35750 may start and end later than planned. The next step may take less time than planned, and as a result the following steps may start earlier than planned. As shown, in OR3 35760, procedural step 35739 may take longer than expected, which may delay the transect step (35741 shows the planned start and end time, and 35743 shows the monitored start and end time). The computer system may determine that a complication may have occurred at 35745 during transect step. The complication may be detected based on surgical monitoring data (e.g., prolonged duration of the transect step, sudden drop of noise level in the OR, increase in measured HCP stress level and/or patient measurements). As indicated by the arrows, the timeline for the surgical procedure may be revised based on real-time surgical monitoring data. As shown, the planned start and end times for subsequent procedural steps, including transect IMA 35747, mobilize meso 35748, splenic flexure 35751 and stapling 35753, are updated (e.g., postponed, delayed) based on the detected complication 35745.

For example, the procedure summary information 35720 may indicate that a lung lobectomy is being carried out in OR1 35750. As shown, the procedure summary information 35720 may indicate that HCP PA-a is assigned to work on the lung lobectomy procedure in OR1 35750. The HCP monitoring data 35765 may include measured or derived energy level (e.g., based on biomarker measurements and/or other HCP monitoring data for an HCP) and projected energy level (e.g., energy level projected by extrapolating the measured energy level).

An HCP's energy level may be measured/determined based on biomarker measurements, for example. Based on biomarker measurements of an HCP, the computing system may determine a value associated with hydration/dehydration of the HCP. Dehydration may impact energy levels and make a person feel tired and fatigued. Less body fluid tends to increase heart rate. The computing system may analyze heartbeat data in the context of hydration levels and differentiate between stress and other heart elevation events from hydration. The computing system may employ a baseline measure to differentiate acute events from ongoing chronic events and to differentiate between fatigue and dehydration.

An HCP's fatigue level may be measured/determined based on instrument usage data, for example. The computing system may calculate a weighted measure of fatigue for the HCP operating the surgical instrument as well as others in the operating room. The weighted measure of fatigue may be based on cumulative cooperative events and contributions. For example, the weighted measure of fatigue may be based on the intensity of stress experienced by an HCP and the force exerted by the HCP over time in controlling an actuator such as closure trigger over time.

Details on energy level and fatigue level measurements are described in U.S. application Ser. No. 17/156,287, titled METHOD OF ADJUSTING A SURGICAL PARAMETER BASED ON BIOMARKER MEASUREMENTS, filed Jan. 22, 2021, the disclosure of which is herein incorporated by reference in its entirety.

The HCP energy level may be compared to one or more thresholds such as good-energy threshold, moderate-risk threshold, and/or high-risk threshold. The computing system may determine HCP assignment adjustments based on the measured energy levels associated with the HCPs, the projected energy levels associated with the HCPs, the one or more HCP energy thresholds and/or the surgical procedure information (including planned and/or updated surgical procedure information). For example, upon determining that an HCP's energy level (e.g., measured and/or projected energy level) falls below a threshold, the computing system may prompt the HCP to take a break, assign the HCP a less demanding task and/or identify another HCP to assume the HCP's assigned task.

For example, as shown in FIG. 14, the computing system, based on the measured and projected HCP energy level, may determine that PA-c is trending lower energy, with energy level dropping below the moderate-risk threshold around t3 and moving towards the high-risk threshold. The computing system may determine, for example, based on the planned procedure information and procedure progression data associated with OR3 35760, that the procedure PA-c is assigned to is a potentially long procedure. The computing system may identify another assignment for PA-c based on the surgical progression information associated with the other operating rooms. For example, a shorter and/or less risky procedure, such as procedure in OR1 35750 may be identified for HCP PA-c. The computing system may identify PA-a, whose energy level is projected to remain above the good-energy threshold, as a replacement HCP for PA-a. The timing for re-assignment may be determined based on the projected time of an HCP's energy level crossing a threshold, and/or a projected or estimated downtime for the HCP as determined based on the procedure progression information.

The computing system may notify the HCP assignment adjustment to PA-a, and PA-c. The HCP adjustment may be sent to an HCP scheduling personnel. As shown in FIG. 14, at t2, the computing system may instruct PA-a to leave OR1 35750 and walk over to OR3 35760 to work on the procedure that takes place in OR3 35760, and instruct PA-c to leave OR1 35750 and walk over to OR3 35760 to work on the procedure that takes place in OR1 35750. At t3, the re-assignment has been completed, with PA-c working in OR1 35750, and PA-a working in OR3 35760.

Resource allocation adjustments (e.g., surgical resource change recommendations) associated with multiple ORs may be generated based on the aggregated resource allocation and utilization data. As shown in FIG. 14, the procedure carried out in OR2 35755 may be a gastrectomy procedure, and PA-b may be assigned to work on the procedure. At t4, transection of inferior mesenteric artery (IMA) branches is performed. At 35730, the computing system may determine, for example, based on surgical monitoring data, that the planned circular stapler buttress adjunct is not acceptable for the upcoming stapling step 35735. The computing system may generate a notification requesting replacement buttress to be delivered to OR2 35755.

The computing system may identify a replacement buttress based on the planned and updated surgical procedure information associated with other ORs. For example, the computing system may determine that, based on the delay of the stapling step 35749 in OR3 35760, that the staple adjunct may not be needed and may be allocated to another OR until preparation time 35749 for stapling step 35753. For example, at 35774, the computing system may determine that the staple adjunct in OR3 35760 is not immediately used/needed and may allocate the staple adjunct to OR2 35755 until preparation time 35749.

FIG. 15 shows an example efficiency analysis based on surgical monitoring data. As shown, at 35802, surgical monitoring data associated with multiple surgical procedures may be obtained. For example, surgical monitoring data may include HCP monitoring data, surgical resource monitoring data, surgical instrument utilization data, surgical procedure progression data, instrument stock and utilization data; OR turnover data, and/or costs associated the surgical procedure(s). The computing system may obtain surgical monitoring data from one or more surgical hubs, one or more environmental monitoring device, one or more patient monitoring devices, one or more HCP monitoring devices, and/or other monitoring devices.

As shown in FIG. 15, at 35804, surgical resource utilization adjustment(s) may be determined based on the surgical monitoring data. Surgical resource utilization adjustments may include, but not limited to, HCP task assignment adjustment(s) for reducing the distance HCP(s) need to travel to carry out the surgical procedures, OR layout adjustment(s), surgical instrument utilization allocation adjustment(s), and/or medical facility layout adjustments. At 35806, an output may be generated based on the surgical resource utilization adjustment(s). The output may include a control signal for adjusting an HCP assignment, adjusting surgery scheduling, adjusting surgical instrument allocation, adjusting surgical plan(s), notifying HCPs and/or administrators of surgical resource adjustments, notifying potential issues and/or providing recommendations. For example, the output may include a visual indication of the resource utilization adjustment(s), an audible indication of the resource utilization adjustment(s), notification(s) to HCPs inside the OR, notification(s) to HCPs outside the OR (e.g., instrumenting HCPs to be scrubbed in to provide additional support in a surgery), notification(s) to a surgical instrument supply department (e.g., requesting an instrument to be delivered to the OR), an indication to the patient's family for communicating procedure status and/or other indications. The output may include an indication of issues identified based on the surgical monitoring data, and/or recommendations for resolving or mitigating the issues.

For example, issues 35540, 35572 and/or 35672 shown in FIGS. 12 and 13 may include an irregularity, such as an error, an accident and/or an abnormality associated with a patient's anomy.

The computing system may detect an irregularity based on surgical monitoring data and generate an indication of the irregularity. For example, the computing system may predict an irregularity based on surgical monitoring data and generate an indication of the irregularity in advance of the occurrence of the irregularity. The indication may include an irregularity prevention recommendation for preemptively mitigating the irregularity.

Surgical instrument allocation for one or more procedures may be obtained and, predicted or projected surgical instrument utilization data may be determined based on the surgical instrument utilization monitoring data and the updated surgical procedure plans. For example, based on surgical monitoring data (e.g., derived based on camera-based data and/or instrument-embedded sensor-based data), the computing system may detect that a surgical instrument has been dropped. The computing system may detect that a surgical instrument has been displaced and cannot be used, for example, based on RFID zone violation. Upon the detection, the computing system may generate a notification indicating that a replacement instrument needs to be delivered to the OR. For example, the computing system may detect that the wrong-colored cartridge has been installed into a surgical stapling instrument, or that the wrong-colored cartridge is placed on the preparation table for installation into the surgical instrument. The detection of the wrong cartridge has been or is about to be installed may be made based on the surgical procedure plan 35632 and/or 35532 and procedure progression data 35514 such as video monitoring data. Upon detection, the computing system may generate a notification indicating that a replacement cartridge and/or a replacement surgical stapling device needs to be delivered to the OR. The notification for replacement instrument and/or medical supplies may be sent to a device outside of the OR, such as a notification device associated with the instrument supply room. This may enable timely instrument replacement, thus prevent, minimize, or reduce delay in the surgery caused by inadvertent errors.

For example, based on surgical monitoring data derived from imaging-based data, the computing system may detect an abnormality associated with a patient's anatomy. For example, the anatomical structures of a patient may be found in different places than would be considered normal. For example, for the majority of people, the heart can be found just slightly to the left of the sternum. However, in a condition known as dextrocardia, a person's heart may be found to the right of the sternum instead, as a mirror image of a normal cardiac anatomy. These types of abnormalities are rare, but sometimes may interfere with other systems, or have the potential to result in missed diagnoses or additional complications within surgery.

Upon detection of an abnormality associated with a patient's anatomy, the computing system may generate an adjustment to the procedure plan. The computing system may add additional surgeon(s) to the procedure, for example, to reduce the risk, or provide guidance to less experienced surgeons. The computing system may identify the surgeon(s) to be assigned and generate a notification to surgeons indicating that they should prepare to join the OR. This may reduce or minimize disruptions during a procedure. The HCPs' stress level may be reduced, knowing that an automated response system could be triggered without having to request support.

The surgical monitoring data may be compared to standard or expected surgical data to identify potential errors. For example, the computing system may determine that a procedural step has not been performed properly and/or procedural steps have been performed out of order based on surgical monitoring data. The computing system may generate a notification to request a senior HCP's support. The notification may be sent to other surgeon(s) to indicate that guidance or teaching is needed, on site in the OR or through virtual means. For example, a surgeon outside OR could access the surgical displays and coach the surgeon in the OR to perform optimized approach or steps to take.

FIG. 16 shows an example efficiency analysis based on aggregated surgical monitoring data across multiple ORs. As shown, at 35812, surgical monitoring data associated with multiple surgical procedures in operation rooms may be obtained. At 35814, surgical monitoring data across multiple ORs may be aggregated. For example, as shown in FIG. 14, the surgical monitoring data across multiple ORs may be aggregated based on time alignment. At 35816, one or more adjustment(s), such as surgical procedure adjustments, HCP assignment adjustments, OR layout adjustments, surgical instrument utilization adjustments, and/or other adjustments as described herein may be determined based on the aggregated surgical monitoring data.

At 35818, an output may be generated based on the aggregated surgical resource utilization adjustment(s). For example, the output may include a visual indication of the resource utilization adjustment(s), an audible indication of the resource utilization adjustment(s), notification(s) to HCPs inside the OR, notification(s) to HCPs outside the OR (e.g., instrumenting HCPs to be scrubbed in to provide additional support in a surgery), notification(s) to a surgical instrument supply department (e.g., requesting an instrument to be delivered to the OR), an indication to the patient's family for communicating procedure status and/or other indications. The output may include an indication of issues identified based on the surgical monitoring data, and/or recommendations for resolving or mitigating the issues.

For example, the output may include indications may be provided to the HCP(s) to indicate ownership and responsibilities associated with the procedural steps during a procedure. The indications may be provided in real-time with audible plays to minimize interruptions and optimize efficiency.

For example, a dashboard may include indications that may identify the sequence of events (e.g., next steps), an indication of out of order step(s), and/or recommended adjustment(s). The indications on the dashboard may be generated based on planned surgical procedure data 35512, procedure progression data 35514, planned resource allocation data 35516, actual resource utilization data 35518, updated surgical procedure plan 35532 and/or updated resource allocation 35534. The recommended adjustment(s) may include, but not limited to, alter position in the OR, alter handoff of instruments, and/or cartridge replacement, for example, to optimize surgical time. As actions occur, the indications correspond to the actions on the dashboard may disappear. The dashboard may be displayed on a monitor as described herein, or a projection system that can move based on the HCPs' positions in the OR. The location of the projection may be determined such that the dashboard is projected in front of each OR personal. Surgery is stressful and can cause missed steps, or instruments, devices may not be prepared or ready when needed. The visual dashboard may utilize surgical monitoring data to track and identify when things are required from each HCP and provide details to that the HCP on the dashboard.

The computing system may monitor the HCPs' movement, as described herein. Upon detecting that an HCP leaves the OR, the computing system may determine adjustments to the ownership and responsibilities to remaining HCPs in OR and display updated indications on the dashboard. The adjustments may be indicated to the HCPs via audible indications. Other indications on the dashboard may be provided to the individual HCPs via personal audio devices. For example, indications of risks associated with a step may be provided via audio devices. The computing system may receive an indication from a lead HCP, such as a surgeon to adjust the content of the dashboard in real-time and may indicate the adjustments to other HCPs.

As described herein, HCP assignment, HCP utilization, patient throughput, medical instrument utilization, facility stock, OR turnaround and utilization may be summarized and/or aggregated.

Aggregated historic surgical procedure data may be used to recommend HCP assignment and team combinations. Historic surgical procedure data may include staffing information (e.g., HCP team combinations, HCP experience level, HCP skill set and/or the like), time, OR turnover, complication rate, patient outcomes and/or surgical resource utilization associated with surgical procedures carried out in the past.

For example, surgical outcomes (e.g., complications, success rating(s), surgery duration, or the like) may be correlated with HCP team combinations, HCP experience level, HCP skill set and/or the like. The computing system may generate HCP assignment recommendations, such as recommending specific HCP for a specific procedure, recommending a specific HCP for a specific task, and/or recommending a team combination for a procedure, based on the surgical outcome-HCP correlation data.

Figure 17:
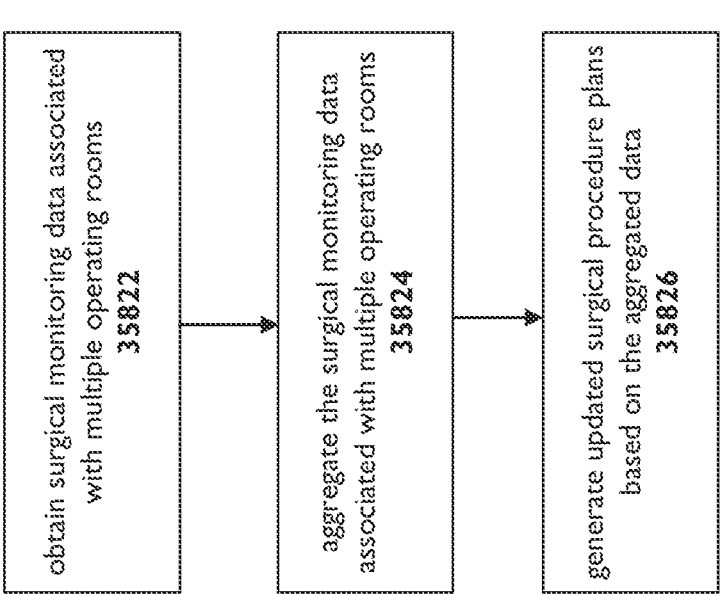
FIG. 17 shows an example updating of surgical procedural plans based on surgical monitoring data.

FIG. 17 shows an example updating of surgical procedural plans based on surgical monitoring data. As shown, at 35822, surgical monitoring data associated with multiple surgical procedures in operation rooms may be obtained. At 35824, surgical monitoring data across multiple ORs may be aggregated. At 35826, surgical procedure plans may be updated based on the aggregated surgical monitoring data.

Based on the aggregated data, the computing system may generate surgical planning information. For example, the computing system may, based on the aggregated historic surgical procedure data, determine surgical device allocation for a particular surgeon. For example, the surgical device most frequently used by the surgeon for the procedural step may be selected for inclusion in the surgical planning information. The computing device may, based on the aggregated historic surgical procedure data, determine surgical device allocation for a patient having one or more characteristics. The computing device may, based on the aggregated historic surgical procedure data, determine surgical device allocation for a particular procedure. For example, the surgical device most frequently used for the procedure in past surgeries may be selected for inclusion in the surgical planning information. For example, the surgical device associated with the highest recovery rate in past surgeries may be selected for inclusion in the surgical planning information.

Based on the aggregated data, the computing system may generate daily OR planning recommendations. Daily OR planning recommendations may include recommended OR(s) for upcoming surgeries, recommended surgery time, recommended HCP work hours and breaks. The computing system may predict staff shortages or overages based on the aggregated data. The aggregated data may be used to optimize HCP work.

The computing system may, based on the aggregated surgical procedure monitoring data, generate procedure plan(s) based on staff availability, instrument availability, and specialized OR equipment. For example, the computing system may determine that a specialized OR equipment may be needed for a procedure. The computing system may identify a time during which the instrument and at least one HCP having experience/skill set associated with the instrument are available and generate a procedure plan based on the identified time.

Figure 18:
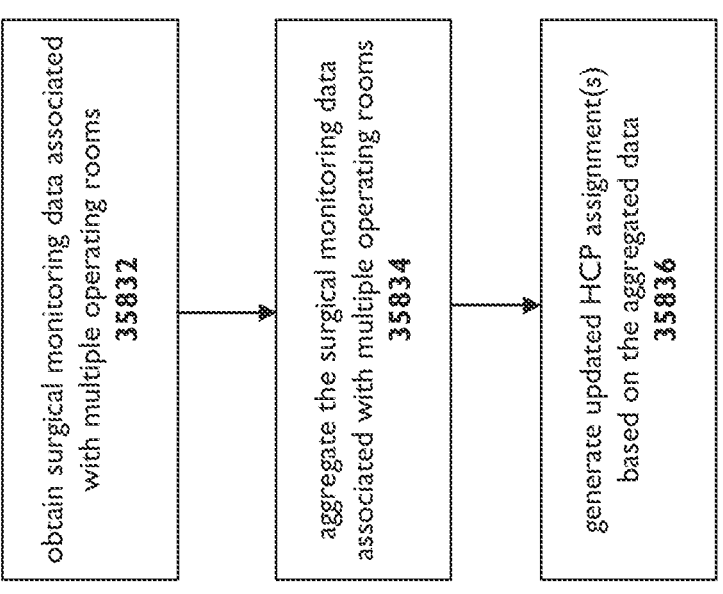
FIG. 18 shows an example adjustments of HCP assignments based on aggregated surgical monitoring data across multiple ORs.

FIG. 18 shows an example adjustments of HCP assignments based on aggregated surgical monitoring data across multiple ORs. As shown, at 35832, surgical monitoring data associated with multiple surgical procedures in operation rooms may be obtained. At 35834, surgical monitoring data across multiple ORs may be aggregated. At 35836, HCP assignments may be updated based on the aggregated surgical monitoring data.

The computing system may generate surgical planning recommendations based on surgical monitoring data associated with multiple surgical procedures. Large scale facility variables may be incorporated into surgical planning recommendation generation. Such variables may include, but not limited to, HCP availability, HCP stress level, HCP fatigue level, various HCP biomarkers, OR capacity, budget, patient volume, surgical outcomes, time of day, weather, and/or surgical device or surgical equipment availability, across multiple operating rooms. For example, availability for the HCPs in the surgical department of a hospital having multiple operating rooms may be considered when the computing system generates surgical planning recommendations.

A 2006 study found that the 146 nurses studied walked an average of 4-5 miles during a 12-hour shift, while most Americans walk just 2.5-3 miles during the course of an 18-hour day. The kind of walking nurses do at work has very little cardiac or stress-relieving benefits. In fact, walking that far during a shift can lead to fatigue, which could potentially reduce the quality of patient care.

The computing system may calculate an indication of a total distance traveled by an HCP who simultaneously work on multiple surgical procedures based on the HCP monitoring data. The computing system may obtain step monitoring data, such as distance traveled (e.g., during a period of time) for an HCP via one or more HCP wearable sensing systems and/or environmental sensing system(s) described herein. The computing system may determine suggested break time, fluid intake, food intake, and/or shoe replacement time for an HCP based on step monitoring data associated with the HCP. The computing system may provide an indication to prompt the HCP to take a break, suggest fluid and/or food intake, and/or prompt the HCP when shoes should be replaced, for example, when the distance traveled by the HCP during a time period exceeding a threshold.

The frequency of activities that require nurses to walk may impact the total distance traveled on a given shift. Operational factors that affect the total frequency may include the nurse-to-patient ratio, staffing, the type of patient population, and/or whether it is a day, evening or night shift. The computing system may determine staff shortage and/or overage based on HCP step monitoring data. For example, staff monitoring data may include an indication of the distance traveled by different HCPs during different shifts. Upon determining that the average distance traveled per HCP during a shift exceeds a threshold, the computing system may recommend adding additional HCP(s) to the shift. Upon determining that the average distance traveled per HCP during a shift is less than a threshold, the computing system may recommend reducing HCPs during the shift. Based on comparing that the average distance traveled per HCP during a first shift and the average distance traveled per HCP during a second shift, the computing system may identify HCP(s) being transferred between the two shifts.

The computing system may identify changes to the work-flow of an HCP based on HCP step monitoring data. For example, the HCP step monitoring data for an HCP may include the amount of steps traveled and the path traveled by the HCP, for example, obtained via one or more HCP wearable sensing system(s) and/or environment sensing system(s) described herein. The computing system may identify repetitive trips based on the path traveled by the HCP. The computing system may identify one or more tasks associated with the repetitive trips. For example, surgical procedure progression data associated a surgical procedure may be obtained. A set of repetitive trips made by an HCP may be identified based on the HCP step monitoring data. One or more task(s) associated with the repetitive trips made by the HCP may be identified by correlating the surgical procedure progression data with the repetitive trips made by the HCP. The computing system may determine a task assignment adjustment for reducing the distance traveled associated with the identified surgical task(s). For example, the computing system may determine a simplification of the identified task(s) that may reduce travel. The computing system may determine a time or scheduling change associated with the identified task(s). For example, the computing system may recommend one or more identified task be carried out in down time. Certain tasks that are planned to be performed during a procedure may be identified to be performed during pre-operative preparation.

The computing system may determine patient admission times based on surgical planning data and/or surgical monitoring data for reducing the distance traveled by the HCP(s). The patient admission times may be determined such that the HCP(s) may perform the same or similar tasks associated with multiple patients during the same trip.

The computing system may identify a set of combinable tasks based at least on the surgical procedure progression data and may recommend combining the identified set of combinable tasks. The combinable tasks my include the same or similar tasks associated with multiple patients. The combinable tasks my include the same or similar tasks associated with multiple operating rooms. The computing system may, based on the surgical monitoring data and/or surgical planning data, handle patient guidance and intake planning and notifications. The computing system may notify the HCP when and where to pick up the patient(s) to accomplish the steps that require interaction, allowing the HCP to support multiple patients at the same time and limiting their repetitive tasks. The workflow change recommendations may be provided to a notification device of the HCP, and/or a notification device associated with a facility scheduling personnel.

The computing system may determine that patient pick-ups may be combinable and may notify the HCP to pick up multiple patients during a single trip. For example, the computing system may identify, based on the surgical procedure progression data and/or the surgical planning data across multiple ORs, that multiple patients may start surgery around the same time. The computing system may generate notification(s) to the HCP(s), advising of the pickup time(s), locations and that the patients are to be picked up during the same trip. The computing system may generate notification(s) to the identified patients (e.g., to devices associated with the identified patients), advising the patients of the pickup time(s). For example, the computing system may identify, based on the surgical procedure progression data and/or the surgical planning data across multiple ORs, that surgical instruments and/or medical supplies are needed for multiple ORs. The computing system may notify an HCP to pick up and deliver the surgical instruments and/or medical supplies to the multiple ORs during the same trip.

The computing system may identify changes to the layout within the healthcare facility based on HCP step monitoring data. As described herein, the computing system may identify one or more tasks associated with the repetitive trips made by an HCP. The computing system may identify an aspect of OR layout associated with the identified surgical task(s) and generate an OR layout adjustment for reducing a path length associated with the set of repetitive trips. The computing system may identify an aspect of the healthcare facility layout associated with the identified repetitive task(s) and generate a healthcare facility layout adjustment for reducing a path length associated with the set of repetitive trips.

The invention claimed is:

1. A computing system comprising:
a processor configured to at least:
obtain first surgical monitoring data and second surgical monitoring data, wherein the first surgical monitoring data is associated with a first set of plurality of surgical procedures and the second surgical monitoring data is associated with a second set of plurality of surgical procedures, wherein the first set of plurality of surgical procedures is associated with a first operating room (OR), wherein the second set of plurality of surgical procedure is associated with a second OR, wherein the first surgical monitoring data comprises first healthcare personnel (HCP) monitoring data associated with the first OR, first surgical instrument utilization data associated with the first OR, first surgical procedure progression data associated with the first OR, first instrument stock and utilization data associated with the first OR, first OR turnover data associated with the first OR, and first cost data associated with the first set of plurality of surgical procedures for the first OR, wherein the second surgical monitoring data comprises second HCP monitoring data associated with the second OR, second surgical instrument utilization data associated with the second OR, second surgical procedure progression data associated with the second OR, second instrument stock and utilization data associated with the second OR, second OR turnover data associated with the second OR, and second cost data associated with the second set of plurality of surgical procedures for the second OR, wherein the first HCP monitoring data comprises first HCP step monitoring data associated with the first OR, and wherein the second HCP monitoring data comprises second HCP step monitoring data associated with the second OR;

identify a first set of repetitive trips in the first OR based on the first HCP step monitoring data and identify a second set of repetitive trips in the second OR based on the second HCP step monitoring data;

aggregate the first surgical monitoring data and the second surgical monitoring data, wherein to aggregate the first surgical monitoring data and the second surgical monitoring data comprises the processor being configured to:

aggregate the first set of repetitive trips in the first OR and the second set of repetitive trips in the second OR, aggregate the first surgical instrument utilization data associated with the first OR and the second surgical instrument utilization data associated with the second OR, aggregate the first surgical procedure progression data associated with the first OR and the second surgical procedure progression data associated with the second OR, aggregate the first instrument stock and utilization data associated with the first OR and the second instrument stock and utilization data associated with the second OR, aggregate the first OR turnover data associated with the first OR and the second OR turnover data associated with the second OR, and aggregate the first cost data associated with the first set of plurality of surgical procedures for the first OR and the second cost data associated with the second set of plurality of surgical procedures for the second OR, based on the aggregated first and second surgical monitoring data, the first set of repetitive trips, and the second set of repetitive trips, determine a first surgical resource utilization adjustment for a first HCP in the first OR and a second surgical resource utilization adjustment for a second HCP in the second OR, wherein the first surgical resource utilization adjustment for the first HCP comprises at least one of a first HCP task assignment adjustment for reducing a distance that the first HCP needs to travel to carry out the surgical procedures in the first OR, a first OR layout adjustment, a first surgical instrument utilization allocation adjustment for the first OR, and a medical facility layout adjustment and the second surgical resource utilization adjustment for the second HCP comprises a second HCP task assignment adjustment for reducing a distance that the second HCP needs to travel to carry out the surgical procedures in the second OR, a second OR layout adjustment, a second surgical instrument utilization allocation adjustment for the second OR, and the medical facility layout adjustment;

generate a first output signal based on the first surgical resource utilization adjustment and generate a second output signal based on the second surgical resource utilization adjustment;

generate a first message and a second message, wherein the first message is associated with the first output signal and the second message is associated with the second output signal; and send the first message to a first display associated with the first HCP and send the second message to a second display associated with the second HCP, wherein the first message indicates that the first display is to display the first output signal, and wherein the second message indicates that the second display is to display the second output signal.

2. The computing system of claim 1, wherein the first surgical monitoring data further comprises first surgical resource monitoring data, wherein the second surgical monitoring data further comprises second surgical resource monitoring data, and wherein the processor is further configured to:

receive the first surgical resource monitoring data associated with a first surgical procedure of the first set of plurality of surgical procedures;

receive the second surgical resource monitoring data associated with a second surgical procedure of the second set of plurality of surgical procedures; and aggregate the first and second surgical resource monitoring data, wherein the first surgical resource utilization adjustment and the second surgical resource utilization adjustment are determined based on the aggregated first and second surgical resource monitoring data.

3. The computing system of claim 1, the processor is further configured to:

identify a first set of plurality of surgical tasks associated with the first set of repetitive trips based on the first surgical procedure progression data associated with the first set of plurality of surgical procedures and identify a second set of plurality of surgical tasks associated with the second set of repetitive trips based on the second surgical procedure progression data associated with the second set of plurality of surgical procedures; and generate the first HCP task assignment adjustment for reducing a distance traveled associated with the identified first set of plurality of surgical tasks and generate the second HCP task assignment adjustment for reducing a distance traveled associated with the identified second set of plurality of surgical tasks.

4. The computing system of claim 1, wherein the first surgical monitoring data further comprises first surgical procedure progression data associated with the first set of plurality of surgical procedures from a first set of plurality of surgical hubs, wherein the second surgical monitoring data further comprises second surgical procedure progression data associated with the second set of plurality of surgical procedures from a second set of plurality of surgical hubs, and wherein the processor is further configured to:

obtain first surgical procedure planning data associated with the first set of plurality of surgical procedures and obtain second surgical procedure planning data associated with the second set of plurality of surgical procedures;

generate a first set of plurality of updated surgical procedure plans based on the first surgical procedure planning data and the first surgical procedure progression data with the first set of plurality of surgical procedures and generate a second set of plurality of updated surgical procedure plans based on the second surgical procedure planning data and the second surgical procedure progression data with the second set of plurality of surgical procedures;

obtain a first planned HCP task assignment associated with the first set of plurality of surgical procedures and obtain a second planned HCP task assignment associated with the second set of plurality of surgical procedures; and generate a first updated HCP task assignment associated with the first set of plurality of surgical procedures based on the first planned HCP task assignment, the first set of plurality of updated surgical procedure plans, and the first HCP monitoring data associated with the first set of plurality of surgical procedures and generate a second updated HCP task assignment associated with the second set of plurality of surgical procedures based on the second planned HCP task assignment, the second set of plurality of updated surgical procedure plans, and the second HCP monitoring data associated with the second set of plurality of surgical procedures.

5. The computing system of claim 1, wherein the first surgical monitoring data further comprises first surgical procedure progression data associated with the first set of plurality of surgical procedures from a first set of plurality of surgical hubs, wherein the second surgical monitoring data further comprises second surgical procedure progression data associated with the second set of plurality of surgical procedures from a second set of plurality of surgical hubs, and wherein the processor is further configured to:

determine HCP efficiency based on at least one of:

aggregated OR utilization data associated with the first set of plurality of surgical procedures and the second set of plurality of surgical procedure, aggregated OR turnover data associated with the first set of plurality of surgical procedures and the second set of plurality of surgical procedures, aggregated HCP reposition data associated with the first set of plurality of surgical procedures and the second set of plurality of surgical procedures, or aggregated instrument exchange data associated with the first set of plurality of surgical procedures and the second set of plurality of surgical procedures.

6. A computer-implemented method comprising:

obtaining first surgical monitoring data and second surgical monitoring data, wherein the first surgical monitoring data is associated with a first set of plurality of surgical procedures and the second surgical monitoring data is associated with a second set of plurality of surgical procedures, wherein the first set of plurality of surgical procedures is associated with a first operating room (OR), and wherein the second set of plurality of surgical procedure is associated with a second OR, wherein the first surgical monitoring data comprises first healthcare personnel (HCP) monitoring data associated with the first OR, first surgical instrument utilization data associated with the first OR, first surgical procedure progression data associated with the first OR, first instrument stock and utilization data associated with the first OR, first OR turnover data associated with the first OR, and first cost data associated with the first set of plurality of surgical procedures for the first OR, wherein the second surgical monitoring data comprises second HCP monitoring data associated with the second OR, second surgical instrument utilization data associated with the second OR, second surgical procedure progression data associated with the second OR, second instrument stock and utilization data associated with the second OR, second OR turnover data associated with the second OR, and second cost data associated with the second set of plurality of surgical procedures for the second OR, wherein the first HCP monitoring data comprises first HCP step monitoring data associated with the first OR, and wherein the second HCP monitoring data comprises second HCP step monitoring data associated with the second OR;

identifying a first set of repetitive trips in the first OR based on the first HCP monitoring data and identifying a second set of repetitive trips in the second OR based on the second HCP step monitoring data;

aggregating the first surgical monitoring data and the second surgical monitoring data, wherein aggregating the first surgical monitoring data and the second surgical monitoring data comprises:

aggregating the first set of repetitive trips in the first OR and the second set of repetitive trips in the second OR, aggregating the first surgical instrument utilization data associated with the first OR and the second surgical instrument utilization data associated with the second OR, aggregating the first surgical procedure progression data associated with the first OR and the second surgical procedure progression data associated with the second OR, aggregating the first instrument stock and utilization data associated with the first OR and the second instrument stock and utilization data associated with the second OR, aggregating the first OR turnover data associated with the first OR and the second OR turnover data associated with the second OR, and aggregating the first cost data associated with the first set of plurality of surgical procedures for the first OR and the second cost data associated with the second set of plurality of surgical procedures for the second OR, based on the aggregated first surgical monitoring data and second surgical monitoring data, the first set of repetitive trips, and the second set of repetitive trips, determining a first surgical resource utilization adjustment for a first HCP in the first OR and a second surgical resource utilization adjustment for a second HCP in the second OR, wherein the first surgical resource utilization adjustment for the first HCP comprises at least one of a first HCP task assignment adjustment for reducing a distance that the first HCP needs to travel to carry out the surgical procedures in the first OR, a first OR layout adjustment, a first surgical instrument utilization allocation adjustment for the first OR, and a first medical facility layout adjustment and the second surgical resource utilization adjustment for the second HCP comprises a second HCP task assignment adjustment for reducing a distance that the second HCP needs to travel to carry out the surgical procedures in the second OR, a second OR layout adjustment, a second surgical instrument utilization allocation adjustment for the second OR, and the medical facility layout adjustment;

generating a first output signal based on the first surgical resource utilization adjustment and generating a second output signal based on the second surgical resource utilization adjustment;

generating a first message and a second message, wherein the first message is associated with the first output signal and the second message is associated with the second output signal; and sending the first message to a first display associated with the first HCP and sending the second message to a second display associated with the second HCP, wherein the first message indicates that the first display is to display the first output signal, and wherein the second message indicates that the second display is to display the second output signal.

7. The computer-implemented method of claim 6, wherein the first surgical monitoring data is obtained from a first set of plurality of surgical hubs associated with a first set of plurality of ORs, wherein the second surgical monitoring data is obtained from a second set of plurality of surgical hubs associated with a second set of plurality of ORS, and wherein the method further comprises:

aggregating the first surgical monitoring data obtained from the first set of plurality of surgical hubs and the second surgical monitoring data obtained from the second set of plurality of surgical hubs, wherein the first surgical resource utilization adjustment is further determined based on the aggregated first and second surgical resource monitoring data and the second surgical resource utilization adjustment is further determined based on the aggregated first and second surgical resource monitoring data.

8. The computer-implemented method of claim 6, wherein the first set of plurality of surgical procedures is associated with a first set of plurality of ORs, wherein the first set of plurality of surgical procedures is associated with a first set of plurality of ORs, and wherein the method further comprising:

obtaining first resource allocation and utilization data associated with the first set of plurality of ORs and obtaining second resource allocation and utilization data associated with the second set of plurality of ORs;

obtaining first surgical outcome data associated with the first set of plurality of ORs and second surgical outcome data associated with the second set of plurality of ORs;

aggregating the first obtained resource allocation and utilization data associated with the first set of plurality of ORs and the second obtained resource allocation and utilization data associated with the second set of plurality of ORs; and generating a first resource allocation adjustment associated with the first set of plurality of ORs based on the aggregated first and second resource allocation and utilization data and the first surgical outcome data and generating a second resource allocation adjustment associated with the second set of plurality of ORs based on the aggregated first and second resource allocation and utilization data and the second surgical outcome data, wherein the first output signal comprises a first control signal for effectuating the first resource allocation adjustment, and wherein the second output signal comprises a second control signal for effectuating the second resource allocation adjustment.

9. The computer-implemented method of claim 6, wherein the first surgical monitoring data further comprises first biomarker measurement data associated with the first HCP and first surgical procedure progress data from a first set of plurality of surgical hubs associated with the first set of plurality of surgical procedures, wherein the second surgical monitoring data further comprises second biomarker measurement data associated with the second HCP and second surgical procedure progress data from a second set of plurality of surgical hubs associated with the second set of plurality of surgical procedures, and wherein the method further comprises:

projecting that a first task is to be performed during a first time period, wherein the first task is associated with the first OR and projecting that a second task is to be performed during a second time period, and wherein the second task is associated with the second OR;

determining a first fatigue level of the first HCP during the first time period based on the first biomarker measurement data and determining a second fatigue level of the second HCP during the second time period based on the second biomarker measurement data;

determining an availability of the first HCP associated the first time period based on a first surgical procedure planning data and the first surgical procedure progress data and determining an availability of the second HCP associated with the second time period based on a second surgical procedure planning data and the second surgical procedure progress data; and determining whether to assign the first task to the first HCP based on the first fatigue level and the determined availability of the first HCP during the first time period, wherein the first output signal comprises a first task assignment recommendation associated with the first HCP and determining whether to assign the second task to the second HCP based on the second fatigue level and the determined availability of the second HCP during the second time period, and wherein the second output signal comprises a second task assignment recommendation associated with the second HCP.

10. The computer-implemented method of claim 6, wherein obtaining the first surgical monitoring data comprises obtaining the first surgical monitoring data from a first set of plurality of surgical hubs, a first set of plurality of environmental monitoring devices, a first set of plurality of patient monitoring devices, and a first set of plurality of HCP monitoring devices, and wherein obtaining the second surgical monitoring data comprises obtaining the second surgical monitoring data from a second set of plurality of surgical hubs, a second set of plurality of environmental monitoring devices, a second set of plurality of patient monitoring devices, and a second set of plurality of one or more HCP monitoring devices.

11. The computer-implemented method of claim 6, wherein the first output signal comprises a first visual indication or a first audible indication of the first surgical resource utilization adjustment, and wherein the second output signal comprises a second visual indication or a second audible indication of the second surgical resource utilization adjustment.

* * * * *